US006410587B1

(12) United States Patent
Grainger et al.

(10) Patent No.: US 6,410,587 B1
(45) Date of Patent: Jun. 25, 2002

(54) COMPOUNDS AND THERAPIES FOR THE PREVENTION OF VASCULAR AND NON-VASCULAR PATHOLOGIES

(75) Inventors: David J. Grainger; James C. Metcalfe, both of Cambridge (GB); Sudhakar Kasina, Mercer Island, WA (US)

(73) Assignee: NeoRx Corporation, Seattle, WA (US)

( * ) Notice: Subject to any disclaimer, the term of this patent is extended or adjusted under 35 U.S.C. 154(b) by 0 days.

(21) Appl. No.: 09/567,558

(22) Filed: May 5, 2000

Related U.S. Application Data

(63) Continuation of application No. 09/057,323, filed on Apr. 9, 1998, now Pat. No. 6,117,911
(60) Provisional application No. 60/043,852, filed on Apr. 11, 1997.

(51) Int. Cl.[7] ...................... A61K 31/38; A61K 31/135; A61K 31/12
(52) U.S. Cl. ................ 514/445; 514/651; 514/685
(58) Field of Search ................ 514/445, 651, 514/685

(56) References Cited

U.S. PATENT DOCUMENTS

| | | | |
|---|---|---|---|
| 3,634,517 A | 1/1972 | Palopoli et al. ............ 260/590 |
| 4,133,814 A | 1/1979 | Jones et al. ................ 260/326 |
| 4,230,862 A | 10/1980 | Suarez et al. ............. 546/237 |
| 4,239,778 A | 12/1980 | Venton et al. ............. 424/305 |
| 4,307,111 A | 12/1981 | Crawley .................... 424/278 |
| 4,310,523 A | 1/1982 | Neumann .................. 424/240 |
| 4,323,707 A | 4/1982 | Suarez et al. ............. 564/324 |
| 4,380,635 A | 4/1983 | Peters ........................ 546/324 |
| 4,382,143 A | 5/1983 | Shepherd ................... 549/68 |
| 4,418,068 A | 11/1983 | Jones ......................... 424/267 |
| 4,442,119 A | 4/1984 | Magarian et al. ......... 424/274 |
| 4,696,949 A | 9/1987 | Toivola et al. ............ 514/648 |
| 4,839,155 A | 6/1989 | Mccague ................... 424/1 |
| 4,879,315 A | 11/1989 | Magarian et al. ......... 514/754 |
| 4,973,755 A | 11/1990 | Grafe, et al. .............. 564/324 |
| 4,990,538 A | 2/1991 | Harris et al. ............... 514/648 |
| 4,996,225 A | 2/1991 | Toivola et al. ............ 514/428 |
| 5,015,666 A | 5/1991 | Magarian et al. ......... 514/754 |
| 5,047,431 A | 9/1991 | Schickaneder et al. ... 514/648 |
| 5,075,321 A | 12/1991 | Schreiber .................. 514/317 |
| 5,098,903 A | 3/1992 | Magarian et al. ......... 514/255 |
| 5,189,212 A | 2/1993 | Ruenitz ..................... 562/468 |
| 5,192,525 A | 3/1993 | Yang et al. ................ 424/11 |
| 5,219,548 A | 6/1993 | Yang et al. ................ 424/1 |
| 5,254,594 A | 10/1993 | Niikura et al. ............ 514/648 |
| 5,280,040 A | 1/1994 | Labroo et al. ............. 514/422 |
| 5,389,670 A | 2/1995 | Fontana ..................... 514/443 |
| 5,391,557 A | 2/1995 | Cullinan et al. ........... 514/324 |
| 5,393,763 A | 2/1995 | Black et al. ............... 514/333 |
| 5,393,785 A | 2/1995 | Labrie et al. .............. 514/622 |
| 5,395,842 A | 3/1995 | Labrie et al. .............. 514/320 |
| 5,401,730 A | 3/1995 | Sauvage et al. ........... 514/165 |
| 5,411,988 A | 5/1995 | Bockow et al. ........... 514/560 |
| 5,418,252 A | 5/1995 | Williams ................... 514/443 |
| 5,434,166 A | 7/1995 | Glasebrook ............... 514/317 |
| 5,436,243 A | 7/1995 | Sachs et al. ............... 514/231 |
| 5,439,931 A | 8/1995 | Sales ......................... 514/443 |
| 5,439,932 A | 8/1995 | Cullinan .................... 514/324 |
| 5,441,964 A | 8/1995 | Bryant et al. .............. 514/324 |
| 5,441,966 A | 8/1995 | Dodge ....................... 514/324 |
| 5,441,986 A | 8/1995 | Thompson ................. 514/648 |
| 5,445,941 A | 8/1995 | Yang ......................... 435/6 |
| 5,446,053 A | 8/1995 | Keohane ................... 514/324 |
| 5,446,070 A | 8/1995 | Mantelle ................... 514/772.6 |
| 5,447,941 A | 9/1995 | Zuckerman ............... 514/324 |
| 5,451,589 A | 9/1995 | Dodge ....................... 514/324 |
| 5,451,590 A | 9/1995 | Dodge ....................... 514/324 |
| 5,451,603 A | 9/1995 | Piggott ...................... 514/422 |
| 5,455,275 A | 10/1995 | Fontana ..................... 514/648 |
| 5,457,116 A | 10/1995 | Black et al. ............... 514/324 |
| 5,457,117 A | 10/1995 | Black et al. ............... 514/337 |
| 5,461,064 A | 10/1995 | Cullinan .................... 514/324 |
| 5,461,065 A | 10/1995 | Black et al. ............... 514/324 |
| 5,462,949 A | 10/1995 | Jones et al. ................ 514/324 |
| 5,462,950 A | 10/1995 | Fontana ..................... 514/324 |
| 5,466,810 A | 11/1995 | Godfrey .................... 546/202 |
| 5,480,888 A | 1/1996 | Kodama et al. ........... 514/320 |
| 5,480,903 A | 1/1996 | Piggott et al. ............. 514/422 |
| 5,480,904 A | 1/1996 | Bryant et al. .............. 514/443 |
| 5,482,949 A | 1/1996 | Black et al. ............... 514/324 |
| 5,482,950 A | 1/1996 | Bryant et al. .............. 514/324 |
| 5,484,797 A | 1/1996 | Bryant et al. .............. 514/319 |

(List continued on next page.)

FOREIGN PATENT DOCUMENTS

| | | |
|---|---|---|
| DE | 4320896 | 1/1995 |
| DE | 4320898 | 1/1995 |
| EP | 0095875 | 12/1983 |
| EP | 0260066 | 3/1988 |
| EP | 0377526 B1 | 7/1990 |
| EP | 0584952 | 3/1994 |
| EP | 0629697 | 12/1994 |
| EP | 0659413 A2 | 6/1995 |
| EP | 0659415 A2 | 6/1995 |

(List continued on next page.)

OTHER PUBLICATIONS

"Schering/Orion Fareston Anti–Estrogen for Treatment of Metastatic Breast Cancer 'Similar' to Tamoxifen, FDA Oncologic Committee Says in Approval Vote", *F–D–C Reports*, 15–16, (Oct. 23, 1995).

(List continued on next page.)

*Primary Examiner*—Deborah C. Lambkin
(74) *Attorney, Agent, or Firm*—Schwegman, Lundberg, Woessner & Kluth, P.A.

(57) ABSTRACT

The invention provides a method of treating a mammal having, or at risk of, an indication associated with a TGF-beta deficiency comprising administering one or more agents that is effective to elevate the level of TGF-beta. The invention also provides novel compounds that elevate TGF-beta levels, as well as pharmaceutical compositions comprising compounds that elevate TGF-beta levels, and methods for detecting diseases associated with endothelial cell activation.

35 Claims, 14 Drawing Sheets

U.S. PATENT DOCUMENTS

| | | | |
|---|---|---|---|
| 5,484,808 A | 1/1996 | Grinnell et al. | 514/443 |
| 5,489,587 A | 2/1996 | Fontana | 514/233.5 |
| 5,491,159 A | 2/1996 | Malamas | 514/374 |
| 5,491,173 A | 2/1996 | Toivola et al. | 514/648 |
| 5,492,927 A | 2/1996 | Gitter et al. | 514/443 |
| 5,496,828 A | 3/1996 | Cullinan | 514/324 |
| 5,496,851 A | 3/1996 | Grinnell | 514/443 |
| 5,510,370 A | 4/1996 | Hock et al. | |
| 5,521,198 A | 5/1996 | Zuckerman | 514/324 |
| 5,534,527 A | 7/1996 | Black et al. | 514/333 |
| 5,552,415 A | 9/1996 | May | 514/324 |
| 5,563,054 A | 10/1996 | Briggs et al. | 435/127 |
| 5,571,808 A | 11/1996 | Leeds | 514/212 |
| 5,604,204 A * | 2/1997 | Ammann et al. | 514/12 |
| 5,605,700 A | 2/1997 | DeGregorio et al. | 424/448 |
| 5,616,608 A | 4/1997 | Kinsella et al. | 514/449 |
| 5,652,259 A | 7/1997 | May | 514/422 |
| 5,658,927 A | 8/1997 | Magarian et al. | 514/315 |
| 5,658,951 A | 8/1997 | Magarian et al. | 514/596 |
| 5,660,873 A | 8/1997 | Nikolaychik et al. | 427/2.24 |
| 5,686,476 A | 11/1997 | May | 514/324 |
| 5,693,607 A | 12/1997 | Segarini et al. | 514/2 |
| 5,716,981 A | 2/1998 | Hunter et al. | 514/2 |
| 5,719,191 A * | 2/1998 | Maclean et al. | 514/648 |
| 5,731,200 A | 3/1998 | Ichijo et al. | 435/365 |
| 5,733,925 A | 3/1998 | Kunz et al. | 514/499 |
| 5,770,609 A | 6/1998 | Grainger et al. | 514/319 |
| 5,847,007 A | 12/1998 | Grainger et al. | 514/651 |
| 5,856,342 A * | 1/1999 | Eek | 514/330 |
| 6,117,911 A * | 9/2000 | Grainger et al. | 514/648 |

FOREIGN PATENT DOCUMENTS

| | | |
|---|---|---|
| EP | 0659418 | 6/1995 |
| EP | 0659419 A1 | 6/1995 |
| EP | 0659429 A1 | 6/1995 |
| EP | 0664122 | 7/1995 |
| EP | 0664123 | 7/1995 |
| EP | 0664124 A1 | 7/1995 |
| EP | 0664125 | 7/1995 |
| EP | 0665015 | 8/1995 |
| EP | 0668075 | 8/1995 |
| EP | 0670162 | 9/1995 |
| EP | 0675103 | 10/1995 |
| EP | 0675121 | 10/1995 |
| EP | 0684259 A1 | 11/1995 |
| EP | 0699673 | 3/1996 |
| GB | 1015787 | 1/1966 |
| GB | 2273873 | 6/1994 |
| WO | 92/06068 | 4/1992 |
| WO | 93/11757 | 6/1993 |
| WO | 93/19746 | 10/1993 |
| WO | 94/09764 | 5/1994 |
| WO | 94/20098 | 9/1994 |
| WO | 94/20099 | 9/1994 |
| WO | 94/23068 | 10/1994 |
| WO | 95/04544 | 2/1995 |
| WO | 95/17095 | 6/1995 |
| WO | 95/17905 | 6/1995 |
| WO | 96/07402 | 3/1996 |
| WO | 96/21442 | 7/1996 |
| WO | 96/24356 | 8/1996 |
| WO | 96/40098 | 12/1996 |

OTHER PUBLICATIONS

Agarwal, A.K., et al., "Estrogen Receptor–Binding Affinity of Tamoxifen Analogs with Various Side Chains and their Biologic Profile in Immature Rat Uterus", *Steroids*, 56, 486–489, (1991).

Burton, T.M., "Lilly Osteoporosis Treatment Shows Promise", *The Wall Street Journal*, p. A3, A6, (Jun. 6, 1997).

Butta, A., et al., "Induction of Transforming Growth Factor Beta1 in Human Breast Cancer in Vivo Following Tamoxifen Treatment", *Cancer Research*, 52, 4261–4164, (1992).

Chander, et al., "Pyrrolidino–4–iodotamoxifen and 4–iodotamoxifen, New Analogues of the Antiestrogen Tamoxifen for the Treatment of Breast Cancer", *Cancer Res.*, 51, 5851–5858, (Nov. 1, 1991).

Chandrasekar, B., et al., "Dietary Omega–3 Lipids Delay the Onset and Progression of Autoimmune Lupus Nephritis by Inhibiting Transforming Growth Factor Beta mRNA and Protein Expression", *Journal of Autoimmunity*, 8, 381–393, (1995).

Charlier, et al., "Tamoxifen in the Treatment of Breast Cancer", *J. Gynecol. Obstet Biol. Reprod.*, 23, 751–756, (1994).

Colletta, A.A., et al., "Anti–oestrogens induce the secretion of active transforming growth factor beta from human fetal fibroblasts", *Br. J. Cancer*, 62, 405–409, (1990).

Coombes, R.C., et al., "Idoxifene: Report of a Phase I Study in Patients with Metastatic Breast Cancer", *Cancer Research*, 55, 1070–1074, (Mar, 1, 1995).

Cunningham, A., et al., "A Study of the Structural Basis of the Carcinogenicity of Tamoxifen, Toremifene and their Metabolites", *Mutation Research*, 349, 85–94, (1996).

Davies, A.M., et al., "Peroxidase Activation of Tamoxifen and Toremifene Resulting in DNA Damage and Covalently Bound Protein Adducts", *Carcinogenesis*, 16, 539–545, (1995).

Dowsett, M., "New Developments in the Hormonal Treatment of Breast Cancer", In: The Treatment of Cancer: Beyond Chemotherapy, Conference Documentation, The Glouster Hotel, London, 7 p., (Mar. 13–14, 1995).

Dragan, Y.P., et al., "Comparison of the Effects of Tamoxifen and Toremifene on Liver and Kidney Tumor Promotion in Female Rats", *Carcinogenesis*, 16, 2733–2741, (1995).

Grainger, D.J., et al., "A Pivotal Role for TGF–Beta in Atherogenesis?", *Biol. Rev.*, 70, 571–596, (1995).

Grainger, D.J., et al., "Release and Activation of Platelet Latent TFG–Beta in Blood Clots During Dissolution with Plasmin", *Nature Medicine*, 1, 932–937, (1995).

Grainger, D.J., et al., "The Serum Concentration of Active Transforming Growth Factor–beta)is Severly Depressed in Advanced Atherosclerosis", *Nature Medicine*, 1, 74–80, (Jan., 1995).

Hardcastle, I.R., et al., "Homologs of Idoxifene: Variation of Estrogen Receptor Binding and Calmodulin Antagonism with Chain Length", *J. Med. Chem.*, 39, 999–1004, (1996).

Hayes, D.F., et al., "Randomized Comparison of Tamoxifen and Two Separate Doses of of Toremifene in Postmenopausal Patients with Metastatic Breast Cancer", *Journal of Clinical Oncology*, 13, 2556–2566, (Oct. 1995).

Jones, R.H., et al., "Increased Susceptibility to Metal Catalysed Oxidation of Diabetic Lens subL Crystallin: Possible Protection by Dietary Supplementation with Acetylsalicyclic Acid", *Exp. Eye Res.*, 57, 783–790, (1993).

Kellen, J.A., et al., "The Effect of Toremifene on the Expression of Genes in a Rat Mammary Adenocarcinoma", *In Vivo*, 10, 511–514, (1996).

Knabbe, C., et al., "Induction of Transforming Growth Factor Beta by the Antiestrogens Droloxifene, Tamoxifen, and Toreifene in MCF–7 Cells", *Am. J. Clin. Oncol. (CCT)*, 14, S15–S20, (1991).

Kopp, A., et al., "Transforming Growth Factor Beta2 (TGF-Beta2) Levels in Plasma of Patients with Metastatic Breast Cancer Treated with Tamoxifen", *Cancer Research*, 55, 4512–4515, (Oct. 15, 1995).

Kuramochi, H., "Conformational Studies and Electronic Structures of Tamoxifen and Toremifene and Their Allylic Carbocations Proposed as Reactive Intermediates Leading to DNA Adduct Formation", *J. Med. Chem.*, 39, 2877–2886, (1996).

Loser, R., et al., "In Vivo and in Vitro Antiestrogenic Action of 3–Hydroxytamoxifen, Tamoxifen and 4–Hydroxytamoxifen", *Eur. J. Cancer Clin. Oncol.*, 21, 985–990, (1985).

Magarian, "The Medicinal Chemistry of Nonsteroidal Antiestrogenes: A Review", *Current Medicinal Chemistry*, 1, 61–104, (1994).

Majesky, M.W., et al., "Production of Transforming Growth Factor beta1 During Repair of Arterial Injury", *J. Clin. Invest.*, 88, 904–910, (1991).

McCaffrey, T.A., et al., "Fucoidan is a Non–Anticoagulant Inhibitor of Intimal Hyperplasia", *Biochemical and Biophysical Research Communications*, 184, 773–781, (1992).

Mccague, et al., "An Efficient, Large Scale Synthesis of Idoxifene ((E)–1(4–(2–(N–pyrrolidino)ethoxy)–1–(4–iodophenyl)–2–phenyl–1–butene", *Organic Preparations and Proc. Int.*, 26, 343–346 (1994).

Mccague, et al., "Synthesis of 4–Stannylated Tamoxifen Analogues: Useful Precursors to Radiolabelled Idoxifene and Axiridinyl 4–Iodotamoxifen.", *J. Labelled Compounds and Pharmaceuticals*, 34, 297–302 (1994).

Moorthy, B., et al., "Tamoxifen Metabolic Activation: Comparison of DNA Adducts Formed by Microsomal and Chemical Activation of Tamoxifen and 4–Hydroxytamoxifen with DNA Adducts Formed in Vivo", *Cancer Research*, 56, 53–57, (Jan. 1, 1996).

Murphy, C.S., et al., "Structure–Activity Relationships of Nonisomerizable Derivatives of Tamoxifen: Importance of Hydroxyl Group and Side Chain Positioning for Biological Activity", *Molecular Pharmacology*, 39, 421–428, (1991).

Murphy, L.C., et al., "Differential Effects of Tamoxifen and Analogs with Nonbasic Side Chains on Cell Proliferation in Vitro", *Endocrinology*, 116, 1071–1078, (1985).

Pennisi, E., "Drug's Link to Genes Reveals Estrogen's Many Sides", *Science*, 273, 1171, (Aug. 30, 1996).

Potter, et al., "A Mechanism Hypothesis for DNA Adduct Formation Following Hepatic Oxidative Metabolism.", *Carcinogensis*, 15, 439–442, (1994).

Sargent, L.M., et al., "Induction of Hepatic Aneuploidy in Vivo by Tamoxifen, Toremifene and Idoxifene in Female Sprague–Dawley Rats", *Carcinogenesis*, 17, 1051–1056, (1996).

Sudo, K., et al., "Antiestrogen–Binding Sites Distinct from the Estrogen Receptor: Subcellular Localization, Ligand Specificity, and Distribution in Tissues of the Rat", *Endocrinology*, 112, 425–434, (1983).

Testart, J., et al., "The Action of Anti–Inflammatory Drugs to the Fertility of Female Rats with Intrauterine Contraceptive Devices", *J. Reprod. Fert.*, 63, 257–261, (1981).

Wiseman, L.R., et al., "Toremifene—A Review of its Pharmacological Properties and Clinical Efficacy in the Management of Advanced Breast Cancer", *Drugs*, 54, 141–160, (Jul. 1997).

Yang, N.N., et al., "Estrogen Receptor: One Transcription Factor, Two Genomic Pathways", *Calcified Tissue Intl.*, 54, 342, (1994).

Yang, N.N., et al., "Identification of an Estrogen Response Element Activated by Metabolites of 17Beta–Estradiol and Raloxifene", *Science*, 273, 1222–1225, (Oct. 30, 1996).

Young, H., et al., "Pharmacokinetics and Biodistribution of Radiolabelled Idoxifene: Prospects for the Use of PET in the Evaluation of a Novel Antioestrogen for Cancer Therapy", *Nucl. Med. Biol.*, 22, 405–411, (May 1995).

\* cited by examiner

COMPOUNDS AND THERAPIES FOR THE PREVENTION OF VASCULAR AND NON-VASCULAR PATHOLOGIES

PRIORITY OF INVENTION

This application is a Continuation of U.S. patent application Ser. No. 09/057,323, filed Apr. 9, 1998, U.S. Pat. No. 6,117,911 (the '323 Application). The '323 Application is incorporated herein by reference.

This application claims priority under 35 U.S.C. §119(e) from U.S. Provisional Patent Application No. 60/043,852, filed Apr. 11, 1997.

BACKGROUND OF THE INVENTION

TGF-beta dynamically regulates the differentiation of smooth muscle cells, and has been postulated to maintain vessel wall structure. TGF-beta also appears to possess immunosuppressive properties which protect the vascular endothelium against local inflammation and damage. Moreover, TGF-beta may inhibit the proliferation and migration of smooth muscle cells after vascular injury.

TGF-beta is synthesized as a latent peptide (FIG. 1). Latent TGF-beta refers to any of several complexes that include the 25 kD TGF-beta dimer in association with the latency associated peptide (LAP) or any of several additional TGF-beta binding proteins (LTBPs). Latent TGF-beta has no biological activity, i.e., it does not bind to the TGF-beta receptors.

The 25 kD TGF-beta dimer is also found associated with matrix components or other plasma proteins (FIG. 1). TGF-beta that is associated with matrix components or other plasma proteins is termed mature TGF-beta. This association also prevents the binding of TGF-beta to the TGF-beta receptors.

In addition to latent and mature forms of TGF-beta, which cannot bind to the TGF-beta receptors and which possess no known biological activity, TGF-beta also exists in forms which are capable of binding to the TGF-beta receptors and which elicit biological effects (FIG. 1). These forms of TGF-beta are termed "active TGF-beta." One example of a form of active TGF-beta is the 25 kD TGF-beta dimer which is free from association with LAP/LTBPs, or matrix or plasma components. The process(es) by which the latent form of TGF-beta is converted to the active form is termed "activation." The process(es) by which the mature form of TGF-beta is converted to the active form is termed "release."

Decreased levels of TGF-beta have been implicated in the development of atherosclerosis. Atherosclerosis is a disease of the major arteries, typified by changes in the vessel wall architecture. At lesion-prone sites where the endothelium becomes damaged or dysfunctional, smooth muscle cells from the media of the vessel migrate into the intima. At these sites, leukocytes, and in particular, monocytes and macrophages invade the expanded intima. As the lesion develops, lipid from the circulation is deposited into the intima (reviewed in Ross, *Nature*, 362 801 (1993); Grainger et al. *Biol. Rev. Camb. Philos. Soc.*, 70, 571 (1995)).

Agents which elevate TGF-beta activity, such as tamoxifen (TMX) (Grainger et al., *Biochem. J.*, 294, 109 (1993)) and aspirin (Grainger et al., *Nat. Med.*, 1, 74 (1995)), can exhibit cardioprotective effects. However, the positive cardioprotective effects of these agents may be counterindicated by their potential side effects. TMX can cause liver carcinogenicity in rats, has been correlated with an increased risk of endometrial cancer in women and may increase the risk of certain gut cancers. Aspirin may result in ulcerogenesis and increased bleeding.

Agents which elevate TGF-beta levels may also be useful to prevent or treat diseases or conditions including cancer, Marfan's syndrome, Parkinson's disease, fibrosis, Alzheimer's disease, senile dementia, osteoporosis, diseases associated with inflammation, such as rheumatoid arthritis, multiple sclerosis and lupus erytematosus, and other autoimmune disorders. Such agents may also be useful to promote wound healing and to lower serum cholesterol levels.

Thus, there is a need for improved therapeutic methods and agents useful to maintain or elevate TGF-beta levels in mammals.

SUMMARY OF THE INVENTION

The present invention provides a method to maintain or elevate TGF-beta levels in a mammal, such as a human, in need of such therapy. The method comprises administering an effective amount of an aspirinate as defined herein. The method can also be carried out by administering an amount of a first therapeutic agent effective to elevate the level of latent TGF-beta and an amount of a second therapeutic agent effective to increase the level of TGF-beta which is capable of binding to the TGF-beta receptors, wherein said amounts are effective to maintain or elevate the level of TGF-beta in said mammal.

The invention also provides a method of preventing or treating a mammal, such as a human, having, or at risk of, a vascular indication which is associated with a TGF-beta deficiency. The method comprises the administration of an amount of an aspirinate that elevates the level of TGF-beta in said mammal so as to inhibit or reduce-diminution in vessel lumen diameter. Preferably, the levels of active TGF-beta are elevated after administration of the aspirinate.

Preferred agents useful in the practice of the invention are copper aspitinates. Preferably, the effective amount of aspirinate inhibits lipid accumulation, increases plaque stability, decreases lesion formation or development, promotes lesion regression, or any combination thereof. Agents useful in the practice of the method include aspirinate salts such as copper salts of aspirinates, including copper aspirinate itself (copper 2-acetylsalicylate or copper 2-acetoxybenzoate), salicylate salts such as copper salts of salicylates, including copper salicylate (copper 2-hydroxybenzoate), or a compound of formula (I) (see below) including a pharmaceutically acceptable salt thereof, or a combination thereof.

An aspirinate useful in the present invention is a compound of formula (I):

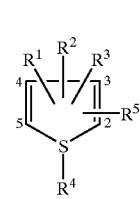

(I)

wherein $R^1$ is hydrogen, halo, nitro, cyano, hydroxy, $CF_3$, $-NR_cR_d$, $-C(=O)OR_e$, $-C(=N)OR_e$, $-OC(=O)OR_e$, $(C_1-C_6)$alkyl or $(C_1-C_6)$alkoxy;

$R^2$ is hydrogen or $-XR_a$;

$R^3$ is $-C(=O)YR_b$, or $-N(R_f)C(=O)R_g-$;

R⁴ is (=O)$_n$; or R⁴ is (C$_1$–C$_6$)alkyl, (C$_1$–C$_6$)alkanoyl or (C$_2$–C$_6$)alkanoyloxy;

R⁵ is hydrogen, —C(=O)OR$_h$ or —C(=O)SR$_h$;

n is 0, 1 or 2;

X is oxygen, —N(R$_i$)—, or sulfur;

Y is oxygen or sulfur;

R$_a$ is (C$_1$–C$_6$)alkanoyl, (C$_1$–C$_6$)alkyl, or hydrogen;

R$_b$ is hydrogen or (C$_1$–C$_3$)alkyl;

R$_c$ and R$_d$ are each independently hydrogen, (C$_1$–C$_4$) alkyl, phenyl, C(=O)OH, C(=O)O(C$_1$–C$_4$)alkyl CH$_2$C(=O)OH, CH$_2$C(=O)O(C$_1$–C$_4$)alkyl, or (C$_1$–C$_4$)alkoxy; or R$_c$ and R$_d$ together with the nitrogen to which they are attached are a 3,4,5, or 6 membered heterocyclic ring; and R$_e$–R$_i$ are independently hydrogen or (C$_1$–C$_6$)alkyl;

a pharmaceutically acceptable salt thereof; or a combination thereof;

provided that R² and R³ are on adjacent positions of the ring to which they are attached, or are on the 2- and 5-positions of the ring; and further provided that when R² is hydrogen; R³ is on the 2- or 5-position of the ring to which it is attached and R⁴ is (C$_1$–C$_4$)alkanoyloxy. Preferably, the compound of formula (I) is not 3-acetoxy-2-carboxythiophene.

Also provided is a method of preventing or treating a mammal having, or at risk of, a vascular indication by administering there to an amount of a first therapeutic agent and an amount of a second therapeutic agent which together are effective to elevate the level of TGF-beta, preferably the level of active TGF-beta, in said mammal. Preferably, the administration inhibits or reduces diminution in vessel lumen diameter. The inhibition or reduction in diminution in vessel lumen diameter preferentially occurs at a site in a vessel where the vascular indication is, or is likely to be, manifested. The invention thus provides for combination therapy, e.g., the administration of one agent that can elevate the level of latent TGF-beta, and another agent that can elevate the level of TGF-beta which is available to bind to, or is capable of binding to, the TGF-beta receptor. This combination therapy can yield a significantly greater cardiovascular efficacy than would be expected from the administration of either agent singly. The therapeutic agents can act in a synergistic, rather than in an additive, manner to elevate TGF-beta levels. The therapeutic agents can be administered simultaneously in a single dosage form simultaneously in individual doses, or sequentially.

A first therapeutic agent useful in this embodiment of the invention includes an aspirinate, e.g., a compound of formula (I). Another preferred first therapeutic agent comprises a compound of formula VI (see below). A preferred second therapeutic agent useful in this embodiment of the invention comprises at least one omega-3 fatty acid, which can be provided, e.g., by dosages of fish oil. Another preferred second therapeutic agent is selected from at least one compound of formula VI. Thus, a compound of formula VI may both elevate latent levels of TGF-beta and elevate the levels of TGF-beta which can bind to the TGF-beta receptors. Preferably, the combination of the therapeutic agents inhibits lipid accumulation, increases plaque stability, decreases lesion formation or development, promotes lesion regression, or any combination thereof.

A compound useful in the present invention is a compound of formula (VI):

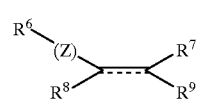

(VI)

wherein

R⁶ is (C$_1$–C$_6$)alkyl, or aryl, optionally substituted by 1, 2, or 3 V;

R⁷ is phenyl, optionally substituted by 1, 2, or 3 V; or R⁷ is (C$_1$–C$_{12}$)alkyl, halo(C$_1$–C$_{12}$)alkyl, (C$_1$–C$_6$) cycloalkyl, (C$_1$–C$_6$)alkylcyclo(C$_1$–C$_6$)alkyl, (C$_1$–C$_6$) cycloalkenyl, or (C$_1$–C$_6$)alkyl(C$_1$–C$_6$)cycloalkenyl;

R⁸ is hydrogen or phenyl, optionally substituted at the 2-position with R$_j$, and optionally substituted by 1, 2, or 3 V;

R⁹ is hydrogen, nitro, halo, aryl, heteroaryl, aryl(C$_1$–C$_3$) alkyl, heteroaryl(C$_1$–C$_3$)alkyl, halo(C$_1$–C$_{12}$)alkyl, cyano(C$_1$–C$_{12}$)alkyl, (C$_1$–C$_4$)alkoxycarbonyl(C$_1$–C$_6$) alkyl, (C$_1$–C$_{12}$)alkyl, (C$_1$–C$_6$)cycloalkyl, (C$_1$–C$_6$) alkylcyclo(C$_1$–C$_6$)alkyl, (C$_1$–C$_6$)cycloalkenyl, or (C$_1$–C$_6$)alkyl(C$_1$C$_6$)cycloalkenyl, wherein any aryl or heteroaryl may optionally be substituted by 1, 2, or 3, V; or R⁹ and R$_j$ together are —CH$_2$CH$_2$—, —S—, —O—N (H)—, —N[(C$_1$–C$_6$)alkyl]—, —OCH$_2$—, —OC [(C$_1$–C$_6$)alkyl]$_2$—, or —CH=CH—;

— — — — is a single bond or is —C(B)(O)—, wherein B and D are each independently hydrogen, (C$_1$–C$_6$)alkyl, or halo;

V is OPO$_3$H$_2$, (C$_1$–C$_6$)alkyl, (C$_1$–C$_6$)alkoxy, mercapto, (C$_1$–C$_4$)alkylthio, halo, trifluoromethyl, pentafluoroethyl, nitro, N(R$_n$)(R$_o$), cyano, trifluoromethoxy, pentafluoroethoxy, benzoyl, hydroxy, —(CH$_2$)$_{0-4}$C(=O)(C$_1$–C$_6$)alkyl, —UC(=O)(C$_1$–C$_6$) alkyl, benzyl, —OSO$_2$(CH$_2$)$_{0-4}$CH$_3$, —U(CH$_2$)$_{1-4}$COOR$_p$, —(CH$_2$)$_{0-4}$COOR$_p$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C (=O)R$_k$, —U(CH2)$_{1-4}$R$_k$, —(CH$_2$)$_{0-4}$R$_k$, or —U(CH$_2$)$_{2-4}$OC(=O)R$_p$; wherein U is O, N(R$_m$), or S;

Z is —(CH$_2$)$_{1-3}$—, O, —OCH$_2$—, —CH$_2$O—, —C(=O) O—, —N(R$_q$)—, C=O, or a covalent bond;

R$_k$ is amino, optionally substituted with one or two (C$_1$–C$_6$)alkyl; or an N-heterocyclic ring optionally containing 1 or 2 additional N(R$_1$), S, or nonperoxide O, wherein R$_1$ is H (C$_1$–C$_6$)alkyl, phenyl, or benzyl;

R$_n$ and R$_o$ are independently hydrogen, (C$_1$–C$_6$)alkyl, phenyl, benzyl, or (C$_1$–C$_6$)alkanoyl; or R$_n$ and R$_o$ together with the nitrogen to which they are attached are a 3, 4, 5, or 6 membered heterocyclic ring;

R$_p$ is H or (C$_1$–C$_6$)alkyl; and

R$_m$ and R$_q$ are independently hydrogen, (C$_1$–C$_6$)alkyl, phenyl, benzyl, or (C$_1$–C$_6$)alkanoyl;

the compound is MER25;

or a pharmaceutically acceptable salt thereof.

As described hereinbelow, the combination of aspirin plus an agent such as fish oil that increases the level of TGF-beta which is capable of binding to the TGF-beta receptors, results in a greater reduction in lesion formation in apoE knockout mice relative to aspirin or fish oil therapy alone. Surprisingly, the combination of aspirin and fish oil, which comprises a plurality of omega-3 fatty acids, exerts a markedly synergistic, rather than an additive, effect. Thus, a combination of an agent that elevates the level of latent TGF-beta, e.g., low doses of aspirin or an aspirinate, with an agent that increases the level of TGF-beta which can bind to its receptor, e.g., at least one omega-3 fatty acid, can be very effective in preventing or treating vascular disease. As used herein, "at least one" omega-3 fatty acid reflects the fact that one of skill in the art would recognize that natural sources of omega-3 fatty acids contain a plurality, about 1 to 30, preferably about 1 to 25, and more preferably about 2 to 20, of omega-3 fatty acids.

Another embodiment of the invention is a method for preventing atherosclerosis in a mammal at risk therefor, or treating atherosclerosis in a mammal, by administering to the mammal an amount of a first therapeutic agent and an amount of a second therapeutic agent effective to maintain or elevate the level of TGF-beta. The first therapeutic agent preferably increases the level of latent TGF-beta, e.g., is aspirin or an aspirinate, or a combination thereof, and the second therapeutic agent increases the level of TGF-beta which is capable of binding to the TGF-beta receptors. Thus, the agents of the invention are administered in a combined amount that prevents or inhibits diminution in vessel lumen diameter at, or near, a site or potential site of atherosclerotic lesion formation or development. A preferred first therapeutic agent comprises aspirin or an aspirinate. A preferred second therapeutic agent comprises at least one omega-3 fatty acid.

The invention also provides a method to inhibit diminution in mammalian vessel lumen diameter. The method comprises administering to a mammal in need of said therapy, an amount of a first therapeutic agent and an amount of a second therapeutic agent effective to maintain or elevate the level of TGF-beta, so as to inhibit or reduce vessel lumen diminution. The inhibition or reduction in diminution in vessel lumen diameter preferentially occurs at a site in a vessel where the diminution is or is likely to be manifested. The first therapeutic agent increases the level of latent TGF-beta, with the proviso that the first therapeutic agent is not aspirin. The first therapeutic agent is preferably an aspirinate. The second therapeutic agent increases the level of TGF-beta which is capable of binding to the TGF-beta receptors.

Also provided is a combination therapy to maintain or elevate TGF-beta levels in a mammal in need of such treatment. The method comprises the administration of an amount of a first therapeutic agent and a second therapeutic agent, wherein said amount is effective to maintain or elevate the level of TGF-beta. The first therapeutic agent increases the level of latent TGF-beta, while the second therapeutic agent increases the level of TGF-beta which is capable of binding to the TGF-beta receptors. A preferred first therapeutic agent comprises aspirin or an aspirinate, while a preferred second therapeutic agent comprises at least one omega-3 fatty acid.

The invention also provides a method to maintain or elevate TGF-beta levels in a mammal in need of such treatment. The method comprises the administration of an amount of an aspirinate effective to maintain or elevate the level of TGF-beta, preferably active TGF-beta, in said mammal.

The invention also provides a method of preventing or treating a mammal having, or preventing in a mammal at risk of, a condition which is associated with a TGF-beta deficiency. Also provided is a method to maintain TGF-beta levels in a mammal. The methods comprise the administration of one or more agents in an amount effective to elevate or maintain the level of TGF-beta in said mammal. The effective amount of the agent or agents may increase the level of latent TGF-beta or the level of TGF-beta which is capable of binding to the TGF-beta receptors. Agents useful to increase the level of latent TGF-beta include, but are not limited to, idoxifene, toremifene, raloxifene, droloxifene, ethynyl estradiol, diethylstibestrol, 1,25 dihydroxy-vitamin D3, retinoic acid and ligand pharmaceutical analogs thereof (Mukherjee et al. *Nature*, 1997, 386: 407–410), dexamethasone, progesterone, thyroid hormone analogues (e.g. sodium liothyronine and sodium levothyroxine), hexamethylene bisacetamide, 4-hydroxyquinazoline, coumarin and benzocaine.

Agents useful to increase the level of TGF-beta which is capable of binding to the TGF-beta receptors include agents that cause the release of TGF-beta from matrix components or plasma proteins, e.g., agents such as heparin sugar analogs and betaglycan proteoglycan chains, or cause the release of TGF-beta from lipoprotein complexes, e.g., agents such as vitamin E, simvastatin, VLDL-lowering agents, Apo-AII-lowering agents, and ApoAI-stimulating agents. Other agents useful to increase the level of TGF-beta which is capable of binding to the TGF-beta receptors include agents that cause an increase in the conversion of the latent form of TGF-beta to the active form of TGF-beta, e.g., hydrocortisone, dexamethasone, compounds of formula VI, vitamin D3, retinoic acid, simvastatin and thrombospondin.

Also provided is a kit comprising packing material enclosing, separately packaged, at least one device adapted for the delivery of a unit dosage form of a therapeutic agent and at least one unit dosage form comprising an amount of at least one of the therapeutic agents of the invention effective to accomplish at least one of the therapeutic results described herein when administered locally or systemically, as well as instruction means for its use, in accord with the present methods. As used herein, a "device adapted for delivery" of a therapeutic agent includes, but is not limited to, a catheter, a stent, a stet, a shunt, a synthetic graft, and the like.

Also provided is a kit comprising packing material enclosing, separately packaged, at least one device adapted for the delivery of a therapeutic agent to a site in the lumen of a mammalian vessel and at least one unit dosage form of a first therapeutic agent and one unit dosage form of a second therapeutic agent effective to accomplish at least one of the therapeutic results described herein when administered locally or systemically, as well as instruction means for its use, in accord with the present methods.

Further provided is a pharmaceutical composition comprising a) at least one aspirinate, and b) at least one omega-3 fatty acid, wherein components (a) and (b) are present in a combined amount effective to maintain or increase TGF-beta levels, preferably at or near a site, or potential site, of atherosclerotic lesion formation or development.

The invention also provides a pharmaceutical composition comprising (a) an amount of a first agent effective to elevate the level of latent TGF-beta; and (b) an amount of a second agent effective to increase the level of TGF-beta which is capable of binding to the TGF-beta receptors.

The invention also provides a pharmaceutical composition comprising a) an aspirinate, such as copper 2-acetylsalicylate or a compound of formula (I), and b) a compound of formula (VI), wherein components (a) and (b) are present in a combined amount effective to maintain or increase TGF-beta levels, preferably at or near a site, or potential site, of atherosclerotic lesion formation or development.

Also provided are novel compounds of formula (I), (II), (III), (IV), (V), (VI), (VII), or (VIII) or pharmaceutically acceptable salts thereof, and pharmaceutical compositions comprising a novel compound of formula (I), (II), (III), (IV), (V), (VI), (VII), or (VIII) as described herein or a pharmaceutically acceptable salt thereof, which are useful alone, or in combination, to elevate the level of TGF-beta in a mammal.

The invention also provides a therapeutic method. The method comprises identifying a patient exhibiting a decreased level of active TGF-beta and afflicted with a pathology associated with said decreased level. The patient so identified can be treated with an agent that elevates the levels of active TGF-beta so as to alleviate at least one of the symptoms of said pathology.

The invention also provides a method comprising determining endothelial cell activation in a mammal by detecting immunoglobulins that specifically bind to a TGF-β Type II receptor or a portion thereof.

The invention also provides a method comprising diagnosing or monitoring a disease characterized by endothelial cell activation (e.g. atherosclerosis) in a mammal by detecting immunoglobulins that specifically bind to a TGF-β Type II receptor or a portion thereof.

The invention also provides a method comprising detecting mammalian cells having TGF-β Type II receptors, by combining the cells with a capture moiety that binds TGF-β type II receptors or a portion thereof, forming a capture complex; and detecting or determining the amount of the capture complex.

The invention also provides a kit comprising packaging material containing: a) a capture moiety comprising the extracellular domain of the TGF-β Type II receptor; and b) a detection moiety capable of binding to an immunoglobulin. The invention also provides a kit comprising packaging material containing: a) a capture moiety that binds to the extracellular domain of the TGF-β Type II receptor; and b) a detection moiety capable of binding to an immunoglobulin.

DETAILED DESCRIPTION OF THE INVENTION

Administration of a Therapeutic Agent

Figure 1:
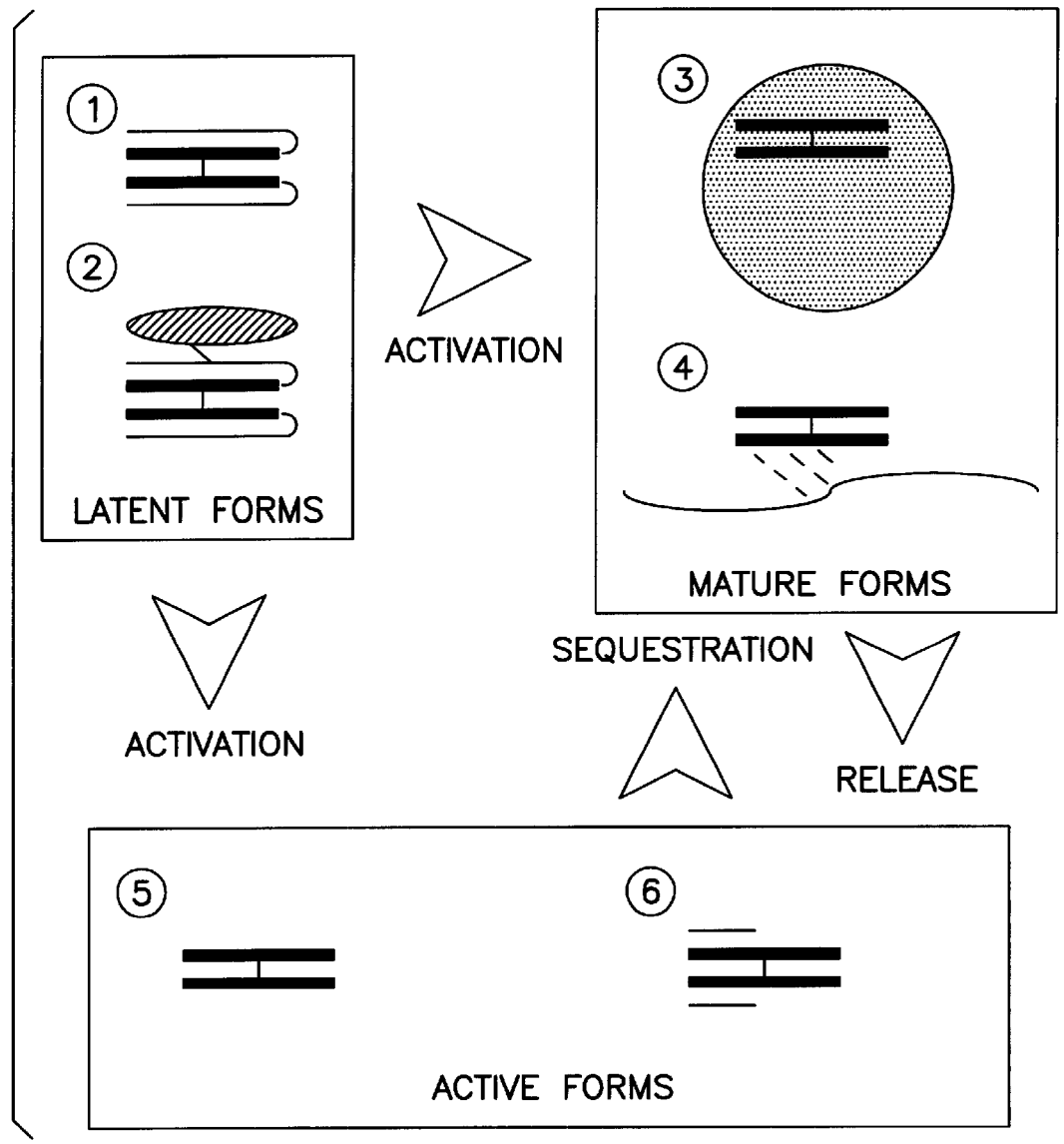
FIG. 1 is a schematic depicting the different forms of TGF-beta. TGF-beta is produced as a small latent complex (1) which is associated with the propeptide region termed LAP (thin black lines). During, or after secretion, of the small latent complex, additional proteins (hatched oval), e.g., LTBP-1, bind to the small latent complex to form the large latent complex (2). Latent complexes can be converted to the active form of TGF-beta, e.g., the 25 kD dimer (5) or the 25 kD dimer which is associated with a peptide of LAP (6). Examples of mature forms of TGF-beta are TGF-beta associated with lipoprotein (stippled oval) (3) or TGF-beta associated with a matrix protein (helical fiber) (4), e.g., fibrillin.

The invention provides a method of treating a mammal having, or at risk of, a indication (e.g. a vascular indication) associated with a TGF-beta deficiency. The invention also provides a method to maintain elevated levels of TGF-beta in a mammal which is not imminently at risk of, or does not have, an indication associated with a deficiency in TGF-beta levels. The methods comprise the administration of at least one therapeutic agent that elevates the level of TGF-beta in said mammal. Preferably, the agent elevates the level of latent TGF-beta, for example by causing an increase in the level of TGF-beta mRNA, causing an increase in the translational efficiency of TGF-beta mRNA, or by causing an increase in the secretion of latent TGF-beta.

Another preferred embodiment is an agent that increases the level of TGF-beta which is capable of binding to the TGF-beta receptors, for example by causing the release of TGF-beta from matrix components of plasma proteins, by causing the release of TGF-beta from lipoprotein complexes, or by causing an increase in the conversion of the latent to the active form of TGF-beta.

Yet another embodiment of the invention employs the systemic administration of a therapeutic agent, e.g., a compound of formula (I) including a pharmaceutically acceptable salt thereof, or a combination thereof, in an amount effective to inhibit or reduce the diminution in vessel lumen diameter in a diseased, e.g., atherosclerotic, or traumatized, e.g., due to stent placement, vessel.

Systemic administration of a therapeutic agent can also be employed to treat or prevent pre-atherosclerotic conditions, e.g., in patients at a high risk of developing atherosclerosis or exhibiting signs of hypertension resulting from atherosclerotic changes in vessels or vessel stenosis due to hypertrophy of the vessel wall. Preferably, the therapeutic agent is administered orally. It is also preferred that the agent useful in the practice of the invention is administered continually over a preselected period of time or administered in a series of spaced doses, i.e., intermittently, for a period of time as a preventative measure.

For the prevention of vessel lumen diminution associated with procedural vascular trauma, the therapeutic agent can be administered before, during or after the procedure, or any combination thereof. For example, for the prevention of restenosis, a series of spaced doses of the therapeutic agent, optionally, in sustained release dosage form, is preferably administered before, during and/or after the traumatic procedure (e.g., angioplasty). The dose may also be delivered locally, via a catheter introduced into the, afflicted vessel during the procedure. After the traumatic procedure is conducted, a series of follow-up doses can be administered systemically over time, preferably in a sustained release dosage form, for a time sufficient to substantially reduce the risk of, or to prevent, restenosis. A preferred therapeutic protocol duration for this purpose involves administration from about 3 to about 26 weeks after angioplasty.

Combination Therapies

The invention provides combination therapies, i.e., the administration of at least two therapeutic agents which together are effective to maintain or elevate TGF-beta levels in a mammal. Accordingly, the invention provides a method of preventing or treating a mammal having, or at risk of, an indication which is associated with a TGF-beta deficiency, comprising administering an amount of a first agent effective to elevate the level of latent TGF-beta and an amount of a second agent effective to increase the level of TGF-beta which is capable of binding to the TGF-beta receptors, wherein said amounts are effective to increase the TGF-beta levels in said mammal.

The invention also provides a method comprising administering an amount of a combination of aspirin or an aspirinate and at least one omega-3 fatty acid, wherein said amount is effective to maintain or elevate the level of TGF-beta in said mammal.

The invention also provides a method of preventing or treating a mammal having, or at risk of, a vascular indication which is associated with a TGF-beta deficiency, comprising administering an effective amount of a combination of an aspirinate and at least one omega-3 fatty acid, wherein said amount is effective to increase the level of TGF-beta so as to inhibit or reduce vessel lumen diameter diminution. The invention also provides for the administration of at least two therapeutic agents which together are effective to elevate the levels of TGF-beta in a mammal so as to inhibit or reduce vessel lumen diameter diminution. The invention also provides combination therapies to maintain elevated levels of TGF-beta in a mammal which is not imminently at risk of, or does not have, a vascular indication associated with a deficiency in TGF-beta levels. The therapeutic agents can be selected to act in a synergistic, rather than in an additive, manner to elevate TGF-beta levels. The therapeutic agents can be administered simultaneously as a single dose, simultaneously in individual doses, or sequentially.

One embodiment of the invention employs the systemic administration of a first therapeutic agent, e.g., an aspirinate such as copper 2-acetylsalicylate, a compound of formula (I), or a combination thereof, in combination with a second therapeutic agent, e.g., a compound of formula (VI), in an amount effective to increase TGF-beta levels. The increase in TGF-beta levels, in turn, inhibits or reduces the diminution in vessel lumen diameter in a diseased, e.g., atherosclerotic, or traumatized, e.g., due to stent placement, vessel. The increase in TGF-beta levels can also inhibit atherosclerotic lesion formation or development, increase plaque stability and/or promote lesion regression.

Systemic administration of the therapeutic agents can also be employed to treat or prevent pre-atherosclerotic conditions, e.g., in patients at a high risk of developing atherosclerosis or exhibiting signs of hypertension resulting from atherosclerotic changes in vessels or vessel stenosis due to hypertrophy of the vessel wall. Preferably, at least one of the therapeutic agents is administered orally.

It is also preferred that the agents useful in the practice of the invention are administered continually over a preselected period of time or administered in a series of spaced doses, i.e., intermittently, for a period of time as a preventative measure.

A preferred embodiment of the invention provides a method for the treatment or prevention of atherosclerosis, wherein an omega-3 fatty acid in combination with aspirin or an aspirinate, is administered so as to inhibit (block or reduce) atherosclerotic lesion formation or development, e.g., so as to inhibit lipid accumulation, increase plaque stability or promote lesion regression. In this embodiment of the invention, it is preferred that the therapeutic agents are orally administered. Preferably, copper aspirinate and an omega-3 fatty acid are orally administered. A preferred source of the omega-3 fatty acid is fish oil.

Another preferred embodiment of the invention provides a method for the treatment or prevention of atherosclerosis, wherein at least two therapeutic agents of the invention are administered in combination so as to inhibit (block or reduce) atherosclerotic lesion formation or development, e.g., so as to inhibit lipid accumulation, increase plaque stability or promote lesion regression. In this embodiment of the invention, it is preferred that at least one of the therapeutic agents is orally administered.

Combination therapies are also useful to treat vessels traumatized by interventional procedures. For example, for the prevention of restenosis, a series of spaced doses of at least two of the present therapeutic agents, optionally, in sustained release dosage form, are preferably administered before and after the traumatic procedure (e.g., angioplasty). The dose may also be delivered locally, via a catheter introduced into the afflicted vessel during the procedure. After the procedure is conducted, a series of follow-up doses of, optionally, both agents, can be administered systemically, preferably in a sustained release dosage form, for a time sufficient to substantially reduce the risk of, or to prevent, restenosis. As noted above, a preferred duration for this purpose is from about 3 to about 26 weeks after angioplasty.

Kits Comprising a Delivery Device and the Therapeutic Agents of the Invention

The invention provides a kit comprising packing material enclosing, separately packaged, at least one device adapted for the local or systemic delivery of therapeutic agent, e.g., a catheter, a valve, a stent, a stet, a shunt or a synthetic graft, and at least one unit dosage form, as well as instruction means for their use, in accord with the present methods. A valve, stent or shunt useful in the methods of the invention can comprise a biodegradable coating or porous non-biodegradable coating, having dispersed therein a therapeutic agent of the invention, preferably a sustained release dosage form of the therapeutic agent. The unit dosage form comprises an amount of at least one of the present therapeutic agents effective to accomplish the therapeutic results described herein when delivered locally and/or systemically. A preferred embodiment of the invention is a kit comprising a catheter adapted for the local delivery of at least one therapeutic agent to a site in the lumen of a mammalian vessel, along with instruction means directing its use in accord with the present invention. Preferably, the therapeutic agent comprises a copper aspirinate.

The invention provides a kit comprising packing material enclosing, separately packaged, at least one device adapted for the local or systemic delivery of a therapeutic agent, e.g., a catheter, a valve, a stent, a stet, a shunt or a synthetic graft, and at least one unit dosage form which may comprise an amount of at least two of the present therapeutic agents effective to accomplish the therapeutic results described herein.

Another embodiment of the invention is a kit comprising a catheter adapted for the local delivery of at least two therapeutic agents, a unit dosage of a first therapeutic agent, and a unit dosage of a second therapeutic agent, along with instruction means directing their use in accord with the present invention. The unit dosage forms of the first and second agents may be introduced via discrete lumens of a catheter, or mixed together prior to introduction into a single lumen of a catheter. If the unit dosage forms are introduced into discrete lumens of a catheter, the delivery of the agents to the vessel can occur simultaneously or sequentially. Moreover, a single lumen catheter may be employed to deliver a unit dosage form of one agent, followed by the reloading of the lumen with another agent and delivery of the other agent to the lumen of the vessel. Either or both unit dosages can act to reduce the diminution in vessel lumen diameter at the target site.

Alternatively, a unit dosage of one of the therapeutic agents may be administered locally, e.g., via catheter, while a unit dosage of another therapeutic agent is administered systemically, e.g., via oral administration. It is also envisioned that the kit of the invention comprises a non-catheter delivery device, e.g., a valve, stet, stent or shunt, for systemic or local delivery of a compound of formula (I–VI). A valve, stent or shunt useful in the methods of the invention can comprise a biodegradable coating or porous non-biodegradable coating, having dispersed therein one or more therapeutic agents of the invention, preferably a sustained release dosage form of the therapeutic agent.

Definitions

The following definitions apply.

"Abnormal or pathological or inappropriate" with respect to an activity or proliferation means division, growth or migration of normal cells, but not cancerous or neoplastic cells, occurring more rapidly or to a significantly greater extent than typically occurs in a normally functioning cell of the same type, or in lesions not found in healthy tissues.

"Agents which activate the latent form of TGF-beta to the active form" include, but are not limited to, moieties such as hydrocortisone, dexamethasone, a compound of formula (VI) (such as tamoxifen), Vitamin D3 and retinoic acid (vitamin A); plasmin stimulators, e.g., Lp(a) lowering agents such as tamoxifen, PAI-1 lowering agents (e.g., simvastatin and other VLDL-lowering agents), and agents which exhibit increased tPA activity (e.g., retinoids, such as Vitamin D3); and agents which exhibit non-plasmin mediated activation (e.g., thrombospondin and Vitamin D3).

"Agents which increase the level of TGF-beta which is capable of binding to the TGF-beta receptors" includes moieties capable of activating the latent form of TGF-beta to the active form thereof, moieties which release TGF-beta from complexes of matrix components and TGF-beta, complexes of plasma proteins and TGF-beta and/or complexes of lipoproteins and TGF-beta. A number of compounds of formula (VI) can increase the level of TGF-beta which is capable of binding to the TGF-beta receptors.

"Agents which release TGF-beta from the extracellular matrix" include moieties such as heparin, heparin sugar analogs (e.g., fucoidin) and betaglycan proteoglycan chains.

"Agents which release TGF-beta from lipoprotein sequestration" include moieties such as Vitamin E and its salts (e.g., Vitamin E succinate), fish oil, simvastatin, other VLDL-lowering agents, apo-AII-lowering agents, and apoAI-stimulating agents.

"ApoAII-lowering agent" includes an agent which decreases the synthesis of apoAII, decreases the post-translational insertion of apoAII into nascent HDL particles or stimulates the clearance of apoAII-containing particles, e.g., by immunoapheresis of plasma with anti-apoAII antibodies.

"ApoAI-stimulating agent" includes an agent which stimulates the synthesis of apoAI, stimulates HDL production or extends the half-life of apoAI-HDL particles. For example, estrogen or estrogen agonists, or analogs and derivatives thereof, an agonist of hepatic nuclear factor (HNF) 3 or 4, or an agonist of the retinoid receptor, may increase apoAI transcription.

"Aspirinate" refers generally to aspirin derivatives and analogs, including pharmaceutically acceptable salts thereof, with the exception that aspirin itself is not included within the term "aspirinate". The term includes, but is not limited to, 3,5-diisopropyl salicylic acid, salicylic acid, 3,5-di(tertiarybutyl)salicylic acid, adamantylsalicylic acid, 3,5 dibromoacetylsalicylic acid, 3,5-diiodoacetylsalicylic acid, 4-(tertiarybutyl)salicylic acid, 4-nitrosalicylic acid, 4-aminosalicylic acid, 4-acetylaminosalicylic acid, 5-chlorosalicylic acid, 3,5-dichlorosalicylic acid and salts thereof, and compounds of formula (I) and their salts. Preferably, the aspirinate is provided in essentially pure form, most preferably in a unit dosage form, in combination with one or more pharmaceutically acceptable carriers, including vehicles and/or excipients. Preferably, the aspirinate is in a form suitable for oral administration, and more preferably the aspirinate is in combination with a liquid vehicle.

"At least one", when used with respect to omega-3 fatty acids would be recognized in the art as indicating that a plurality, about 1 to 30, preferably about 1 to 25, more preferably about 2 to 20, of omega-3 fatty acids are often present in natural sources of these compounds.

"Autoimmune disease" means a disease which is characterized by the presence of autoreactive T lymphocytes resulting in pathological inflammation and subsequent damage or destruction of the target tissue. Such diseases include, but are not limited to, rheumatoid arthritis, multiple sclerosis and late-onset diabetes.

"Betaglycan proteoglycan chain" includes all or a portion of any of the proteoglycan that comprise the class of molecules termed type-III TGF-beta receptor, e.g., CD105, endoglin or betaglycan. For example, a portion of the proteoglycan may include all or a portion of the protein moiety of the proteoglycan, all or a portion of the polysaccharide moiety of the proteoglycan, all or a portion of the protein moiety and a portion of the polysaccharide moiety, all or a portion of the polysaccharide moiety and a portion of the protein moiety, or a portion of the protein moiety and a portion of the polysaccharide moiety. Preferably, the betaglycan proteoglycan chain has a similar or greater affinity for TGF-beta relative to the affinity of native betaglycan for TGF-beta.

"Bioavailable" TGF-beta means TGF-beta which is in a form capable of binding to the TGF-beta receptors, i.e., eliciting a biological effect. For example, TGF-beta which is in a complex with matrix components or plasma proteins, or lipoproteins, is generally not "bioavailable" or has reduced bioavailability relative to TGF-beta which is not complexed with matrix components, plasma proteins, or lipoproteins.

"Cholesterol lowering agents" include agents which are useful for lowering serum cholesterol such as for example bile acid sequestering resins (e.g. colestipol hydrochloride or cholestyramine), fibric acid derivatives (e.g. clofibrate, fenofibrate, or gemfibrozil), thiazolidenediones (e.g. troglitazone), or HMG-CoA reductase inhibitors (e.g. fluvastatin sodium, lovastatin, pravastatin sodium, or simvastatin), as well as nicotinic acid, niacin, or probucol.

"Elevated" TGF-beta levels means that the TGF-beta levels in vivo are greater after administration of the therapeutic agent than before administration. Thus, for example, active TGF-beta levels may be increased after administration, but may be less than normal levels, similar to normal levels or greater than normal levels of TGF-beta in vivo.

"Heparin sugar analogs" includes any sulfated polysaccharide which is a component of heparin sulfate proteoglycan, or a sulfated polysaccharide having a structure similar to the polysaccharide chain of heparin sulphate proteoglycan.

"NFkB" means any of the family of transcription factor complexes which have as at least one of their components the subunits known as p65 (RelA), p50, p52, c-rel, p68 (RelB) as well as the complexes which have as at least one of their components the endogenous inhibitors of NMS activity, known as IkB-alpha, MAD3, pp40, IkB-beta and IkB-gamma as well as their functional equivalents, analogs and derivatives thereof.

"NFkB activity" means activation of genes associated with the inflammatory state resulting from direct binding of an NFkB transcription factor complex to DNA elements, including, but not limited to, the kB element in the immunoglobulin kappa light chain gene. NFkB complex is normally retained in the cytoplasm by interaction with its endogenous inhibitor IkB. NFkB activity must be preceded by localization of the NFkB complex to the nucleus. However, translocation of the NFkB complex to the nucleus does not constitute NFkB activity unless transcription from genes associated with the inflammatory state is stimulated.

"Non-vascular indication" means diseases and conditions which are associated with TGF-beta deficiency, other than those diseases and conditions defined herein as vascular indications. Non-vascular indications include, but is not limited to cancer, Marfan's syndrome, Parkinson's disease, fibrosis, Alzheimer's disease, senile dementia, osteoporosis, diseases associated with inflammation, such as rheumatoid arthritis, multiple sclerosis and lupus erythematosus, as well as other auto-immune disorders. Non-vascular indications also include the promotion of wound healing and the lowering of serum cholesterol levels.

"Omega-3 fatty acid" includes synthetic or naturally occurring sources of omega-3 fatty acids, such as fish oil, e.g., cod liver oil, walnuts and walnut oil, wheat germ oil, rapeseed oil, soybean lecithin, soybeans, tofu, common beans, butternuts, seaweed and flax seed oil. The omega-3 fatty acids include ($C_{16}$–$C_{24}$) alkanoic acids comprising 5–7 double bonds, wherein the last double bond is located between the third and fourth carbon atom from the methyl end of the fatty acid chain. These fatty acids have been proposed to yield significant cardiovascular protection (Burr et al., *Lancet,* 221, 757 (1989)). Omega-3 fatty acids include 5,8, 11, 14, 17-eicosapentaenoic acid and docosahexaenoic acid. See *The Merck Index* (11th ed. 1989) at entry 3495, and references cited therein.

"Pathological inflammation" means an increase in the recruitment and activation of immune cells, or residence and activation of immune cells for a longer period of time, in a particular tissue or tissues in an individual relative to an individual not at risk or, or afflicted with, an autoimmune disease. For the purposes of this description, the prototypical cells upon which the effects of ER/NFkB modulators are felt, are cells of the immune system, including but limited to, autoreactive T lymphocytes, alloreactive T lymphocytes, B lymphocytes, monocytes, tissue macrophages, neutrophils, eosinophils and other leukocytes. However, the usefulness of ER/NFkB modulators is not limited to their effects on immune cells in the treatment of autoimmune diseases. Effects on vascular endothelial cells and on the cells composing the target tissue may also contribute to the anti-inflammatory effect of the ER/NFkB modulators by reducing recruitment of leukocytes as well as activation of resident immune cells.

"PAI-1 lowering agent" includes an agent which increases insulin sensitivity, decreases production of PAI-1 or decreases the activity of PAI-1 as an inhibitor of plasminogen activators or of plasmin. PAI-1 lowering agent includes the thiazolidenediones (e.g. troglitazone).

"Plasmin stimulator" includes an agent which increases the activity of plasmin, e.g., a PAI-1 inhibitor, tissue plasminogen activator (tPA) or streptokinase, preferably without disrupting normal hemostasis. A plasmin stimulator may increase plasmin levels by catalyzing the conversion of the latent form of plasmin, i.e., plasminogen, to the active form, or stimulate the activity of the plasmin enzyme, e.g., generally or with regard to a specific substrate, e.g., TGF-beta.

"Procedural vascular trauma" includes the effects of surgical/medical-mechanical interventions into mammalian vasculature, but does not include vascular trauma due to the organic vascular pathologies listed hereinabove, or to unintended traumas, such as due to an accident. Thus, procedural vascular traumas within the scope of the present treatment method include (1) organ grafting or transplantation, such as transplantation and grafting of heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, or indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PTFE hemodialysis shunt used for arteriovenous communications; and (6) placement of an intravascular stent, which may be metallic, plastic or a biodegradable polymer. See U.S. patent application Ser. No. 08/389, 712, filed Feb. 15, 1995, which is incorporated by reference herein. For a general discussion of implantable devices and biomaterials from which they can be formed, see H. Kambic et al., "Biomaterials in Artificial Organs", *Chem. Eng. News,*

30 (Apr. 14, 1986), the disclosure of which is incorporated by reference herein.

"Proliferation," means an increase in cell number, i.e., by mitosis of the cells.

"Sustained release" means a dosage form designed to release a therapeutic agent therefrom for a time period ranging from at least about 0.0005 to about 21, and more preferably at least about 1–3 to about 120, days. Release over a longer time period is also contemplated as "sustained release" in the context of the dosage form of the present invention. It is contemplated that sustained release dosage forms for systemic administration as well as local administration can be employed in the practice of the invention. Examples of sustained release dosage forms are disclosed in co-pending application Ser. No. 08/478,936, filed Jun. 7, 1995, the disclosure of which is incorporated by reference herein.

"Tamoxifen" includes trans-2-[4-(1,2-diphenyl-1-butenyl)phenoxy]-N,N-dimethylethylamine, and the pharmaceutically acceptable salts thereof, which are capable of enhancing the level of active TGF-beta, e.g., by increasing the level of latent TGF-beta or by increasing the level of TGF-beta which is capable of binding to the TGF-beta receptors.

"TGF-beta" includes transforming growth factor-beta as well as functional equivalents, derivatives and analogs thereof, e.g., TGF-$\beta_1$, TGF-$\beta_2$, and TGF-$\beta_3$. The TGF-beta isoforms are a family of multifunctional, disulfide-linked dimeric polypeptides that affect activity, proliferation and differentiation of various cells types. A functional equivalent of TGF-$\beta$ can include agents that bind to the TGF-$\beta$ receptor, e.g. a receptor agonist or antagonist or a neutral binding agent, and/or which induces the same biological response as TGF-$\beta$.

"Vascular indication" includes, but is not limited to, a cardiovascular disease, e.g., atherosclerosis, thrombosis, myocardial infarction, and stroke, or a cardiovascular condition, e.g., vessels subjected to trauma associated with interventional procedures ("procedural vascular trauma"), such as restenosis following angioplasty, placement of a shunt, stet, stent, synthetic or natural excision grafts, indwelling catheter, valve or other implantable devices. Also within the scope of the term "vascular indication" is non-coronary vessel disease, such as arteriolosclerosis, small vessel disease, nephropathy, greater than normal levels of serum cholesterol, asthma, hypertension, emphysema and chronic obstructive pulmonary disease. "Vascular indication" does not include cancer, including smooth muscle cell carcinomas or neoplasms, or idiopathic symptoms such as forms of angina that are not attributable to vascular diseases.

Small vessel disease includes, but is not limited to, vascular insufficiency in the limbs, peripheral neuropathy and retinopathy, e.g., diabetic retinopathy. "VLDL-lowering agent" includes an agent which decreases the hepatic synthesis of triglyceride-rich lipoproteins or increases the catabolism of triglyceride-rich lipoproteins, e.g., fibrates such as gemfibrozil, or the statins, increases the expression of the apoE-mediated clearance pathway, or improves insulin sensitivity in diabetics, e.g., the thiazolidene diones.

Additionally, as used herein, "agents which increase the level of latent TGF-beta" include moieties capable of stimulating the production of TGF-beta protein (generally the latent form thereof). The mechanism leading to the increase in TGF-beta protein can include, but is not limited to, up-regulation of mRNA production (transcription), increased translational efficiency of the mRNA, or increased secretion of the latent TGF-beta complex. Agents which increase the production of TGF-beta protein include, but are not limited to, moieties which affect the nuclear hormone receptor pathway (e.g., tamoxifen, idoxifene, toremifene, raloxifene, droloxifene and other anti-estrogen analogues of tamoxifen, ethynyl estradiol, diethylstilbestrol, other synthetic estrogen agonists and compounds disclosed in U.S. Pat. Nos. 4,442,119, 5,015,666, 5,098,903, 5,324,736), 1,25 dihydroxy-vitamin D3, allopurinol, EB 1089, MC 903, KH1060, retinoic acid/vitamin A and ligand pharmaceutical analogs thereof (Mukherjee et al. Nature, 1997, 386: 407–410), dexamethasone (e.g., glucocorticoid agonist analogues), progesterone (e.g., gestodene and synthetic progestins), and thyroid hormone analogues (e.g. sodium liothyronine and sodium levothyroxine), (e.g. 12,14 dideoxy-prostaglandin J2; $\Delta$12,14-PGJ2).

Other agents which increase the level of TGF-beta include aspirin, aspirinates such as copper aspirinate, and red wine extract (see Example IV). Red wine extract is a fraction or concentrate derived from red wine that is substantially enriched in copper aspirinate, hexamethylene bisacetamide, 4-hydroxyquinazoline, coumarin and benzocaine.

The term "halo" includes fluoro, chloro, bromo, or iodo. The terms alkyl, and alkoxy denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is hydrogen, O, ($C_1$–$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed for radicals, substituents, and ranges, are for illustration only and they do not exclude other defined values or other values within defined ranges for the radicals and substituents.

Specifically, ($C_1$–$C_3$)alkyl can be methyl, ethyl, propyl, or isopropyl; ($C_1$–$C_4$)alkyl can be methyl, ethyl, propyl, isopropyl, butyl, iso-butyl or sec-butyl; ($C_1$–$C_6$)alkyl can be methyl, ethyl, propyl, isopropyl, butyl, iso-butyl, sec-butyl, pentyl, isopentyl, neopentyl, or hexyl; ($C_1$–$C_{12}$)alkyl can be methyl, ethyl, propyl, isopropyl, butyl, iso-butyl, sec-butyl, pentyl, isopentyl, neo-pentyl, hexyl, 2-hexyl, 3-hexyl, heptyl, 2-heptyl, 3-heptyl, octyl, 2-octyl, 3-octyl, 4-octyl, nonyl, 2-nonyl, 3-nonyl, 4-nonyl, decyl, 2-decyl, 3-decyl, 4-decyl, 5-decyl, undecyl, 2-undecyl, 3-undecyl, 4-undecyl, 5-undecyl, dodecyl, 2-dodecyl, 3-dodecyl, 4-dodecyl, 5-dodecyl, or 6-dodecyl; $(C_3-C_6)$cycloalkyl can be cyclopropyl, cyclobutyl, cyclopentyl, or cyclohexyl; $(C_3-C_6)$cycloalkenyl can be cyclopropenyl, cyclobutenyl, cyclopentenyl, cyclopentadienyl cyclohexenyl, or cyclohexadienyl; $(C_1-C_6)$alkoxy can be methoxy, ethoxy, propoxy, isopropoxy, butoxy, iso-butoxy, sec-butoxy, pentoxy, neopentoxy, isopentoxy, or hexoxy; $(C_1-C_6)$alkanoyl can be acetyl, propanoyl or butanoyl; $(C_2-C_6)$alkanoyloxy can be acetoxy, propanoyloxy or butanoyloxy; halo$(C_1-C_{12})$alkyl can be fluoromethyl, difluoromethyl, trifluoromethyl, fluoroethyl, difluoroethyl, trifluoroethyl, perfluoroethyl, fluoropropyl, difluoropropyl, tifluoropropyl, fluorobutyl, difluorobutyl, trifluorobutyl, fluoropentyl, difluoropentyl, trifluoropentyl, fluorohexyl, difluorohexyl, trifluorohexyl, chloroethyl, dichloroethyl, trichloroethyl, perchloroethyl, chloropropyl, dichloropropyl, trichloropropyl, chlorobutyl, dichlorobutyl, trichlorobutyl, chloropentyl, dichloropentyl, trichloropentyl, chlorohexyl, dichlorohexyl, trichlorohexyl, bromoethyl, dibromoethyl, tribromoethyl, perbromoethyl, bromopropyl, dibromopropyl, tribromopropyl, bromobutyl, dibromobutyl, tribromobutyl, bromopentyl, dibromopentyl, tribromopentyl, bromohexyl, dibromohexyl, tribromohexyl, iodoethyl, iodopropyl, iodobutyl, iodopentyl, iodohexyl, haloheptyl, dihaloheptyl, trihaloheptyl, halooctyl, dihalooctyl, trihalooctyl, halononyl, dihalononyl, trihalononyl, halodecyl, dihalodecyl, tihalodecyl, haloundecyl, dihaloundecyl, trihaloundecyl, halododecyl, dihalododecyl, or triododecyl.

Likewise, aryl can be phenyl, indenyl, or naphthyl; heteroaryl can be furyl, imidazolyl, tetrazolyl, pyridyl, (or its N-oxide), thienyl, pyrimidinyl (or its N-oxide), indolyl, or quinolyl (or its N-oxide); and aryl $(C_1-C_3)$alkyl can be benzyl, indenylmethyl, naphthylmethyl, phenethyl, indenylethyl, naphthylethyl, phenylpropyl, indenylpropyl, or naphthylpropyl: and heteroaryl $(C_1-C_3)$alkyl can be furylmethyl, imidazolylmethyl, tetrazolylmethyl, pyridylmethyl (or its N-oxide), thienylmethyl, pyrimidinylmethyl (or its N-oxide), indolylmethyl, quinolylmethyl, furylethyl, imidazolylethyl, tetrazolylethyl, pyridylethyl, (or its N-oxide), thienylethyl, pyrimidinylethyl (or its N-oxide), indolylethyl, quinolylethyl, furylpropyl, imidazolylpropyl, tetrazolylpropyl, pyridylpropyl, (or its N-oxide), thienylpropyl, pyrimidinylpropyl (or its N-oxide), indolylpropyl, or quinolylpropyl.

More specifically, $(C_1-C_3)$alkyl can be methyl, ethyl, or propyl; $(C_1-C_4)$alkyl can be methyl, ethyl, propyl, or butyl; $(C_1-C_6)$alkyl can be methyl, ethyl, propyl, isopropyl, butyl, iso-butyl, pentyl, or hexyl; $(C_1-C_{12})$alkyl can be methyl, ethyl, propyl, isopropyl, butyl, iso-butyl, sec-butyl, pentyl, hexyl, heptyl, or octyl; $(C_3-C_6)$cycloalkyl can be cyclopentyl, or cyclohexyl; $(C_3-C_6)$cycloalkenyl can be 2-cyclopentenyl, 3-cyclopentenyl, 2-cyclohexenyl, or 3-cyclohexenyl; $(C_1-C_6)$alkoxy can be methoxy, ethoxy, or propoxy; $(C_1-C_6)$alkanoyl can be acetyl; $(C_2-C_6)$alkanoyloxy can be acetoxy; halo$(C_1-C_{12})$alkyl can be fluoromethyl, difluoromethyl, trifluoromethyl, trifluoroethyl, fluoropropyl, trifluoropropyl, fluorobutyl, trifluorobutyl, fluoropentyl, trifluoropentyl, fluorohexyl, trifluorohexyl, chloroethyl, chloropropyl, chlorobutyl, bromoethyl, bromopropyl, bromobutyl, iodoethyl, iodopropyl, iodobutyl; aryl can be phenyl, heteroaryl can be furyl, imidazolyl, pyridyl (or its N-oxide), or thienyl; aryl $(C_1-C_3)$alkyl can be benzyl or phenethyl; and heteroaryl $(C_1-C_3)$alkyl can be furylmethyl, imidazolylmethyl, pyridylmethyl (or its N-oxide), or thienylmethyl.

Compounds of Formula (I) Within the Scope of the Invention

A specific aspirinate useful in the present invention is a compound of formula (I):

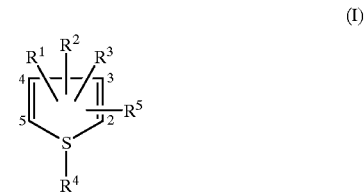

(I)

wherein $R^1$ is hydrogen, halo, nitro, cyano, hydroxy, $CF_3$, $-NR_cR_d$, $-C(=O)OR_e$, $-OC(=O)OR_e$, $-C(=N)OR_e$, $(C_1-C_6)$alkyl or $(C_1-C_6)$alkoxy;

$R^2$ is hydrogen or $-XR_a$;

$R^3$ is $-C(=O)YR_b$;

$R^4$ is $(=O)_n$; or $R^4$ is $(C_1-C_6)$alkyl, $(C_1-C_6)$alkanoyl or $(C_1-C_6)$alkanoyloxy and forms a sulfonium salt with the thiophene sulfur, wherein the associated counter ion is a pharmaceutically acceptable anion;

$R^5$ is hydrogen;

n is 0, 1 or 2;

X is oxygen or sulfur;

Y is oxygen or sulfur;

$R_a$ is $(C_1-C_6)$alkanoyl;

$R_b$ is hydrogen or $(C_1-C_3)$alkyl;

$R_c$ and $R_d$ are each independently hydrogen, $(C_1-C_4)$alkyl, phenyl, $C(=O)OH$, $C(=O)O(C_1-C_4)$alkyl $CH_2C(=O)OH$, $CH_2C(=O)O(C_1-C_4)$alkyl, or $(C_1-C_4)$alkoxy; or $R_c$ and $R_d$ together with the nitrogen to which they are attached are a 3, 4, 5, or 6 membered heterocyclic ring; and $R_e$ is hydrogen or $(C_1-C_6)$alkyl;

or a pharmaceutically acceptable salt thereof;

provided that $R^2$ and $R^3$ are on adjacent positions of the ring to which they are attached, or are on the 2- and 5-positions of the ring; and further provided that when $R^2$ is hydrogen; $R^3$ is on the 2-or 5-position of the ring to which it is attached and $R^4$ is $(C_1-C_4)$alkanoyloxy.

A specific aspirinate of formula I useful in the present invention is a compound of formula (II):

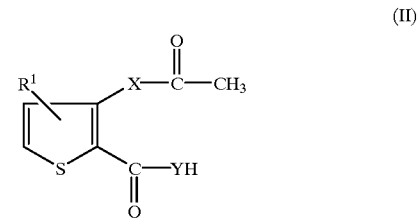

(II)

wherein X is O or S; Y is O or S; $R^1$ is hydrogen, halo, nitro, cyano, hydroxy, $CF_3$, $-NR_cR_d$, $-C(=O)OR_e$, $-OC(=O)OR_e$, $-C(=N)OR_e$, $(C_1-C_6)$alkyl or $(C_1-C_6)$alkoxy; and $R_c$ and $R_d$ are each independently hydrogen, $(C_1-C_4)$alkyl, phenyl, $-C(=O)OH$, $-C(=O)O(C_1-C_4)$alkyl, $-CH_2C(=O)OH$, $-CH_2C(=O)O(C_1-C_4)$alkyl, or $(C_1-C_4)$alkoxy; or $R_c$ and $R_d$ together with the nitrogen to which they are attached are a 3, 4, 5, or 6 membered heterocyclic ring; or a pharmaceutically acceptable salt thereof.

A specific aspirinate of formula I useful in the present invention is a compound of formula (II):

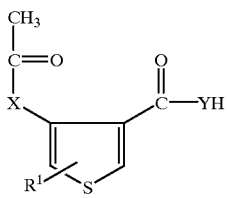

(III)

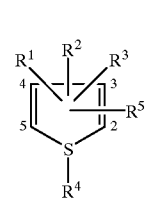

(I)

wherein X is O or S; Y is O or S; $R^1$ is hydrogen, halo, nitro, cyano, hydroxy, $CF_3$, —$NR_cR_d$, —C(=O)$OR_e$, —OC(=O)$OR_e$, —C(=N)$OR_e$, $(C_1-C_6)$alkyl or $(C_1-C_6)$alkoxy; $R_c$ and $R_d$ are each independently hydrogen, $(C_1-C_4)$alkyl, phenyl, —C(=O)OH, —C(=O)O$(C_1-C_4)$alkyl, —$CH_2$C(=O)OH, —$CH_2$C(=O)O$(C_1-C_4)$alkyl, or $(C_1-C_4)$alkoxy; or $R_c$ and $R_d$ together with the nitrogen to which they are attached are a 3, 4, 5, or 6 membered heterocyclic ring; or a pharmaceutically acceptable salt thereof.

Another specific aspirinate of formula I useful in the present invention is a compound of formula (IV):

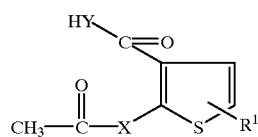

(IV)

wherein X is O or S; Y is O or S; $R^1$ is hydrogen, halo, nitro, cyano, hydroxy, $CF_3$, —$NR_cR_d$, —C(=O)$OR_e$, —OC(=O)$OR_e$, —C(=N)$OR_e$, $(C_1-C_6)$alkyl or $(C_1-C_6)$alkoxy; $R_c$ and $R_d$ are each independently hydrogen, $(C_1-C_4)$alkyl, phenyl, —C(=O)OH, —C(=O)O$(C_1-C_4)$alkyl, —$CH_2$C(=O)OH, —$CH_2$C(=O)O$(C_1-C_4)$alkyl, or $(C_1-C_4)$alkoxy;

or $R_c$ and $R_d$ together with the nitrogen to which they are attached are a 3, 4, 5, or 6 membered heterocyclic ring; or a pharmaceutically acceptable salt thereof.

Another specific aspirinate of formula I useful in the present invention is a compound of formula (V):

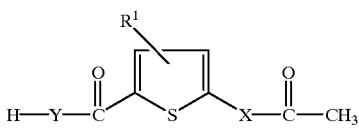

(V)

wherein X is O or S; Y is O or S; $R^1$ is hydrogen, nitro, halo, cyano, hydroxy, or $N(R)_2$, wherein each R is hydrogen, $(C_1-C_4)$alkyl, phenyl, COOH, $CO_2(C_1-C_4)$alkyl, or O[$(C_1-C_4)$alkyl], $R_c$ and $R_d$ are each independently hydrogen, $(C_1-C_4)$alkyl, phenyl, —C(=O)OH, —C(=O)O$(C_1-C_4)$alkyl, —$CH_2$C(=O)OH, —$CH_2$C(=O)O$(C_1-C_4)$alkyl, or $(C_1-C_4)$alkoxy; or $R_c$ and $R_d$ together with the nitrogen to which they are attached are a 3, 4, 5, or 6 membered heterocyclic ring; or a pharmaceutically acceptable salt thereof.

A specific aspirinate useful in the present invention is a compound of formula (I):

wherein
$R^1$ is hydrogen, halo, nitro, cyano, hydroxy, $CF_3$, —$NR_cR_d$, —C(=O)$OR_e$, $(C_1-C_6)$alkyl or $(C_1-C_6)$alkoxy;
$R^2$ is hydrogen or —$XR_a$;
$R^3$ is —C(=O)$YR_b$;
$R^4$ is (=O)$_n$; or $R^4$ is $(C_1-C_6)$alkyl, $(C1-C_6)$alkanoyl or $(C_2-C_6)$alkanoyloxy and forms a sulfonium salt with the thiophene sulfur, wherein the associated counter ion is a pharmaceutically acceptable anion;
$R^5$ is hydrogen;
n is 0, 1 or 2;
X is oxygen or sulfur;
Y is oxygen or sulfur;
$R_a$ is $(C_1-C_6)$alkanoyl;
$R_b$ is hydrogen or $(C_1-C_3)$alkyl;
$R_c$ and $R_d$ are each independently hydrogen, $(C_1-C_4)$alkyl, phenyl, COOH, $CO_2(_1-C_4)$alkyl or O[$(C_1-C_4)$alkyl] or $R_c$ and $R_d$ together with the nitrogen to which they are attached are pyrrolidino, piperidino, piperazin-1-ly or morpholino; and
$R_e$ is hydrogen or $(C_1-C_6)$alkyl;
or a pharmaceutically acceptable salt thereof;
provided that $R^2$ and $R^3$ are on adjacent positions of the ring to which they are attached, or are on the 2- and 5-positions of the ring; and further provided that when $R^2$ is hydrogen; $R^3$ is on the 2-or 5-position of the ring to which it is attached and $R^4$ is $(C_1-C_4)$alkanoyloxy.

A specific aspirinate useful in the present invention is a compound of formula (I) which is not 3-acetoxy-2-carboxythiophene.

Another specific aspirinate useful in the present invention is a compound of formula (I) wherein $R^1$ is halo, nitro, cyano, $CF_3$ or —C(=O)$OR_e$; or a pharmaceutically acceptable salt thereof.

Yet another specific aspirinate useful in the present invention is a compound of formula (I) wherein $R^1$ is hydrogen.

A further specific aspirinate useful in the present invention is a compound of formula (I) wherein $R^2$ is —$XR_a$.

A specific aspirinate useful in the present invention is a compound of formula (I) wherein $R^4$ is.$(C_1-C_6)$alkyl, $(C_1-C_6)$alkanoyl or $(C_2-C_6)$alkanoyloxy and forms a sulfonium salt with the thiophene sulfur, wherein the associated counter ion is a pharmaceutically acceptable anion.

A specific aspirinate useful in the present invention is a compound of formula (I) wherein $R^5$ is hydrogen.

Another specific aspirinate useful in the present invention is a compound of formula (I) wherein $R^2$ is in the 3-position, $R^3$ is in the 4-position and $R^1$ is halo, nitro, cyano, hydroxy, $CF_3$, —$NR_cR_d$, —C(=O)$OR_e$, $(C_1-C_6)$alkyl, or $(C_1-C_6)$alkoxy; or a pharmaceutically acceptable salt thereof.

Yet another specific aspirinate useful in the present invention is a compound of formula (I) wherein $R^2$ is in the 2-position and $R^3$ is in the 3-position; and $R^1$ is halo, nitro, cyano, hydroxy, $CF_3$, —$NR_cR_d$, —C(=O)$OR_e$, $(C_1-C_6)$alkyl, or $(C_1-C_6)$alkoxy; or a pharmaceutically acceptable salt thereof.

A specific aspirinate of formula I useful in the present invention is a compound of formula (II):

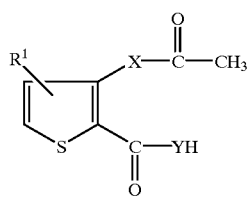

(II)

wherein X is O or S; Y is O or S; $R^1$ is hydrogen, nitro, halo, cyano, hydroxy, or $N(R)_2$, wherein each R is hydrogen, $(C_1-C_4)$alkyl, phenyl, COOH, $CO_2(C_1-C_4)$alkyl, or $O[(C_1-C_4)$alkyl]; or a pharmaceutically acceptable salt thereof.

A specific aspirinate of formula I useful in the present invention is a compound of formula II wherein, if X=Y=O, then $R^1$ is not H.

A specific aspirinate of formula I useful in the present invention is a compound of formula (III):

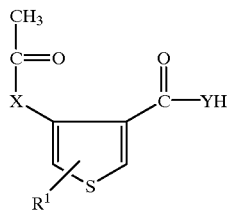

(III)

wherein X is O or S; Y is O or S; $R^1$ is hydrogen, nitro, halo, cyano, hydroxy, or $N(R)_2$, wherein each R is hydrogen, $(C_1-C_4)$alkyl, phenyl, COOH, $CO_2(C_1-C_4)$alkyl, or $O[(C_1-C_4)$alkyl]; or a pharmaceutically acceptable salt thereof.

Another specific aspirinate of formula I useful in the present invention is a compound of formula (IV):

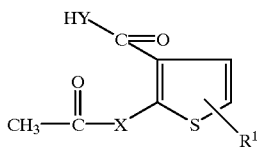

(IV)

wherein X is O or S; Y is O or S; $R^1$ is hydrogen, nitro, halo, cyano, hydroxy, or $N(R)_2$, wherein each R is hydrogen, $(C_1-C_4)$alkyl, phenyl, COOH, $CO_2(C_1-C_4)$alkyl, or $O[(C_1-C_4)$alkyl], or a pharmaceutically acceptable salt thereof.

Another specific aspirinate of formula I useful in the present invention is a compound of formula (V):

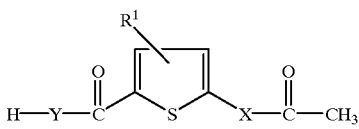

(V)

wherein X is O or S; Y is O or S; $R^1$ is hydrogen, nitro, halo, cyano, hydroxy, or $N(R)_2$, wherein each R is hydrogen, $(C_1-C_4)$alkyl, phenyl, COOH, $CO_2(C_1-C_4)$alkyl, or $O[(C_1-C_4)$alkyl], or a pharmaceutically acceptable salt thereof.

Another specific aspirinate useful in the present invention is a compound of formula II, III, IV or V wherein $R^1$ is hydrogen; or a pharmaceutically acceptable salt thereof.

Another specific aspirinate useful in the present invention is a compound of formula II, III, IV or V wherein $R^1$ is nitro, halo, cyano, hydroxy, or $N(R)_2$, wherein each R is hydrogen, $(C_1-C_4)$alkyl, phenyl, COOH, $CO_2(C_1-C_4)$alkyl, or $O[(C_1-C_4)$alkyl]; or a pharmaceutically acceptable salt thereof.

Another specific aspirinate useful in the present invention is a compound of formula II, III, IV or V wherein X is S.

Another specific aspirinate useful in the present invention is a compound of formula II, III, IV or V wherein Y is S.

The compounds of formulas (I), like aspirin, can transfer acetyl functionality. Moreover, the thiophene ring skeleton of compounds of formulas (I), which is similar in size to the benzene ring system in aspirin, results in a similar biodistribution, pharmacokinetics and pharmacodynamics for these compounds relative to aspirin. Furthermore, the thiophene ring sulfur (n=0) in a compound of formula I can be readily catabolized to sulfone (n=2) and sulfoxide (n=1), which increases the water solubility of the compounds, so they can be rapidly excreted. This rapid catabolism reduces the gastric irritation, gastric ulcers and occasional bleeding observed with high doses of aspirin, as well as kidney retention leading to crystal urea and kidney stones, all of which are due to the insolubility of salicylates and divalent and trivalent complexes of salicylates with metals. Besides being useful as TGF-beta elevating agents, the compounds of formula (I) are useful as anti-inflammatory agents, e.g., as anti-platelet aggregation agents, thrombin inhibitory agents, and vascular smooth muscle cell anti-proliferative agents.

Furthermore, substitution of electron withdrawing and electron donating functionalities on the thiophene ring system can enhance or diminish the bioavailability of the substituted compounds. Thus, some of the substituted compounds exhibit higher protein binding affinities, and thus have higher binding affinities to serum proteins. The higher binding affinities lead to a longer serum half-life, which provides a longer duration of action for the compounds. Other substituted compounds exhibit lower protein binding affinities, and thus have lower binding affinities to serum proteins. The lower binding affinities lead to a shorter serum half-life, which provides a shorter duration of action for the compounds. Moreover, the compounds of formula (I) can chelate metal ions, which can result in enhanced transport across membranes.

The aspirinates of the invention preferably include copper salts, as well as alkali metal or alkaline earth metal aspirinate salts, such as lithium, sodium, potassium, magnesium, zinc, or calcium aspirinate salts, although other salts are envisioned.

The copper aspirinate salts of the invention can be formed for example by reacting a copper salt such as cupric chloride with the sodium salts of 3,5-diisopropyl salicylic acid, acetylsalicylic acid, salicylic acid, 3,5-ditertiary butyl salicylic acid, adamantylsalicylic acid, 3,5-dibromoacetylsalicylic acid, 3,5-diiodoacetylsalicylic acid, 4-tertiary butylsalicylic acid, 4-nitrosalicylic acid, 4-aminosalicylic acid, 4-acetylaminosalicylic acid, 5-chlorosalicylic acid and 3,5-dichlorosalicylic acid.

The copper salt of a thiophene-ring based analog or derivative of an aspirinate of the invention can be prepared by reacting a copper salt, e.g., cupric chloride, with the sodium salt of the thiophene-based analog or derivative.

Inorganic copper salts useful in synthesizing copper aspirinate salts of the invention include hydrated copper chloride, and the dehydrate thereof, hydrated copper fluoride and the dehydrate thereof, copper fluorosilicate and the hexahydrate thereof, copper sulfate and the pentahydrate thereof, copper nitrate and the tri- and hexa-hydrates thereof, copper bromide, copper metaborate, copper bromate, copper chlorate, copper iodate and copper fluorophosphate. In the above salts, the copper is typically in the Copper (II) oxidation state.

It is preferable to produce copper aspirinate coordination solvates rather than nanhydrous compounds. The copper aspirinate compounds may be solvated with a lower alkanol, e.g., a $C_2$–$C_6$ aliphatic alkanol such as ethanol or isopropanol, a ketone such as acetone or methylethylketone, alkanolamines, pyridine, water, dimethyl formamide, or dimethyl sulfoxide.

Compounds of Formula (VI) Falling within the Scope of the Invention

A specific compound of formula VI is a compound wherein — — — is a single bond.

Another specific compound of formula VI is a compound wherein $R^9$ and $R_j$ together are —$CH_2CH_2$—, —S—, —O——N(H)—, —N[($C_1$–$C_6$)alkyl]—, or —CH=CH—.

Another specific compound of formula VI is a compound wherein — — — is —C(B)(D)—, wherein B and D are each halogen; and $R^8$ and $R^9$ are both hydrogen.

Another specific compound of formula VI is a compound wherein $R^6$ is not phenyl or phenyl substituted by 1 or 2 V.

Another specific compound of formula VI is a compound wherein $R^7$ is not phenyl or phenyl substituted by 1 or 2 V.

Another specific compound of formula VI is a compound wherein $R^8$ is not phenyl, or phenyl substituted by 1 or 2 V.

A specific value for Z is —$(CH_2)_{1-3}$—, —O—, —$OCH_2$—, —$CH_2O$—, —C(=O)O—, —N($R_q$)—, or a covalent bond. Another specific value for Z is —O—, —$OCH_2$—, —$CH_2O$—, —C(=O)O—, or —N($R_q$)—.

A specific compound of formula VI is a compound of formula VII:

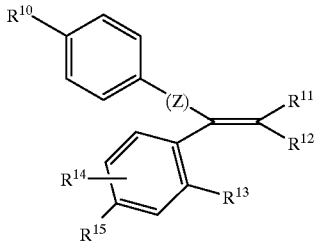

(VII)

wherein

Z is C=O or a covalent bond;

$R^{10}$ is mercapto, ($C_1$–$C_4$)alkylthio, hydroxy, ($C_1$–$C_6$)alkoxy, —O($CH_2$)$_{1-4}$COOH, —S($CH_2$)$_{1-4}$COOH, —($CH_2$)$_{0-4}$COOH, —O($CH_2$)$_{2-4}$OH, —S($CH_2$)$_{2-4}$OH, —O($CH_2$)$_{1-4}$(C=O)$R_r$, —S($CH_2$)$_{1-4}$(C=O)$R_r$, —O($CH_2$)$_{2-4}$$R_r$, —S($CH_2$)$_{2-4}$$R_r$, —($CH_2$)$_{0-4}$$R_r$, or —($CH_2$)$_{0-4}$C(=O)$R_r$;

$R^{11}$ is 3-($R_s$)-4-($R_t$)phenyl, halo($C_1$–$C_{12}$)alkyl, ($C_1$–$C_{12}$)alkyl, ($C_3$–$C_6$)cycloalkyl, ($C_1$–$C_6$)alkylcyclo($C_1$–$C_6$)alkyl, ($C_3$–$C_6$)cycloalkenyl, or ($C_1$–$C_6$)alkyl($C_3$–$C_6$)cycloalkenyl;

$R^{12}$ is nitro, halo, ethyl, 2-cyanoethyl, 2-trifluoromethylethyl, —$CH_2CH_2$C(=O)O($C_1$–$C_4$)alkyl, chloroethyl, cyclohexane, or naphthalene;

$R^{13}$ is H or together with $R^{12}$ is O—CH=CH—, —$CH_2$—$CH_2$— or —S—, $R^{14}$ is hydrogen, iodo, O($C_1$–$C_4$)alkyl, hydroxy, —C(=O)O($C_1$–$C_6$)alkyl, —OC(=O)($C_1$–$C_6$)alkyl, benzyl, or OSO$_2$(CH$_2$)0-4CH$_3$;

$R^{15}$ is hydrogen, ($C_1$–$C_6$)alkyl, mercapto, ($C_1$–$C_4$)alkylthio, hydroxy, ($C_1$–$C_6$)alkoxy, iodo, OPO$_3$H$_2$, —OSO$_2$(CH$_2$)$_{0-4}$CH$_3$, —C(=O)O($C_1$–$C_6$)alkyl, —OC(=O)($C_1$–$C_6$)alkyl, or benzyl;

$R_r$ is amino, optionally substituted with one or two ($C_1$–$C_6$)alkyl; or $R_r$ is an N-heterocyclic ring which optionally comprises another hetero atom selected from N, O, or S in said ring;

$R_s$ is hydrogen, halo, or hydroxy; and $R_t$ is hydrogen, ($C_1$–$C_6$)alkyl, mercapto, ($C_1$–$C_4$)alkylthio, hydroxy, ($C_1$–$C_6$)alkoxy, —OSO$_2$—(CH$_2$)$_{0-4}$—CH$_3$, halo, —OC(=O)($C_1$–$C_6$)alkyl, or benzyl;

the compound is MER25, zindoxifene, DDAC (Analog II) or DTAC 102b);

a pharmaceutically acceptable salt thereof, or mixtures thereof.

A preferred compound of formula VII useful in the present invention is a compound wherein $R^{14}$ is at the 5-position of the phenyl ring to which it is attached.

Another specific compound of formula (VI) useful in the present invention is a compound of formula (VIII):

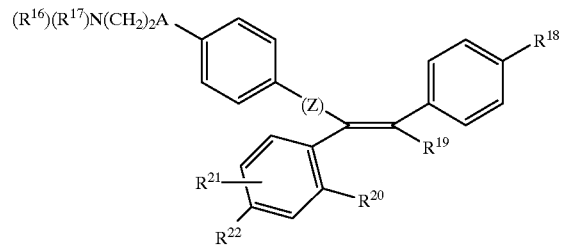

(VIII)

wherein

A is O or S;

Z is C=O or a covalent bond;

$R^{16}$ and $R^{17}$ are individually ($C_1$–$C_4$)alkyl or together with N are a saturated heterocyclic ring, preferably a 5–7 membered heterocyclic ring optionally containing 1–2 additional N($R_u$), S or nonperoxide O, wherein $R_u$ is hydrogen, ($C_1$–$C_4$)alkyl, phenyl or benzyl;

$R^{18}$ is hydrogen, ($C_1$–$C_6$)alkyl, mercapto, ($C_1$–$C_4$)alkylthio, hydroxy, ($C_1$–$C_6$)alkoxy;

$R^{19}$ is nitro, halo, ethyl, 2-cyanoethyl, 2-trifluoromethylethyl, —$CH_2CH_2$C(=O)O($C_1$–$C_4$) alkyl, or chloroethyl;

$R^{20}$ is H or together with $R^{19}$ is —$CH_2$—$CH_2$— or —S—;

$R^{21}$ is hydrogen, iodo, hydroxy, or O($C_1$–$C_4$)alkyl;

$R^{22}$ is hydrogen, ($C_1$–$C_6$)alkyl, mercapto, ($C_1$–$C_4$)alkylthio, hydroxy, ($C_1$–$C_6$)alkoxy, halo, or OPO$_3$H$_2$;

the compound is MER25, zindoxifene, DDAC (Analog II) or DTAC (102b);

a pharmaceutically acceptable salt thereof, or mixtures thereof

Another specific compound of formula (VI) useful in the present invention is a compound of formula (VIII):

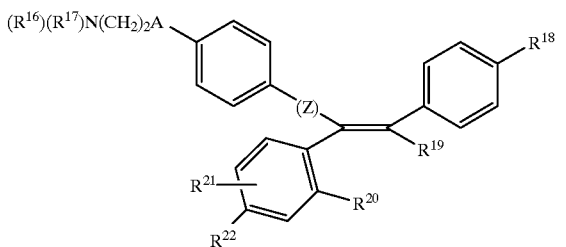

(VIII)

wherein

A is O;

Z is C=O or a covalent bond;

$R^{16}$ and $R^{17}$ are individually $(C_1-C_4)$alkyl or together with N are a saturated heterocyclic ring, preferably a 5–7 membered heterocyclic ring optionally containing 1–2 additional $N(R_u)$, S or nonperoxide O, wherein $R_u$ is hydrogen, $(C_1-C_4)$alkyl, phenyl or benzyl;

$R^{18}$ is hydrogen, hydroxy, $(C_1-C_4)$alkyl, or $(C_1-C_4)$alkoxy;

$R^{19}$ is nitro, halo, ethyl or chloroethyl;

$R^{20}$ is H or together with $R^{19}$ is —$CH_2$—$CH_2$— or —S—;

$R^{21}$ is hydrogen, iodo, hydroxy, or $(C_1-C_4)$alkoxy;

$R^{22}$ is iodo, $OPO_3H_2$, $(C_1-C_4)$alkoxy or hydrogen;

the compound is MER25, zindoxifene, DDAC (Analog II) or DTAC 102b);

a pharmaceutically acceptable salt thereof, or mixtures thereof.

A preferred compound of formula VIII useful in the present invention is a compound wherein Z is a covalent bond; $R^{16}$ and $R^{17}$ are each $(C_1-C_4)$alkyl or —$(CH_2)_m$—; $R^{18}$ is hydrogen; $R^{21}$ is hydrogen or iodo; and m is 4–6.

A preferred compound of formula VIII useful in the present invention is a compound wherein $R^{19}$ is ethyl or chloroethyl.

A preferred compound useful in the present invention is a compound of formula VIII wherein $R^{19}$ and $R^{20}$ together are —$CH_2$—$CH_2$—; and $R^{22}$ is $OCH_3$.

A preferred compound of formula VIII useful in the present invention is a compound wherein:

Z is C=O or a covalent bond;

$R^{16}$ and $R^{11}$ are individually $(C_1-C_4)$alkyl or together with N are a saturated heterocyclic ring, preferably a 5–7 membered heterocyclic ring optionally comprising 1–2 additional N(R), S or nonperoxide O, wherein R is hydrogen, $(C_1-C_4)$alkyl, phenyl or benzyl;

$R^{18}$ is hydrogen, hydroxy or $O(C_1-C_4)$alkyl;

$R^{19}$ is ethyl or chloroethyl;

$R^{20}$ is H or together with $R^{19}$ is —$CH_2$—$CH_2$— or —S—;

$R^{21}$ is hydrogen, iodo, hydroxy, or $O(C_1-C_4)$alkyl;

$R^{22}$ is iodo, $OPO_3H_2$, $O(C_1-C_4)$alkyl or hydrogen;

a pharmaceutically acceptable salt thereof, or mixtures thereof.

Additionally for any compound of formula VIII or preferred compound of formula VIII described above, a specific value for $R^{18}$ is hydrogen; for Z is a covalent bond; for $R^{16}$ and $R^{17}$ is independently $(C_1-C_4)$alkyl, or for $R^{16}$ and $R^{17}$ taken together is —$(CH_2)_m$—; for $R^{21}$ is hydrogen or iodo; and for m is 4–6.

Additionally for any compound of formula VIII or preferred compound of formula VIII described above, a specific value for $R^{22}$ is $OCH_3$; and for $R^{19}$ and $R^{20}$ together is —$CH_2$—$CH_2$—.

Compounds of formula VI useful in the present invention include tamoxifen and structural analogs of tamoxifen having substantial equivalent bioactivity. Such analogs include idoxifene, raloxifene, droloxifene, 3-iodotamoxifen, 4-iodotamoxifen, tomremifene, trioxifene, nafoxidene, 4-hydroxytamoxifen, H-1285, and pharmaceutically acceptable salts thereof. A preferred embodiment of the invention is a compound of formula (VIII) wherein $R^{19}$ is not ethyl when $R^{20}$, $R^{21}$, and $R^{22}$ are H.

The term "structural analogs thereof" with respect to tamoxifen includes, but is not limited to, all of the compounds of formula (VI) which are capable of enhancing, increasing or elevating the level of TGF-beta. See, for example, U.S. Pat. Nos. 4,536,516, 5,457,113, 5,047,431, 5,441,986, 5,426,123, 5,384,332, 5,453,442, 5,492,922, 5,462,937, 5,492,926, 5,254,594 and U.K. Patent 1,064,629.

Because tamoxifen (TMX) causes liver carcinogenicity in rats and has been correlated with an increased risk of endometrial cancer in women and may increase the risk of certain gut cancers, other tamoxifen analogs may be considered safer to administer if they are less carcinogenic. The carcinogenicity of TMX has been attributed to the formation of covalent DNA adducts. Of the TMX analogs and derivatives, only TMX and toremifene have been studied for long-term carcinogenicity in rats. These studies provide strong evidence that covalent DNA adducts are involved in rodent hepatocarcinogenicity of TMX. Toremifene, which exhibits only a very low level of hepatic DNA adducts, was found to be non-carcinogenic. See Potter et al., *Carcinogenesis*, 5, 439 (1994).

It is postulated that 4-hydroxylation of TMX yields electrophilic alkylating agents which alkylate DNA through the ethyl group of TMX. This mechanistic hypothesis explains the low level of DNA adduct formation by the non-TMX analogs of formula (VI), including the TMX analog toremifene, and the absence of DNA adducts detected for the analogs 4-iodotamoxifen and idoxifene. Thus, all of these analogs are likely to be free from the risk of significant carcinogenesis in long term use. See Potter et al., supra. Idoxifene (IDX) includes (E)-1-[4-[2-(N-pyrrolidino) ethoxy]phenyl]-1-(4-iodophenyl)-2-phenyl-1-butene and its pharmaceutically acceptable salts and derivatives. See R. McCague et al., *Organic Preparations and Procedures Int.*, 26, 343 (1994) and S. K. Chandler et al., *Cancer Res.*, 5851 (1991). Besides its lower potential for inducing carcinogenesis via formation of DNA adducts which can damage DNA, other advantages of IDX compared with TMX are that IDX has reduced residual estrogenic activity in rats and an improved metabolic profile.

Other "antisteroids" or "steroidal antagonists" are useful as TGF-beta activators or production stimulators or lead compounds, including other known stilbene-type antisteroids such as for example, cis- and trans-clomiphene, toremifene, centchroman, raloxifene, droloxifene, (1-[4-(2-dimethylaminoethoxy)phenyl]-1-(3-hydroxyphenyl)-2-phenyl-2-butene (see U.S. Pat. No. 5,384,332), 1-nitro-1-phenyl-2-(4-hydroxyphenyl or anisyl)-2-[4-(2-pyrrol-N-ylethoxy)-phenyl]ethylene(CN-55,945),trans-1,2-dimethyl-1,2-(4-hydroxyphenyl)ethylene(trans-dimethylstilboestrol), trans-diethylstilboestrol, and 1-nitro-1-phenyl-2-(4-hydroxyphenyl)-2-[4-(3-dimethylaminopropyloxy)phenyl-ethylene (GI680), metabolites or pharmaceutically acceptable salts thereof.

Known 1,2-diphenylethane-type antisteroids include cis-1,2-anisyl-1-[4-(2-diethylaminoethoxy)phenyl]ethane (MRL-37), 1-(4-chlorophenyl)1-[4-(2-diethylaminoethoxy)phenyl]-2-phenylethanol (WSM-4613); 1-phenyl-1[4-(2-diethylaminoethoxy)phenyl]-2-anisylethnmol (MER-25); 1-phenyl-1-[4-(2-diethylaminoethoxy)phenyl)-2-anisyl-ethane, mesobutoestrol (trans-1,2-dimethyl-1,2-(4-hydroxyphenyl)-ethane), meso-hexestrol, (+)hexestrol and (−)-hexestrol.

Known naphthalene-type antisteroids include nafoxidine, 1-[4-(2,3-dihydroxypropoxy)phenyl]-2-phenyl-6-hydroxy-1,2,3,4-tetrahydro-naphthalene, 1-(4-hydroxyphenyl)-2-phenyl-6-hydroxy-1,2,3,4-tetrahydronaphthalene, 1-[4-(2-pyrrol-N-ylethoxy)-phenyl]-2-phenyl-6-methoxy-3,4-dihydronaphthalene (U11, 100A), and 1-[4-(2,3-dihydroxypropoxy)phenyl]-2-phenyl-6-methoxy-3,4-dihydronaphthalene (U-23, 469).

Known antisteroids which do not fall anywhere within these structural classifications include coumestrol, biochanin-A, genistein, methallenstril, phenocyctin, and 1-[4-(2-dimethylaminoethoxy)phenyl]-2-phenyl-5-methoxyindene (U, 11555). In the nomenclature employed hereinabove, the term "anisyl" is intended to refer to a 4-methoxyphenyl group.

Preparation of a Compound of Formula (I–V)

Generally, a compound of formula I wherein $R^4$ is $(=O)_n$ and n is 0 may be prepared by processes which are well known in the chemical arts for the synthesis of thiophene compounds and other aromatic compounds.

A compound of formula I wherein $R^4$ is $(=O)_n$ and n is 1 or 2 can be prepared from a corresponding compound of formula II wherein n is 0, by oxidation of the thiophene sulfur using standard oxidation conditions.

Compounds of formula I wherein $R^4$ is $(C_1-C_6)$alkyl, $(C_1-C_6)$alkanoyl or $(C_2-C_6)$alkanoyloxy and forms a sulfonium salt with the thiophene sulfur, wherein the associated counter ion is a pharmaceutically acceptable anion, can be prepared from corresponding compounds of formula I wherein $R^4$ is $(=O)_n$ and n is 0 by alkylation or acylation of the thiophene sulfur, using procedures which are well known in the art.

The synthesis of a compound of formula (II) can be carded out as follows

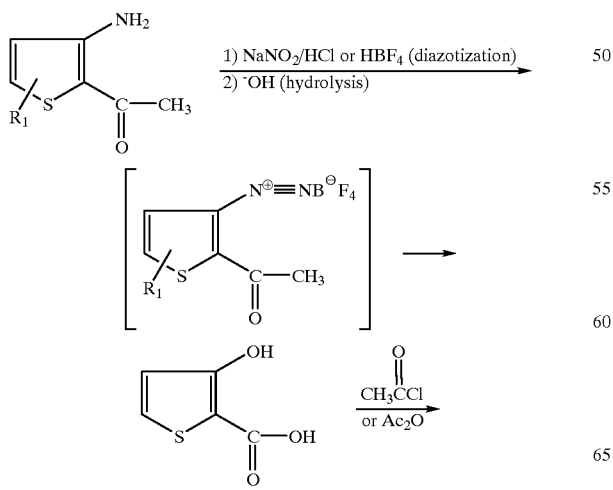

The synthesis of a compound of formula (III) may be carried out as follows:

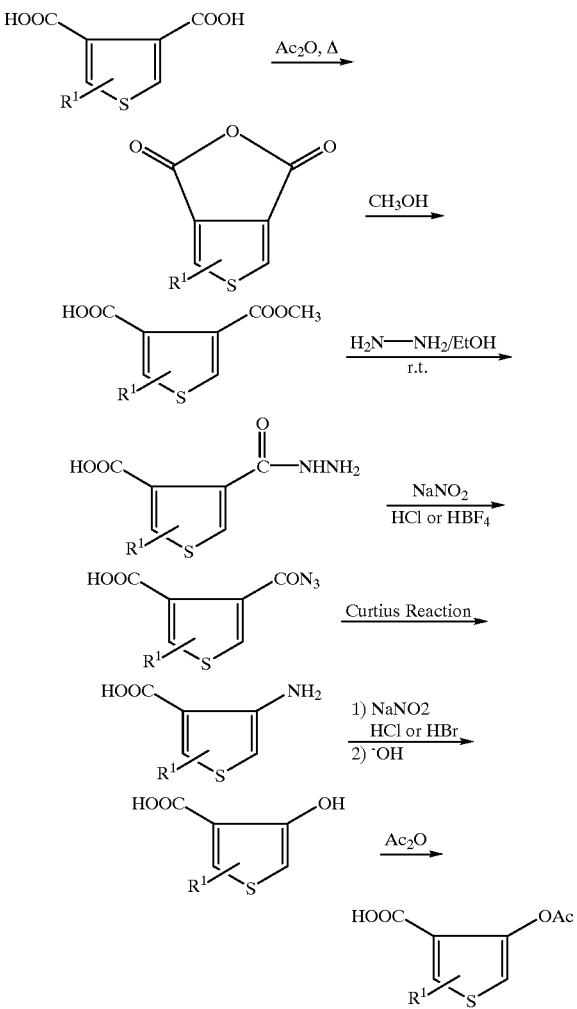

The synthesis of a compound of formula (IV) may be carried out as follows:

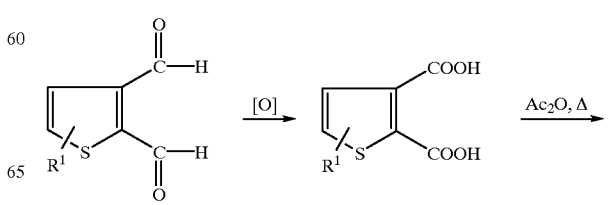

-continued

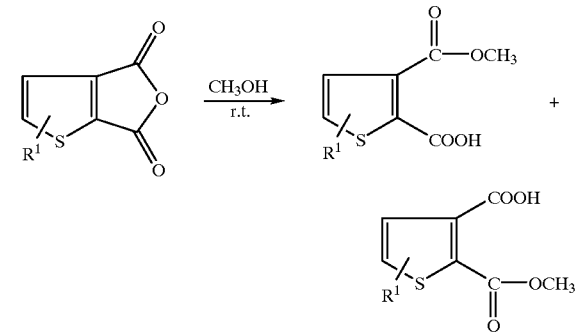

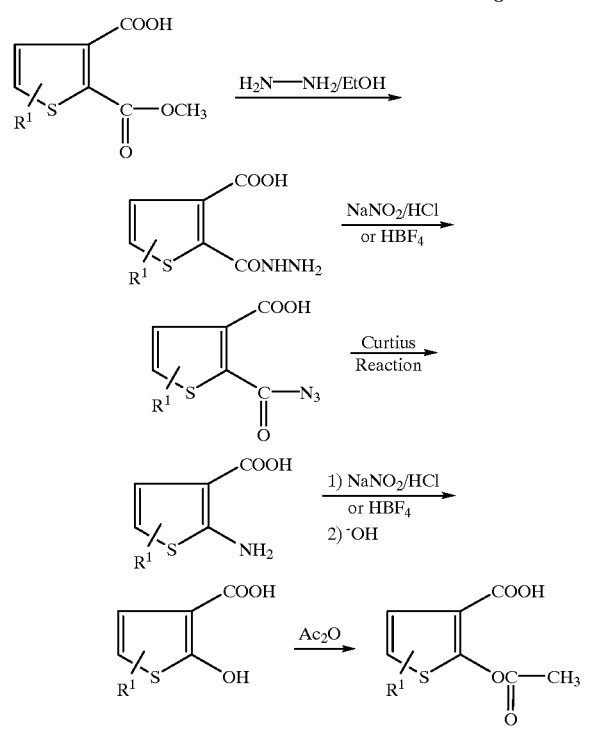

The synthesis of a compound of formula (V) may be carried out as follows:

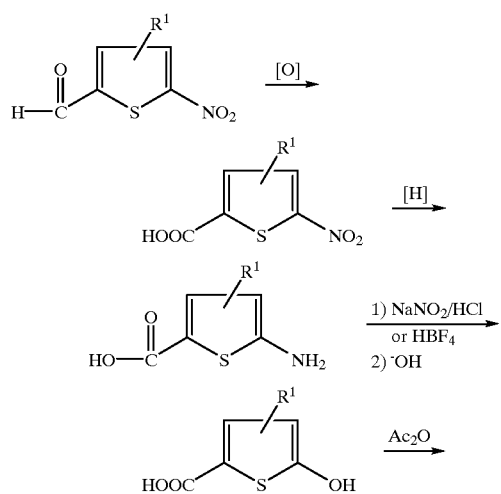

-continued

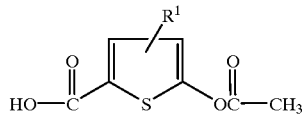

Preparation of Compounds of Formula (VI)

Generally, compounds of formula (VI) may be prepared using synthetic techniques which are analogous to techniques known in the art, including techniques described in R. A. Magarian, *Current Medicinal Chemistry*, 1994, 1, 61–104 and techniques described in the references relating to tamoxifen analogs which are cited and incorporated herein.

It may be convenient to optionally use a conventional protecting group during the preparation of compounds of formula (I) or compounds of formula (VI). The protecting group may be removed at an appropriate time during the synthesis, such as for example, when the final compound is to be formed. Such processes and intermediates for the manufacture of a compound of formula I are provided as further features of the invention.

Pharmaceutically Acceptable Acid and Base Addition Salts

The compounds used in the methods of the invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydriodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1, sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula (I) or (VI) with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly uged for formation of acid salts include ammonium hydroxide and alkali and alkaline earth metal hydroxide, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions, and can have enhanced bioavailability.

Identification of Therapeutic Agents Falling within the Scope of the Invention

Therapeutic agents useful in the practice of the invention, i.e., agents that elevate or increase TGF-beta levels, can be identified by an in vitro assay described in copending U.S. application Ser. No. 08/476,735, the disclosure of which is incorporated by reference herein, and/of the assays described in the Examples hereinbelow. It is recognized that not all therapeutic agents, e.g., aspirinates, can increase TGF-beta levels. Moreover, it is recognized that some therapeutic agents within the scope of the invention increase TGF-beta levels to a greater extent than other TGF-beta elevating agents, however, methods to determine whether an agent falls within the scope of the invention are described hereinbelow.

The amounts of latent and/or active TGF-beta present in a sample of physiological fluid, such as a blood fraction, before and/or after the administration of the therapeutic agent, can be measured by methods disclosed in copending U.S. application Ser. No. 08/477,393 and U.S. Pat. No. 5,545,569, issued Aug. 13, 1996, the disclosures of which are incorporated by reference herein.

For example, to determine whether an agent can elevate levels of TGF-beta, an agent or mixture of agents is first tested on rat aortic vascular smooth muscle cells (rVSMCs) for their ability to stimulate the production of active TGF-β in the culture medium as originally described for tamoxifen. See Grainger et al. (*Biochem. J.*, 224, 109 (1993)). The key step in demonstrating that cells have a reduced proliferation rate as a result of TGF-β production and activation is that the effect can be fully reversed by neutralizing antibodies to TGF-β. Incomplete reversal of a decreased rate of proliferation is evidence for TGF-β independent effect(s), which may include toxicity.

The effects of an agent are then tested on explant human aortic smooth muscle cells (hVSMC) to determine whether the agent also stimulates production of TGF-β by these cells. The use of explant hVSMCs, is essential because (I) explant hVSMCs grown under non-optimal conditions (particularly at low cell densities) will spontaneously produce TGF-β; (ii) hVSMC cultures from cells prepared by enzyme dispersal spontaneously produce substantial amounts of TGF-β in culture (Kirsehenlohr et al., *Am. J. Physiol.*, 265, C571 (1993)) and therefore cannot be used for screening; and (iii) the sensitivity of rVSMCs and hVSMCs to agents which induce the cells to produce TGF-β differs by up to 100-fold.

In screening for agents likely to be effective for clinical purposes, it is therefore necessary to use hVSMCs to determine both potency and the therapeutic window between effective concentrations and toxic concentrations for human cells. Candidate agents which pass the in vitro cell culture screens are then tested on one or more animal models of vascular conditions or disease, e.g., animal models of atherosclerosis include lipid lesion formation in C57B16 mice and mice expressing the human apo(a) transgene that are fed a high fat diet, apoE knockout mice fed a normal diet, or cholesterol-fed Watanabe rabbits.

To determine total TGF-beta, ELISA plates are coated with a chicken antibody that binds both latent and active TGF-beta. Patient sera or plasma are incubated with these ELISA plates, then the plates are washed to remove unbound components of the patients' sera or plasma. Rabbit anti-TGF-beta antibody, capable of binding both latent and active TGF-beta, is then added to the plates and incubated. The plates are then washed to remove unbound antibody, and peroxidase-labeled anti-rabbit IgG is added. After incubation and washing, the plates are exposed to the chromogenic substrate, ortho-phenylenediamine. The presence of total TGF-beta in patients' sera or plasma is then determined calorimetrically at $A_{492}$ by comparison to a standard curve. In patients treated with an agent that modifies TGF-beta, a pretreatment determination of TGF-beta can be compared with post-treatment time points to monitor treatment results and effectiveness.

In an alternate format, TGF-beta type II receptor extracellular domain, which recognizes the active form(s) of TGF-beta, but not the mature or latent forms, is coated onto ELISA plates. Patient sera or plasma are added to the plates, and processed as above. This assay measures active TGF-beta present in sera or plasma.

In another alternate format, fluorescent-labeled anti-TGF-beta antibody is used in place of peroxidase labeled second antibody to detect the presence of TGF-beta in patients' sera or plasma. In yet another alternate format, anti-TGF-beta antibody is labeled with a radioactive moiety capable of detection by standard means. These latter two assays may be performed in an ELISA format, with or without using the additional anti-TGF-beta antibody described above.

It is envisioned that the therapeutic agents of the invention can increase TGF-beta levels by increasing the number of TGF-beta transcripts, increasing the translational efficiency of TGF-beta transcripts, increasing the post-translational processing of the latent form of TGF-beta to the active form of TGF-beta, increasing the bioavailability of TGF-beta, and/or increasing the biological effect of active TGF-beta, e.g., by increasing the affinity of TGF-beta for its receptor, increasing the affinity of the receptor for TGF-beta and/or by increasing the number of receptors for TGF-beta on the cell surface, or any combination thereof. For example, the administration of aspirin or copper aspirinate (see Examples III and IV) can increase the level of latent TGF-beta in a mammal relative to the level of latent TGF-beta in that mammal prior to aspirin or copper aspirinate administration.

Agents useful in the practice of the methods of the invention can also be identified by the correlation of agent administration with the inhibition or reduction in atherosclerotic plaque development or formation, an increase in lesion regression or plaque stability, or a decrease vascular wall hypertrophy and/or hyperplasia in vivo. Agent efficacy is measured by methods available to those skilled in the art including, but not limited to, angiography, ultrasonic evaluation, fluoroscopic imaging, fiber optic endoscopic examination or biopsy and histology. The activity of the therapeutic agents of the invention in vivo can also be monitored indirectly by the measurement of the levels of TGF-beta in a patient before and after the administration of the therapeutic agent.

For non-vascular indications, agents useful in the practice of the invention can be identified by the correlation of in vivo agent administration with a reduction in a particular pathology associated with the non-vascular indication. For example, animal models for multiple sclerosis (Martin et al., *Ann. Rev. Immunol.*, 10, 153 (1992); Hafler et al., *Immunol. Today*, 10, 107 (1989), WO 93/16724) and rheumatoid arthritis (WO 93/16724) may be employed to determine the activity of the therapeutic agents of the invention in vivo. Additionally, suitable animal models for osteoporosis (suspension induced osteoporosis in rats) and cancer (DMBA-induced skin cancer) are well known in the art.

Vascular indications Amenable to Treatment by the Claimed Methods

The therapeutic agents of the invention are useful to treat a mammal such as a human patient, afflicted with, or at risk of, a vascular indication. In particular, the therapeutic agents of the invention are useful to treat a mammal afflicted with, or at risk of, a vascular indication associated with a deficiency in TGF-beta.

A mammal afflicted with, or at risk of, a vascular indication that would benefit from the practice of the claimed invention includes a mammal exhibiting a reduced level of TGF-beta within the vessel wall. Such mammals may be identified as having one or more risk factors which contribute to reduced TGF-beta activity. These factors include low serum active levels of TGF-beta, elevated circulating PAI-1 antigen or activity, elevated circulating lipoprotein (a), elevated blood concentration of LDL and/or VLDL in the fasting state, the ability to elevate PAI-1 following a fat tolerance test, the presence of the 4G allele of the PAI-1 promoter, and the like. Thus, the measurement of PAI-1/TGF-beta response (Example 7) to fat feeding is one method to determine whether an individual is at risk of a vascular indication associated with a deficiency in TGF-beta levels. For example, low serum active TGF-beta levels can be levels that are less than about 4 ng/ml, preferably less than about 3 ng/ml, and more preferably less than about 2 ng/ml.

Dosages, Formulations and Routes of Administration of the Therapeutic Agents of the Invention Aspirin or aspirinates, e.g., the compounds of formulas (I), and lie aspirinate salts of the invention, including their coordination solvates, are preferably administered at doses of about 0.001–600 mg/kg, more preferably at doses of about 2.0–165 mg/kg, and even more preferably at doses of about 1.0–100 mg/kg of body weight, although other dosages may provide beneficial results.

Fish oil, a source of omega-3 fatty acids, is administered at doses of about 200–18000 mg/kg/day, more preferably at doses of about 1000–6000 mg/kg/day, and even more preferably at doses of about 1200–4000 mg/kg/day, although other dosages may provide beneficial.

For compounds of the formula (VI), generally, accepted and effective daily doses will be from about 0.05 mg/kg/day to about 10 mg/kg/day, preferably about 0.1–1.0 mg/kg/day, more preferably about 0.3–0.5 mg/kg/day. For local delivery, an exemplary dose will be about 0.01 to about 1000 $\mu$g/ml, preferably followed by a chronic lower dose, which is preferably administered orally. It is also contemplated that a large loading dose may be employed, e.g., about 10 to about 100 mg/kg, to rapidly establish a therapeutic level of the agent. The large loading dose is preferably followed by a chronic dose of about 0.1 to about 20 mg/kg/day, preferably about 0.5 to about 2 mg/kg/day. It is preferred that a compound of formula (VI) is administered in the form of an acid addition salt, as is customary in the administration of pharmaceuticals comprising a basic group, such as an amino or N-heterocyclic group.

The amount of therapeutic agent administered is selected to treat a particular vascular indication. For example, to treat vascular traumas of differing severity, smaller doses are sufficient to treat lesser vascular trauma, such as to prevent vascular rejection following graft or transplant, while larger doses are sufficient to treat more extensive vascular trauma, such as restenosis following angioplasty. The therapeutic agents of the invention are also amenable to chronic use for prophylactic purposes to treat disease states involving proliferation of vascular smooth muscle cells and pericytes derived from the medial layers of vessels, pericytes and fibroblasts in the adventitia, and migrating macrophage/monocyte/foam cells, over time (e.g., atherosclerosis, coronary heart disease, thrombosis, myocardial infarction, stroke, uterine fibroid or fibroma and the like), preferably by systemic administration.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses, e.g., either before, during, or after procedural vascular trauma, before and during, before and after, during and after, or before, during and after the procedural trauma.

One or more suitable unit dosage forms comprising the therapeutic agents of the invention, which, as discussed below, may be formulated for sustained release, can be administered by a variety of routes including oral, or parenteral, including by rectal, transdermal, subcutaneous, intravenous, intramuscular, intrapulmonary and intranasal routes. When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof.

Pharmaceutical formulations containing the therapeutic agents of the invention can be prepared by procedures known in the art using well known and readily available ingredients. For example, a copper aspirinate including copper 2-acetylsalicylate, or a compound of formula (I), as well as a compound of formula (VI), can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC, and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing aspirinates of the invention can include buffering agents such as calcium carbonate, magnesium oxide and magnesium carbonate. Caplets and tablets can also include inactive ingredients such as cellulose, pregelatinized starch, silicon dioxide, hydroxypropyl methylcellulose, magnesium stearate, microcrystalline cellulose, starch, talc, titanium dioxide, benzoic acid, citric acid, corn starch, mineral oil, polypropylene glycol, sodium phosphate, and zinc stearate, and the like.

Hard or soft gelatin capsules containing aspirinates of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, the enteric coated caplets or tablets of the copper aspirinates of the invention are designed to resist disintegration in the stomach and dissolve in the more neutral to alkaline environment of the duodenum.

The pharmaceutical formulations of the therapeutic agents of the invention can take the form of an aqueous or anhydrous solution or dispersion, or alternatively the form of an emulsion or suspension. The therapeutic agents of the invention can also be formulated as elixirs or solutions for convenient oral administration or as solutions appropriate for parenteral administration, for instance by intramuscular, subcutaneous or intravenous routes.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol"; polyglycols and polyethylene glycols $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, alginates, guar, or carbo gum or gum arabic, or alternatively thickeners such as polyethylene glycols, bentones and montmorillonites, and the like.

It is possible to add, if necessary, an adjuvant chosen from antioxidants, surfactants, preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent effective for reducing vessel lumen diameter diminution, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, crosslinking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

The local delivery of the therapeutic agents of the invention can also be by a variety of techniques which administer the agent at or near the diseased or traumatized vascular site. Examples of site-specific or targeted local delivery techniques are not intended to be limiting but to be illustrative of the techniques available. Examples include local delivery catheters, such as an infusion or indwelling catheter, a needle catheter, shunts and stents or other implantable devices, site specific carriers, direct injection, or direct applications. In addition, local delivery of the therapeutic agents to branch points may be particularly beneficial as active TGF beta levels are lower at branch points, where lesion formation is increased relative to non-branch points.

Catheters which may be useful in the practice of the invention include catheters such as those disclosed in Just et al. (U.S. Pat. No. 5,232,444), Abusio et al. (U.S. Pat. No. 5,213,576), Shapland et al. (U.S. Pat. No. 5,282,785), Racchini et al. (U.S. Pat. No. 5,458,568) and Shaffer et al. (U.S. Pat. No. 5,049,132), the disclosures of which are incorporated by reference herein.

For a compound of formula (VI), which may be administered in accordance with the present invention using an infusion catheter, such as produced by C. R. Bard Inc., Billerica, Mass., or that disclosed by Wolinsky (U.S. Pat. No. 4,824,436) or Spears (U.S. Pat. No. 4,512,762), a therapeutically/prophylactically effective dosage of the compounds of formula (VI) will be typically reached when the concentration thereof in the fluid space between the balloons of the catheter is in the range of about $10^{-3}$ to $10^{-12}$ M. The compounds of formula (VI) may only need to be delivered in an anti-proliferative therapeutic/prophylactic dosage sufficient to expose the proximal (6 to 9) cell layers of the intimal or tunica media cells lining the lumen thereto. Also, such a dosage can be determined empirically, e.g., by a) infusing vessels from suitable animal model systems and using immunohistochemical methods to detect the compound of formula (VI) and its effects; and b) conducting suitable in vitro studies.

Local delivery by an implant involves the surgical placement of a matrix that contains the therapeutic agent at the lesion site or traumatized area The implanted matrix releases the therapeutic agent by diffusion, chemical reaction, or solvent activators. Lange, Science, 249, 1527 (1990).

An example of targeted local delivery by an implant is the use of a stent. Stents are designed to mechanically prevent the collapse and reocclusion of the coronary arteries. Incorporating a therapeutic agent into the stent delivers the therapeutic agent directly to the lesion. Local delivery of agents by this technique is described in Koh, Pharmaceutical Technology (October, 1990).

For example, a metallic, plastic or biodegradable intravascular stent can be employed which comprises an effective amount of a therapeutic agent. The stent preferably comprises a biodegradable coating or a porous or permeable non-biodegradable coating comprising the therapeutic agent. A more preferred embodiment of the invention is a coated stent wherein the coating comprises a sustained-release dosage form of the therapeutic agent. In an alternative embodiment, a biodegradable stent may also have the therapeutic agent impregnated therein, i.e., in the stent matrix.

A biodegradable stent with the therapeutic agent impregnated therein can further be coated with a biodegradable coating or with a porous non-biodegradable coating having the sustained release-dosage form of the therapeutic agent dispersed therein. Such a stent can provide a differential release rate of the therapeutic agent, i.e., there can be a faster initial release of the therapeutic agent from the coating followed by a slower delayed release of the therapeutic agent impregnated in the stent matrix, upon degradation of the stent matrix. The intravascular stent also provides a mechanical means of providing an increase in luminal area of a vessel.

Furthermore, the placement of intravascular stents comprising a therapeutic agent which is an inhibitor of smooth muscle cell proliferation can provide increased efficacy by reducing or preventing intimal proliferation. This inhibition of intimal smooth muscle cells and stroma produced by the smooth muscle and pericytes can allow more rapid and complete re-endothelization following the intraventional placement of the vascular stent. The increased rate of re-endothelization and stabilization of the vessel wall following stent placement can reduce the loss of luminal area and decreased blood flow which is the primary cause of vascular stent failures.

Another example is a delivery system in which a polymer that contains the therapeutic agent is injected into the lesion in liquid form. The polymer then solidifies or cures to form the implant which is retained in situ. This technique is described in published PCT application WO 90/03768 (Donn, Apr. 19, 1990).

Another example is the delivery of a therapeutic agent by polymeric endoluminal sealing. This technique uses a catheter to apply a polymeric implant to the interior surface of the lumen. The therapeutic agent incorporated into the biodegradable polymer implant is thereby released at the surgical site. This technique is described in published PCT application WO 90/01969 (Schindler, Aug. 23, 1989), the disclosure of which is incorporated by reference herein.

Yet another example of local delivery by an implant is by direct injection of vesicles or microparticulates into the lesion. These microparticulates may be composed of substances such as proteins, lipids, carbohydrates or synthetic polymers. These microparticulates have the therapeutic agent incorporated throughout the microparticle or over the microparticle as a coating. Delivery systems incorporating microparticulates are described in Lange, Science, 249,1527 (1990) and Mathiowitz et al., J. App. Poly. Sci., 26, 809 (1981).

Local delivery by site specific carriers involves attaching the therapeutic agent to a carrier which will direct the therapeutic agent to the target site, i.e., to a proliferative lesion. Examples of this delivery technique includes the use of carriers such as a protein ligand, e.g., a monoclonal antibody or antibody fragment. Lange, *Science,* 249, 1527 (1990).

Local delivery by direct application also includes applying the therapeutic agent directly to tissue, such as to the arterial bypass graft during the surgical procedure, or an artificial graft, and then implanting the treated graft or other tissue.

For topical administration, the therapeutic agents may be formulated as is known in the art for direct application to a target area. Conventional forms for this purpose include wound dressings, coated bandages or other polymer coverings, ointments, lotions, pastes, jellies, sprays, and aerosols. The percent by weight of a therapeutic agent of the invention present in a topical formulation will depend on various factors, but generally will be from 0.5% to 95% of the total weight of the formulation, and typically 1–25% by weight.

It will be recognized by those skilled in the art that therapeutically/-prophylactically effective dosages of these therapeutic agents and compositions will be dependent on several factors. For example, with respect to catheter delivery, those factors include a) the atmospheric pressure applied during infusion; b) the time over which the agent administered resides at the vascular site; c) the form of the therapeutic or prophylactic agent employed; and/or d) the nature of the vascular trauma and therapy desired. Those skilled practitioners trained to deliver drugs at therapeutically or prophylactically effective dosages (e.g., by monitoring drug levels and observing clinical effects in patients) will determine the optimal dosage for an individual patient based on experience and professional judgment. Those skilled in the art will recognize that infiltration of the therapeutic agent into intimal layers of a diseased or traumatized human vessel wall in free or sustained-release form is subject to variation and will need to be determined on an individual basis.

A further aspect of the invention provides a method of treating a mammal having, or at risk of, an indication associated with a TGF-beta deficiency comprising administering an amount of an aspirinate effective to elevate the level of TGF-beta.

A further aspect of the invention provides a method of treating a mammal having, or at risk of, a vascular indication which is associated with a TGF-beta deficiency, comprising administering an amount of an aspirinate effective to elevate the level of TGF-beta so as to inhibit or reduce the diminution of vessel lumen diameter. Specifically, the administration is effective to reduce or prevent lipid accumulation by the vessel, to increase plaque stability of an atherosclerotic lesion, to inhibit atherosclerotic lesion formation or development, or to induce atherosclerotic lesion regression.

A further aspect of the invention provides a method of treating a mammal having, or at risk of, an indication associated with a TGF-beta deficiency other than hypertension, thrombosis or atherosclerosis, comprising administering an amount of 3-acetoxy-2-carboxythiophene or a pharmaceutically acceptable salt thereof, effective to elevate the level of TGF-beta.

A further aspect of the invention provides a therapeutic method for preventing or treating a condition or symptom associated with Parkinson's disease, Marfan's syndrome, Alzheimer's disease, senile dementia, osteoporosis, multiple sclerosis, lupus erythermatosis, or fibrosis, comprising administering to a mammal in need of such therapy, an effective amount of an aspirinate.

A further aspect of the invention provides a therapeutic method for preventing or treating a condition or symptom associated with an auto-immune disease, comprising administering to a mammal in need of such therapy, an effective amount of an aspirinate, provided the aspirinate is not a copper salt of an aryl or heteroaryl carboxylic acid.

A further aspect of the invention provides a therapeutic method for lowering serum cholesterol, comprising administering to a mammal in need of such therapy, an effective amount of an aspirinate.

A further aspect of the invention provides a therapeutic method for enhancing or promoting wound healing, comprising administering to a mammal in need of such therapy, an effective amount of an aspirinate.

A further aspect of the invention provides a kit comprising, separately packaged, a device adapted for the local delivery of an agent to a site in the lumen of a vessel of a mammal, and at least one unit dosage form of an aspirinate, wherein the aspirinate is effective to maintain or elevate the TGF-beta levels in said mammal.

A further aspect of the invention provides a method of preventing or treating a mammal having, or at risk of developing, atherosclerosis, comprising administering an amount of a combination of aspirin or an aspirinate and at least one omega-3 fatty acid, wherein said amount is effective to maintain or increase the level of TGF-beta so as to inhibit or reduce vessel lumen diameter diminution.

A further aspect of the invention provides a pharmaceutical composition comprising: (a) an amount of a first agent effective to elevate the level of latent TGF-beta; and (b) an amount of a second agent effective to increase the level of TGF-beta which is capable of binding to the TGF-beta receptors.

A further aspect of the invention provides a pharmaceutical composition comprising: (a) an aspirinate; and (b) at least one omega-3 fatty acid; wherein components (a) and (b) are present in a combined amount effective to maintain or elevate TGF-beta levels when the composition is administered to a mammal.

A further aspect of the invention provides a kit comprising, separately packaged, a unit dosage form of a first agent effective to elevate the level of latent TGF-beta in a mammal, a unit dosage form of a second agent effective to increase the level of TGF-beta which is capable of binding to the TGF-beta receptors in said mammal, and a device adapted for the local delivery of at least one of said agents.

A further aspect of the invention provides a kit comprising, separately packaged, a device adapted for the local delivery of at least one agent to a site in the lumen of a mammalian vessel and at least one unit dosage of aspirin or an aspirinate and at least one unit dosage of at least one omega-3 fatty acid, and wherein either or both unit dosages are effective to maintain or elevate TGF-beta levels.

A further aspect of the invention provides a therapeutic method comprising: (a) identifying a patient exhibiting a decreased level of active TGF-beta and afflicted with a pathology associated with said decreased level; and (b) administering to the patient an agent that elevates the level of TGF-beta which is capable of binding to the TGF-beta receptors so as to alleviate at least one of the symptoms of said pathology.

A further aspect of the invention provides a method comprising determining endothelial cell activation in a mammal by detecting immunoglobulins that specifically bind to a TGF-β Type II receptor or a portion thereof.

A further aspect of the invention provides a method comprising diagnosing or monitoring a disease characterized by endothelial cell activation in a mammal by detecting immunoglobulins that specifically bind to a TGF-β Type II receptor or a portion thereof.

A further aspect of the invention provides a method comprising diagnosing or monitoring atherosclerosis in a mammal by detecting immunoglobulins that bind to a TGF-β Type II receptor or a portion thereof.

Specifically, in the above methods, immunoglobulins can be detected by: (a) combining a physiological fluid from the mammal which comprises the immunoglobulins, with a capture moiety that binds the immunoglobulins, forming a capture complex comprising the capture moiety and the immunoglobulins; and (b) detecting or determining the amount of the capture complex. The capture moiety can be immobilized. The capture moiety can comprises a TGF-β Type II receptor or a portion thereof. The capture moiety can comprises the extracellular domain of the TGF-β Type II receptor. The immunoglobulins can comprise anti-TGF-β Type II receptor-IgG antibodies. The immunoglobulins can comprise anti-TGF-β Type II receptor-IgD antibodies. The signal moiety can comprises anti-human-pan-IgG antibodies. The signal moiety can comprise anti-human-IgG2 subclass specific antibodies. The signal moiety can comprise anti-human-IgD antibodies. The physiological fluid can be serum, or plasma. The mammal can be a human. The immunoglobulins can bind to the extracellular domain of the TGF-β Type II receptor. The immunoglobulins can comprise IgG antibodies. And, a signal moiety comprising a detectable label can detect the complex.

A further aspect of the invention provides a method comprising detecting mammalian cells having TGF-β Type II receptors, by combining the cells with a capture moiety that binds TGF-β type II receptors or a portion thereof, forming a capture complex; and detecting or determining the amount of the capture complex. The method may optionally further comprising comparing the amount with a standard curve referenced to a pool of normal cells of tissue. The capture moiety can comprises immunoglobulins. The immunoglobulins can bind to the extracellular domain of the TGF-β Type II receptor. The immunoglobulins can comprise IgG antibodies. The immunoglobulins can comprise IgG antibodies. Specifically, a signal moiety comprising a detectable label can detect the capture complex; the signal moiety can comprise anti-human-pan-IgG antibodies, anti-human-IgG2 subclass specific antibodies, or anti-human-IgD antibodies; and the cells can be brachial cells or femoral cells.

A further aspect of the invention provides a method comprising diagnosing or monitoring atherosclerosis in a mammal by detecting TGF-β type II receptors in cells or tissue of the mammal.

A further aspect of the invention provides a kit comprising packaging material containing: a) a capture moiety comprising the extracellular domain of the TGF-β Type II receptor; and b) a detection moiety capable of binding to an immunoglobulin. Specifically, the immunoglobulin can be IgG, or IgD.

The invention will be better understood by making reference to the following specific examples.

EXAMPLE I

Association of TGF-beta with Lipoprotein Particles

TGF-beta is a hydrophobic protein known to have affinity for polymeric aliphatic hydrocarbons. To determine whether TGF-beta would associate with lipoprotein particles in the circulation, platelet-poor plasma was prepared from peripheral venous blood drawn from ten healthy donors (A–J) and two donors with diabetes (K and L). The absence of platelet degranulation (<0.02% degranulation) was confirmed by measurement of PF4 (platelet factor-4) in the plasma by ELISA (Asserchrom PF4; Diagnostic Stago, FR). A 1 ml aliquot of plasma was diluted to 4 ml with Buffer A (Havel et al., *J. Clin. Investig.*, 34, 1345 (1955)) and then KBr was added to final density of 1.215 g/ml. The lipoproteins were separated from the plasma proteins by density gradient ultracentrifugation (235,000×g) at 4° C. for 48 hours. The top 2 ml was collected as the lipoprotein fraction and the lower 2 ml was collected as the lipoprotein deficient plasma fraction.

The total cholesterol in each fraction was measured by the cholesterol oxidase enzymatic method (Sigma Diagnostics) as previously described in Grainger et al., *Nat. Med.*, 1, 1067 (1995). The cholesterol in fractions 0–9 was assumed to be VLDL, in fractions 10–19 to be LDL, and in factions 20–30 to be HDL, in accordance with the elution positions of the major apolipoproteins. Lipoprotein concentrations are reported as mM cholesterol. For cell cultures studies, the lipoprotein fraction was subjected to extensive dialysis against serum-free DMEM, and the amount of TGF-beta was measured in the lipoprotein fraction and in the plasma protein fractions after treatment with acid/urea, using the Quantikine ELISA R&D Systems) in accordance with the manufacturer's instructions, In some individuals (7/10), TGF-beta was detected in the lipoprotein fraction as well as the lipoprotein deficient plasma fraction. The proportion of the TGF-beta associated with lipoprotein varied from <1% to 39% with a mean of 16%. Thus, plasma TGF-beta, unlike most other plasma proteins, can associate with lipoprotein particles.

TABLE 1

| Individual | Age (yrs) | Sex | % associated TGF-beta | VLDL | LDL (mM) | HDL |
|---|---|---|---|---|---|---|
| A | 44 | M | 27 | 0.9 | 3.1 | 0.8 |
| B | 28 | M | <1 | 0.5 | 2.8 | 1.1 |
| C | 41 | F | 24 | 1.1 | 4.7 | 0.7 |
| D | 31 | M | <1 | 0.6 | 3.4 | 0.8 |
| E | 28 | M | 7 | 0.3 | 3.0 | 0.9 |
| F | 21 | F | 19 | 1.1 | 2.6 | 1.0 |
| G | 22 | M | 11 | 0.8 | 3.6 | 0.9 |
| H | 49 | M | 39 | 1.5 | 3.3 | 1.0 |
| I | 47 | M | <1 | 0.8 | 3.7 | 0.8 |
| J | 29 | M | 9 | 0.9 | 3.1 | 1.0 |
| K | 36 | M | 78 | 4.6 | 3.1 | 0.9 |
| L | 27 | M | 96 | 1.1 | 3.8 | 1.1 |

To determine whether the TGF-beta associated with lipoprotein particles was able to bind to the type II TGF-beta signaling receptor and exert biological activity in vitro, the binding of recombinant TGF-beta to R2X was measured in the absence and presence of increasing concentrations of lipoprotein purified from the plasma of an individual with <1 ng/ml TGF-beta in plasma (individual I, Table 1). If the lipoprotein-associated fraction of TGF-beta is unavailable for binding, lipoproteins prepared from an individual with a very low plasma concentration of TGF-beta would be expected to reduce the binding of recombinant active TGF-beta to its receptors. The half maximal (ka) binding of recombinant TGF-beta to the recombinant extracellular domain of the type II TGF-beta receptor was previously determined to be 17±3 ng/ml (R2X; Grainger et al., *Nature*, 270, 460 (1994); Grainger et al., *Clin. Chim. Acta*, 235, 11 (1995)).

To measure the binding of TGF-beta to its receptor, the recombinant extracellular domain of the type II TGF-beta receptor (R2X), was coated onto ELISA plates (1 μg/well, Maxisorp plates, Gibco BRL). Wells were washed 3 times quickly in TBS and blocked with TBS containing 3% bovine serum albumin (BSA, fatty-acid free; Sigma) for 30 minutes. A standard curve of recombinant active TGF-beta1 (1.5 ng/ml to 100 ng/ml recombinant active TGF-beta1 in two fold serial dilutions; R&D Systems) was prepared in TBS+ 0.1% BSA and in TBS+0.1% BSA additionally containing dialyzed lipoprotein at various concentrations. The standard curves were incubated in the wells containing R2X for 2 hours. The amount of bound TGF-beta was detected with antibody BDA5 (R&D Systems) as previously described by Grainger et al., *Clin. Chim. Acta,* 235, 11 (1995). Briefly, after three quick washes with TBS, the wells were incubated with TGF-beta detection antibody at 1 μg/ml in TBS+3% BSA (50 μl/well) for 1 hour. After a further three washes in TBS, the wells were incubated with anti-rabbit IgG conjugated to horseradish peroxidase (A-6154; Sigma) at 1:5000 dilution in TBS+3% BSA for 30 minutes. The wells were washed 3 times with TBS and visualized using K-Blue Substrate (Elisa Technologies) for 20 minutes. All incubations were performed at room temperature with shaking (~300 rpm).

Figure 2A:
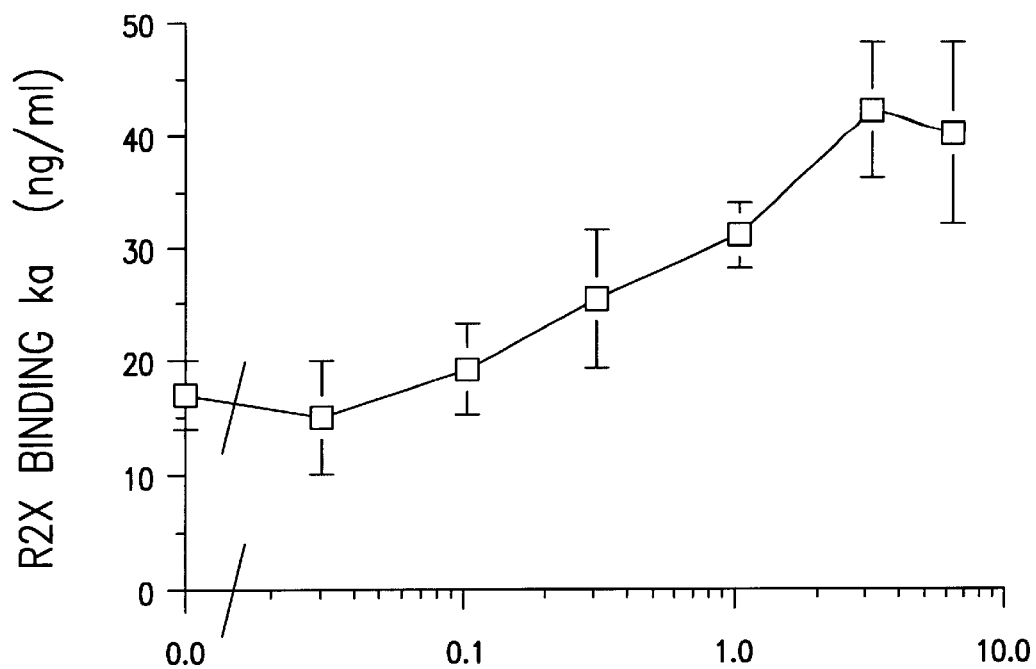
FIG. 2 depicts the association of increasing amounts of lipoprotein with (A) a reduction in TGF-beta binding to the TGF-beta receptor (R2X); and (B) an increasing amount of TGF-beta necessary to half maximally inhibit mink lung cell proliferation.

The presence of lipoprotein caused a dose-dependent increase in the apparent ka for TGF-beta binding to R2X to a maximal value of 42±6 ng/ml when lipoprotein equivalent to 3 mM total cholesterol was added (FIG. 2A; values are the mean±standard error of triplicate determinations). The concentration of lipoprotein (measured as total cholesterol) which half-maximally increased the apparent ka was approximately 1 mM. Thus, TGF-beta which is associated with lipoprotein particles has a lower affinity for the type II TGF-beta receptor, or, if the TGF-beta is in equilibrium between the lipoprotein and aqueous phases, is unable to bind to the TGF-beta receptors.

Figure 2B:
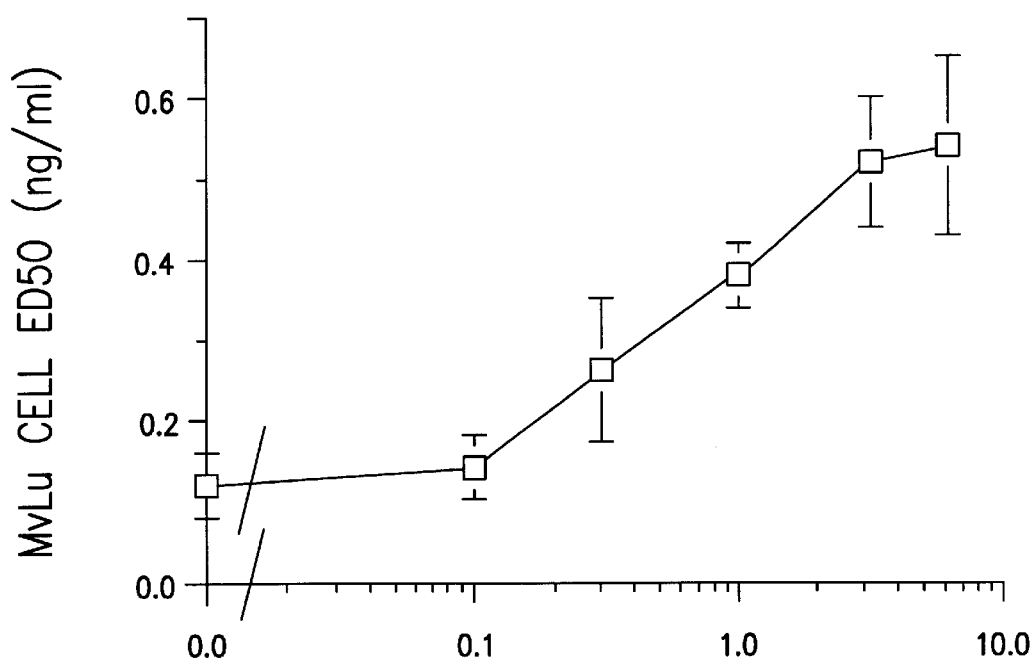

It has previously been shown that TGF-beta inhibits the proliferation of mink lung epithelial (MvLu) cells in culture. Recombinant active TGF-beta1 was added to MvLu cells (passage 59–63 from the ATCC) which were growing in DMEM+10% fetal calf serum) and the concentration of recombinant TGF-beta required to half-maximally inhibit MvLu cells (reported as MvLu cell $ID_{50}$) was measured as previously described (Danielpour et al., *J. Cell Physiol.,* 18, 79 (1989); Kirschenlohr et al., *Am. J. Physiol.,* 265, C571 (1993). Proliferation of MvLu cells was half-maximally inhibited by recombinant active TGF-beta1 with an $ID_{50}$ of 0.12±0.04 ng/ml (n=6) (FIG. 2B). Addition of lipoprotein purified from the plasma of individual I caused a dose-dependent increase in the $ID_{50}$ of TGF-beta. The $ID_{50}$ was maximal at 0.52±0.08 ng/ml when 3 mM total cholesterol was added. The concentration of lipoprotein which half-maximally increased the $ID_{50}$ was approximately 0.8 mM. Therefore, TGF-beta associated with lipoprotein was less active, or inactive, as an inhibitor of MvLu cell proliferation.

Since low levels of TGF-beta activity have been associated with advanced atherosclerosis, individuals with a large proportion of their plasma TGF-beta sequestered into an inactive lipoprotein-associated pool may be at significantly higher risk of developing the disease. The differences in the proportion of TGF-beta associated with lipoprotein among the individuals studied were therefore investigated further. The different classes of lipoprotein were separated by size using gel filtration chromatography for ten healthy individuals A–J (Table 1) as well as two diabetic individuals with abnormal lipoprotein profiles (individuals K–L, Table 1). The TGF-beta present in the fractions following the gel filtration of the lipoprotein fraction from each of the ten individuals was then determined.

Figure 3A:
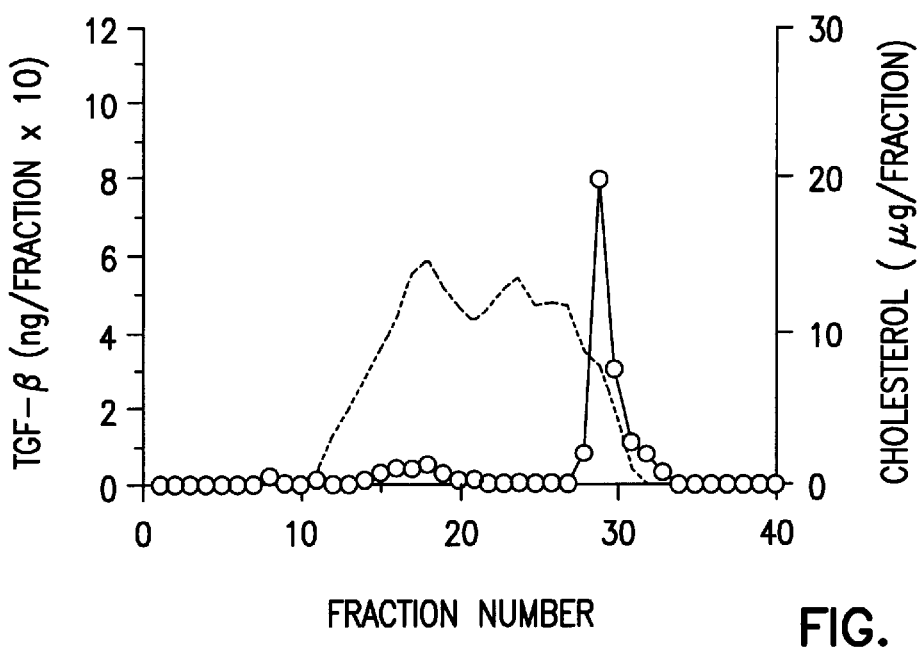
FIG. 3 depicts the association of TGF-beta with different lipoprotein classes. Profile of lipoprotein particle elution measured as total cholesterol ( . . . ) and TGF-beta elution (open circles) following separation of the lipoprotein fraction (d<1.215 g/cm$^3$) by gel filtration chromatography. The position of the major lipoprotein classes are marked by reference to the elution times of the major apolipoproteins. (a) Healthy individual A (b) Healthy individual C (c) Diabetic individual K (d) Diabetic individual L. Letters designating the individuals shown refer to individuals in Table 1.

Individual A had a profile of lipoproteins typical of healthy subjects (FIG. 3A) and 27% of the plasma TGF-beta was associated with the lipoprotein fraction. 88% of the lipoprotein-associated TGF-beta eluted with a tightly defined subfraction of the HDL particles, with the smallest size of all the cholesterol-containing lipoprotein particles. The remaining 12% of the lipoprotein-associated TGF-beta was distributed among the VLDL and LDL fractions. This pattern of association of TGF-beta with a subfraction of HDL particles was typical of all the health donors tested (>80% of the lipoprotein-associated TGF-beta in a subtraction of HDL), except individual C.

Figure 3B:
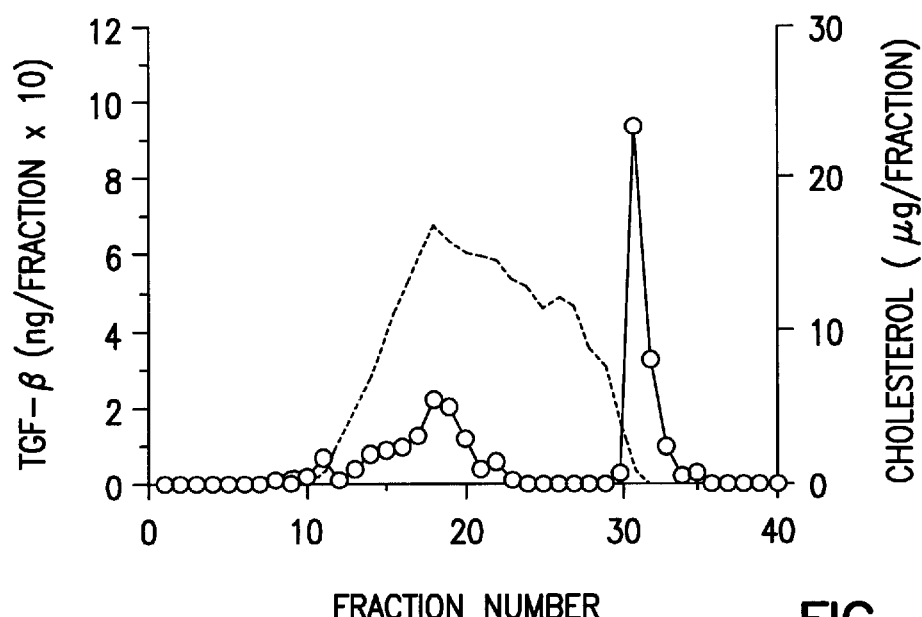

Individual C had little VLDL or chylomicrons but moderately elevated LDL and 24% of the plasma TGF-beta was associated with the lipoprotein pool (FIG. 3B). As with the other individuals the majority (65%) of the TGF-beta was associated with the HDL subtraction. However, this individual had a significant amount of TGF-beta (27%) associated with LDL and the remainder eluted with the VLDL.

Figure 3C:
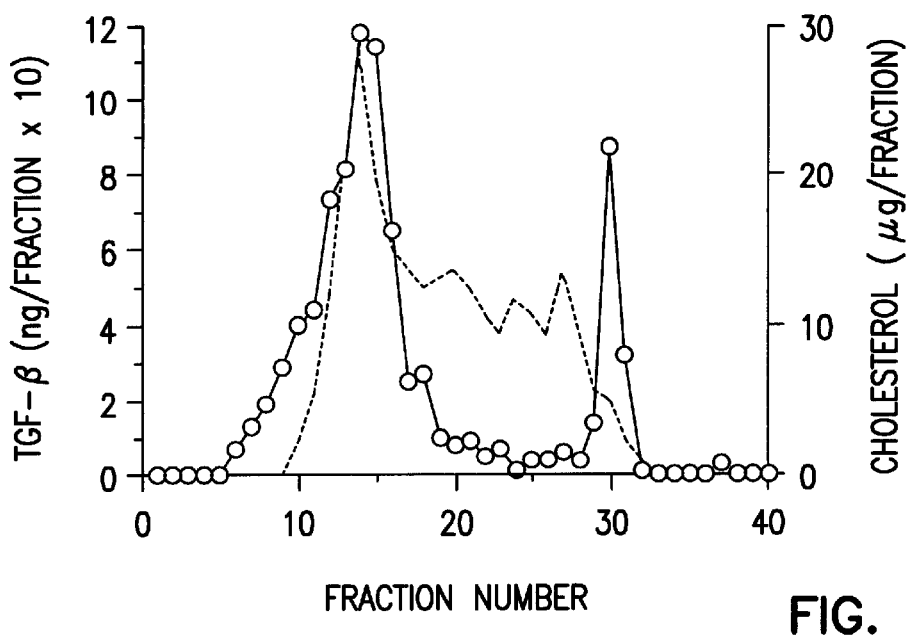

Individual K was a diabetic patient with hypertriglyceridaemia, and >50% of the total plasma cholesterol was present in the largest triglyceride-rich lipoprotein particles (FIG. 3C). This individual had 78% of the plasma TGF-beta associated with the lipoprotein pool, but only 20% of this was present in the HDL subfraction. The remaining 80% co-eluted from the gel filtration column with the VLDL and chylomicrons.

Figure 3D:
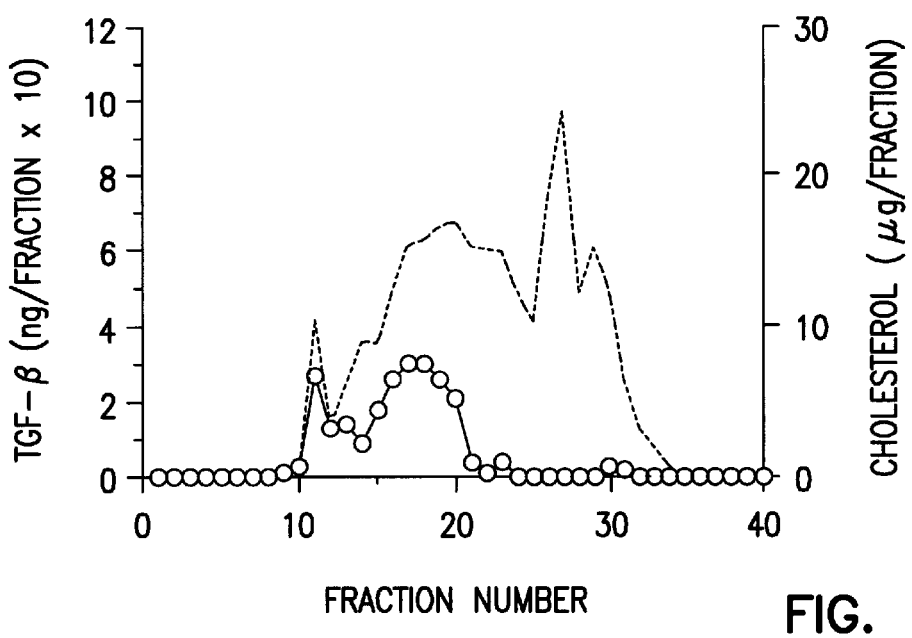

Individual L was a diabetic patient with moderately elevated plasma triglyceride and VLDL/chylomicrons and 92% of the plasma TGF-beta associated with the lipoprotein (FIG. 3D). This individual had very little (<5%) of the lipoprotein-associated TGF-beta co-eluting with the HDL particles. Approximately 60% of the TGF-beta co-eluted with the largest triglyceride-rich lipoprotein particles and the remainder with the LDL particles.

Figure 10A:
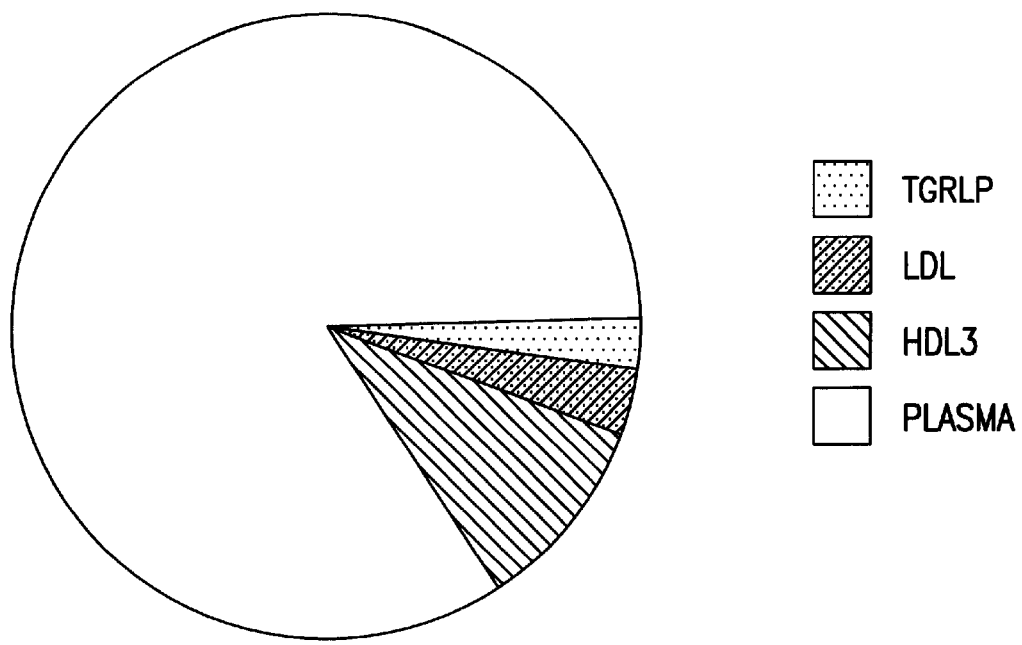
FIG. 10 depicts the distribution of TGF-beta between the plasma (open segment) and various lipoprotein fractions at baseline (a) and after 8 hours during a fat tolerance test (b).
Figure 10B:
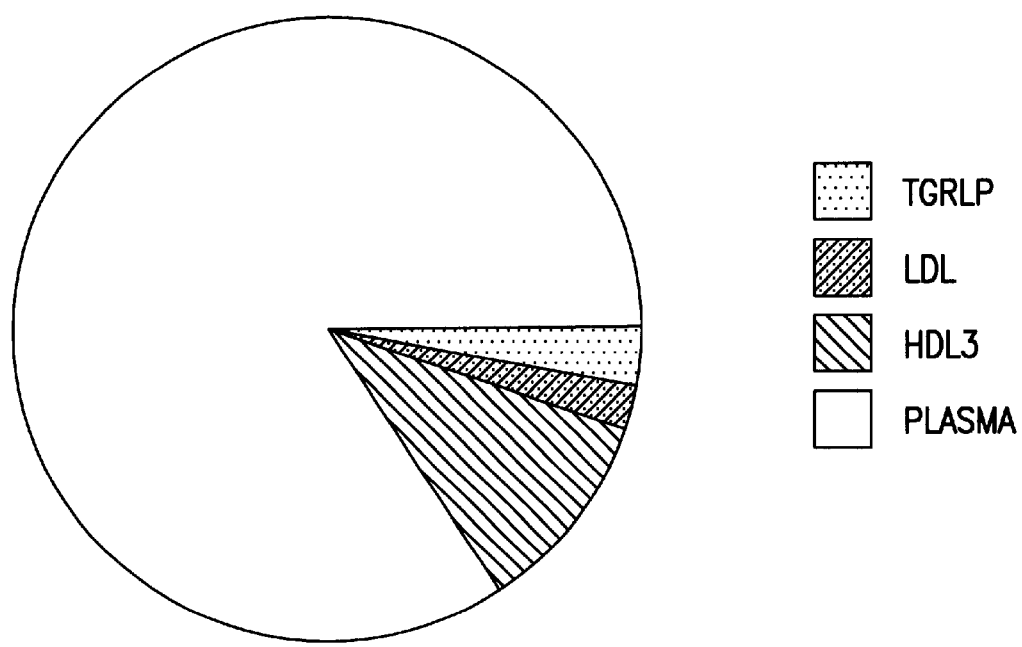
Figure 11:
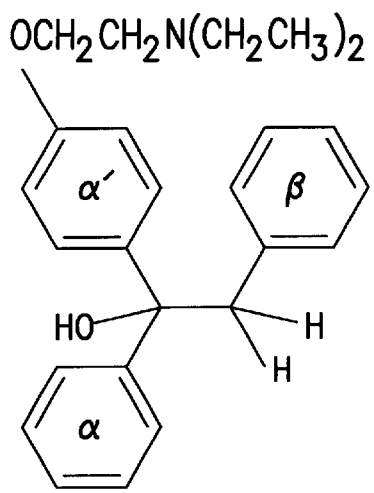
FIG. 11 shows the structure of the compounds MER25, zindoxifene, DDAC (Analog II), and DTAC (102b).
Figure 11:
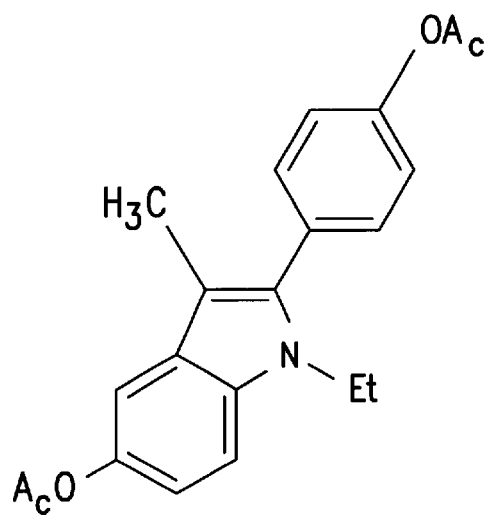
Figure 11:
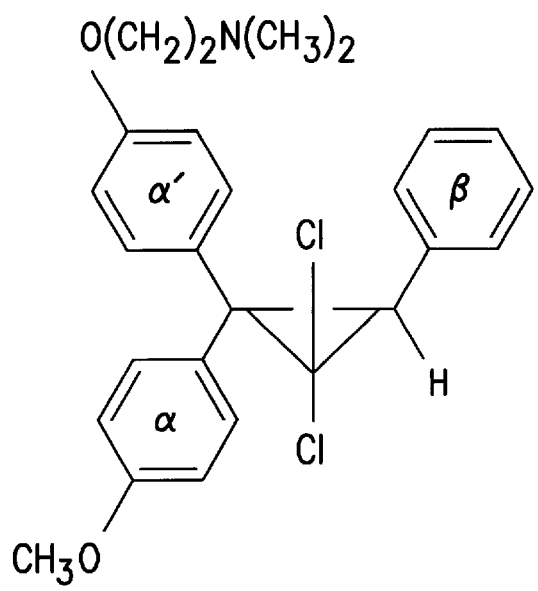
Figure 11:
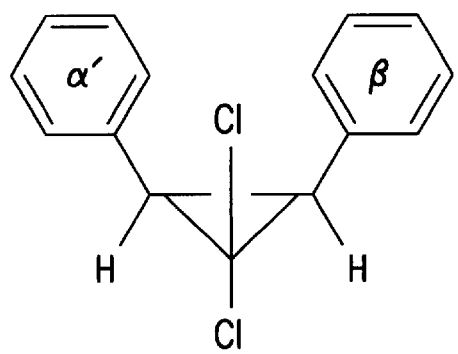

Thus, TGF-beta associates with a subtraction of HDL particles which vary very little in size and which are among the smallest cholesterol-containing lipoproteins present in plasma. Additionally, TGF-beta can associate with both the triglyceride-rich LDL and VLDL particles (FIG. 10). Indeed, under conditions where the concentrations of these particles in plasma is elevated, e.g., in diabetic subjects or patients with hypercholesterolaemia or hypertriglyceridaemia, these particles can become the major lipoprotein fraction responsible for binding TGF-beta.

Diabetic individuals, particularly those with poor glucose control, often exhibit elevated plasma concentrations of the triglyceride-rich lipoprotein particles. Such individuals may therefore have an increased fraction of their plasma TGF-beta associated with the lipoprotein pool, since they may have a major fraction of their plasma TGF-beta associated with the triglyceride-rich lipoprotein particles as well as the subfraction of HDL particles.

The proportion of TGF-beta in the lipoprotein fraction for ten diabetic individuals who exhibited poor glucose control was determined (Haemoglobin a1C>8.0). These individuals had moderately elevated total plasma triglyceride levels (2.34±0.70 mM compared to 1.43±0.60 mM in healthy control donors; n=10; p<0.07 Student unpaired t-test), and the proportion of TGF-beta associated with lipoprotein was markedly increased (68±21% compared to 16±11% in healthy control donors; mean±standard deviation; n=10; p<0.05 Mann-Whitney unpaired U-test). Therefore, diabetic individuals with poor glucose control have significantly more of the plasma TGF-beta sequestered into the lipoprotein pool where it is less active or inactive.

EXAMPLE II

Effect of Dietary Fish Oil on the Association of TGF-beta with Lipoprotein

To determine whether dietary supplementation with fish oil would reduce the association of plasma TGF-beta with the lipoprotein fraction, platelet-poor plasma was prepared from 33 donors prior to, and immediately following, four weeks of dietary supplementation with 2.4 g/day fish oil (Wallace et al., *Arterial Thromb. Vasc. Biol.,* 15, 185 (1995)). A further plasma sample was prepared nine weeks after ceasing the supplementation. The fraction of TGF-beta associated with the lipoprotein pool was determined for each plasma sample.

Figure 4:
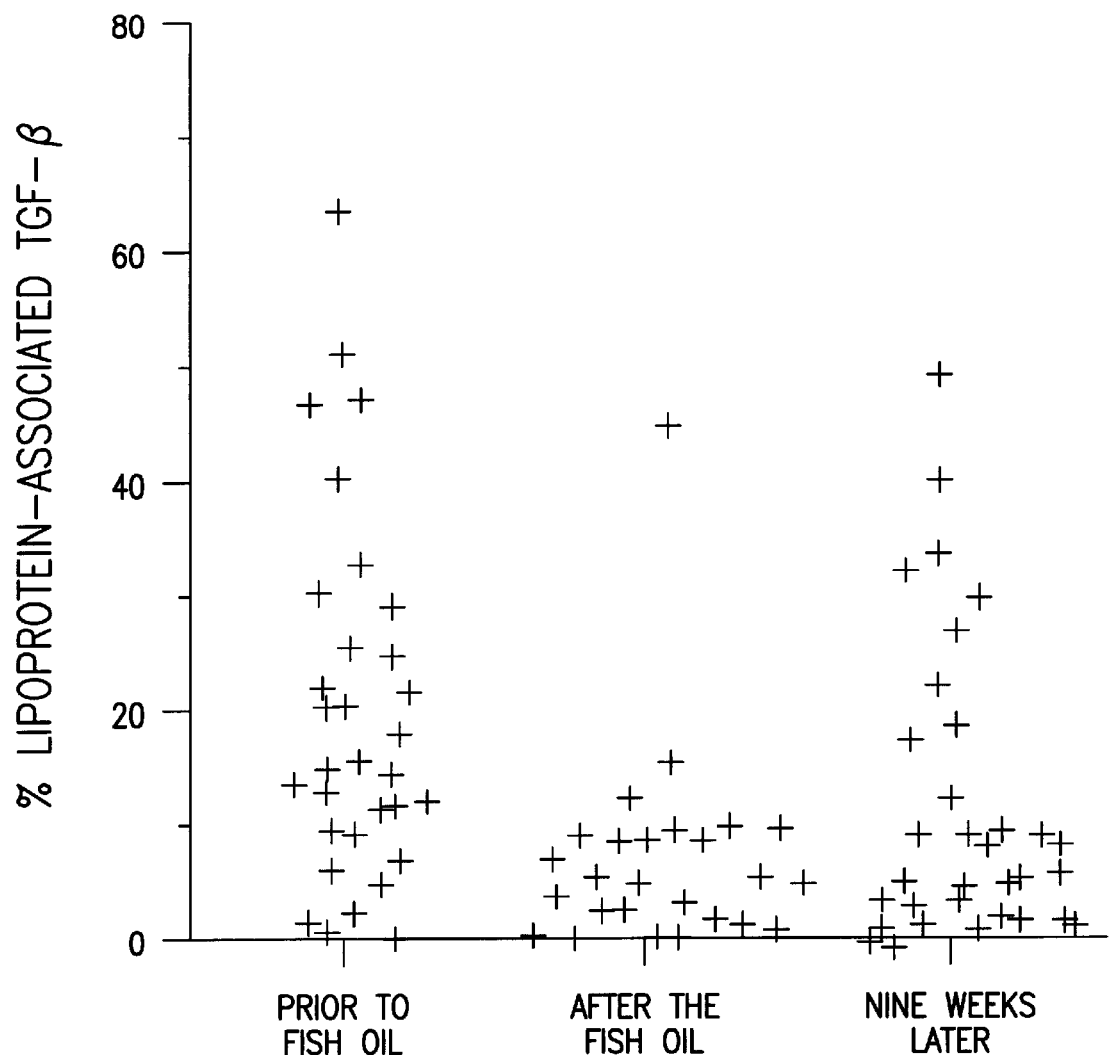
FIG. 4 depicts the effect of fish oil therapy on the association of TGF-beta with lipoprotein. Platelet-poor plasma was prepared from 36 individuals prior to receiving fish oil, after 4 weeks of dietary supplementation with 2.4 g/day fish oil and then after 9 weeks with no fish oil supplementation.

At the end of the four week supplementation period total plasma triglyceride concentrations were somewhat reduced although total plasma cholesterol was unaffected (FIG. 4; Table 2). Fish oil supplementation also markedly reduced TGF-beta association with the lipoprotein fraction. The mean proportion of TGF-beta associated with lipoprotein was reduced from 19±10% (range<1% to 62%) to 7±4% (range<1% to 41%; p<0.01; paired Wilcoxon signed-rank test). After a further nine weeks without fish oil supplementation of the diet, triglycerides had returned to baseline and the proportion of TGF-beta associated with the lipoprotein pool had increased to 13±9%, although it had not returned to the baseline.

Consistent with the decrease in the fraction of TGF-beta sequestered into the inactive lipoprotein-associated pool, the concentration of active TGF-beta increased by 21% after four weeks of dietary supplementation with 2.4 g/day fish oil. The concentration of active TGF-beta was still significantly above baseline after a further 9 weeks after dietary supplementation, although the increase was less marked (+12%, p<0.05). Thus, increased dietary intake of fish oil reduces the fraction of plasma TGF-beta sequestered into the lipoprotein pool, and increases the concentration of active TGF-beta in plasma.

The reduction in sequestration may be due to the alteration of the proportion of different lipoproteins, i.e., fish oil reduces triglyceride rich lipoprotein levels, or by altering the composition and hence sequestering properties of lipoprotein. Thus, fish oil has no effect on the production of latent TGF-beta or mature TGF-beta but increases TGF-beta bioavailability by decreasing the lipoprotein sequestration of the TGF-beta. Such an effect would likely result in cardioprotection in individuals with adequate production of latent and mature TGF-beta but limited ability to release TGF-beta from lipoprotein complexes.

TABLE 2

| Time associated (weeks) | Fish oil supplementation | Total triglyceride (mM) | Total cholesterol (mM) | % TGF-beta |
|---|---|---|---|---|
| 0 | None | 1.43 ± 0.43 | 5.1 ± 1.2 | 19 ± 10 n = 32 |
| 4 | 2.4 g/day | 1.03 ± 0.57 | 5.3 ± 0.9 | 7 ± 4* n = 33 |
| 13 | None | 1.56 ± 0.50 | 5.3 ± 0.8 | 13 ± 9 n = 31 |

Table 2. Proportion of TGF-beta associated with lipid following dietary supplementation with fish oil. Total triglyceride concentration was measured by the glycerol kinase enzymatic method (Sigma Diagnostics). Total cholesterol and % associated TGF-beta were assayed as described in Example I. Values are mean±standard error. * p<0.01; paired Wilcoxon signed-rank test versus baseline.

EXAMPLE III

Aspirin Increases Circulating TGF-beta Levels

Aspirin has been suggested to have cardioprotective effects and is now in widespread use by patients diagnosed with coronary atherosclerosis. It has been demonstrated to significantly reduce the incidence of a second myocardial infarction (NH) in individuals who have previously suffered an MI. However, any benefit for the primary prevention of MI has not yet been demonstrated rigorously, although some studies have reported encouraging results.

A number of effects have been suggested to play a role in the cardioprotective benefits associated with chronic use of low-dose aspirin. Aspirin interferes with normal platelet function and increases the blood clotting time, while decreasing the stability of fibrin deposits. Since chronic formation of mural thrombi is thought to be important in the development of atherosclerosis and acute thrombus formation is the main cause of MI, the anti-platelet function of aspirin is thought to be important in mediating its cardioprotective effects. Moreover, since aspirin is a well-documented anti-inflammatory agent and atherosclerosis has an important inflammatory component, the anti-inflammatory action of aspirin could also contribute to cardioprotection.

In a study of 31 individuals with no detectable atherosclerosis by coronary angiography (NCA), the concentration of active plus acid-activatable latent (a+1) TGF-beta in serum was almost two-fold higher in those taking aspirin (300 mg per day for an average of 30 months) than those not. Thus the proportion of TGF-beta in the active form was not significantly altered, suggesting that aspirin may stimulate production of the latent TGF-beta precursor rather than stimulating its activation.

Figure 5A:
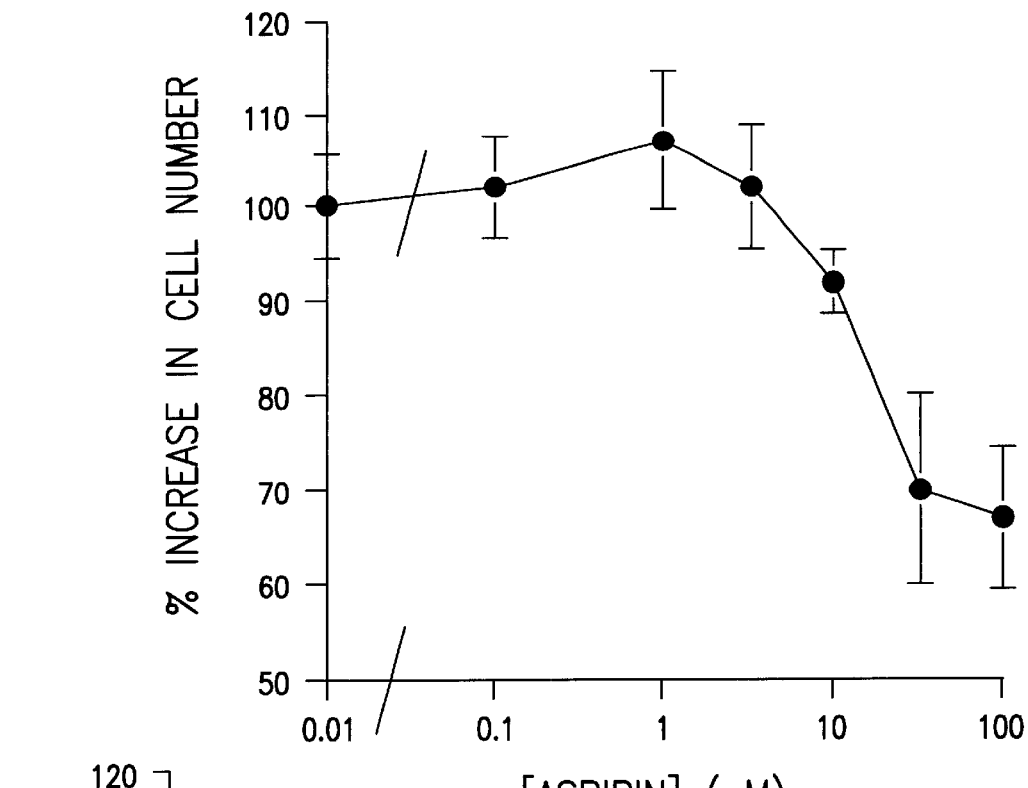
FIG. 5 depicts the effect of aspirin on vascular smooth muscle cells. A) Dose response curve showing the inhibitory effects of increasing amounts of aspirin on human vascular smooth muscle cell proliferation. B) Percent increase in cell number in treated versus untreated human vascular smooth muscle cells.

Agents associated with elevated circulating TGF-beta concentration in vivo have been shown to stimulate TGF-beta production by vascular smooth muscle cells (VSMCs) in culture. To determine whether aspirin could stimulate TGF-beta production by human VSMCs in culture, confluent cultures of human explant-derived VSMCs were subcultured into and grown for 24 hours in the presence of 10% FCS. The medium was then changed and triplicate wells were treated with either aspirin (from a stock solution dissolved in ethanol) or sodium aspirinate at various concentrations. The medium was replaced after 48 hours and after 96 hours the cells were released with trypsin and counted by haemocytometer. Tamoxifen (5 $\mu$M) was used as positive control, since it has previously been shown to stimulate TGF-beta production under similar conditions. Aspirin inhibited the proliferation of human VSMCs with half-maximal inhibition $ED_{50}$) at 12±3 $\mu$M (n=4), and maximally inhibited proliferation at 50 $\mu$M when the increase in cell number over 96 hours was inhibited by 33±6% (FIG. 5A). The effects of sodium aspirinate were not distinguishable from the effects of aspirin ($ED_{50}$=10 $\mu$M; n=2).

Figure 5B:
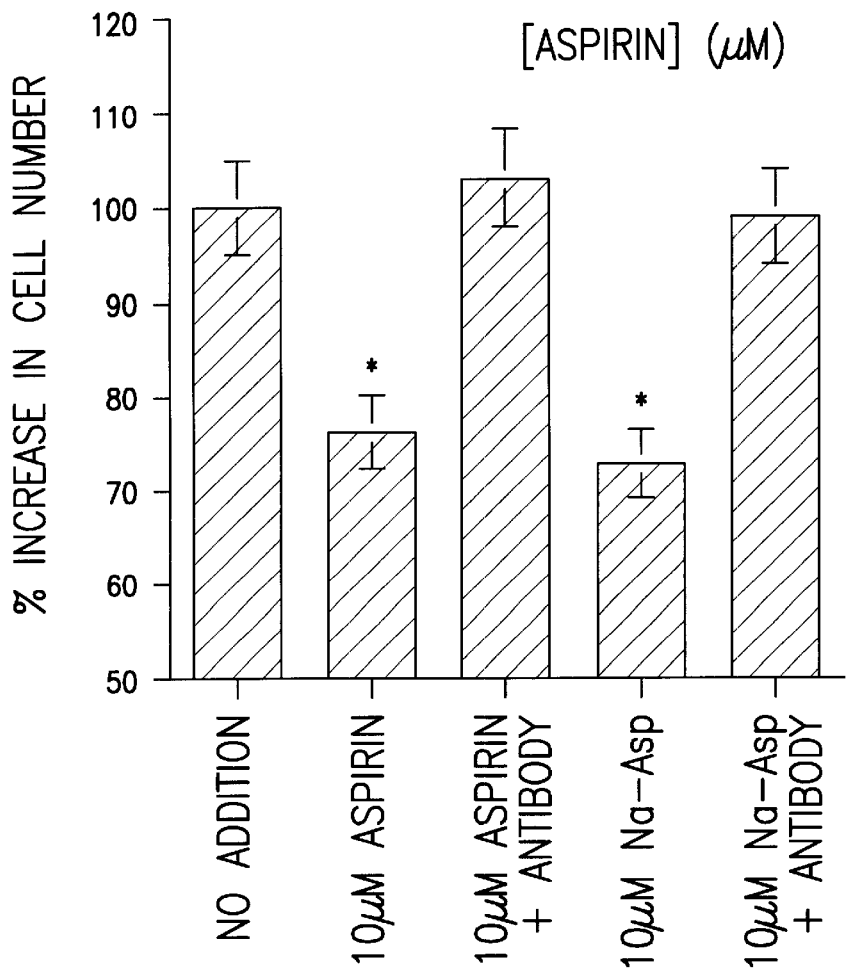

To demonstrate that the inhibition of proliferation by aspirin was due to TGF-beta production, subcultured human VSMCs were treated with 10 $\mu$M aspirin in the presence and absence of 25 $\mu$g/ml of a neutralizing antibody to TGF-beta. The presence of the antibody abolished (>95%; n=3) the growth inhibitory effects of aspirin and sodium aspirinate (>95%; n=2) (FIG. 5B).

The amount of TGF-beta present in medium conditioned on VSMCs in the presence and absence of aspirin was measured by ELISA. In the absence of aspirin, only 1.5±0.4 ng/ml TGF-beta was detected in the medium compared with 4.9±1.2 ng/ml (n=3; p<0.05; Students unpaired t test) after 96 hours in the presence of 10 µM aspirin. Thus, aspirin, like tamoxifen, stimulates production of TGF-beta by human VSMCs in culture, although the $ED_{50}$ for aspirin (12 µM) was markedly less potent than for tamoxifen (50 nM).

To evaluate the effect of aspirin administration on TGF-beta levels in vivo, the level of (a+1) TGF-beta or TGF-beta activity in the circulation of 42 patients with more than 50% stenoses of all three major coronary arteries (TVD) taking low-dose aspirin relative to individuals with normal coronary arteries (NCA) was determined. Platelet-poor plasma was prepared with minimal (<0.1% assessed by PF-4 release) platelet degranulation and active and (a+1) TGF-beta were measured by ELISA.

Figure 6A:
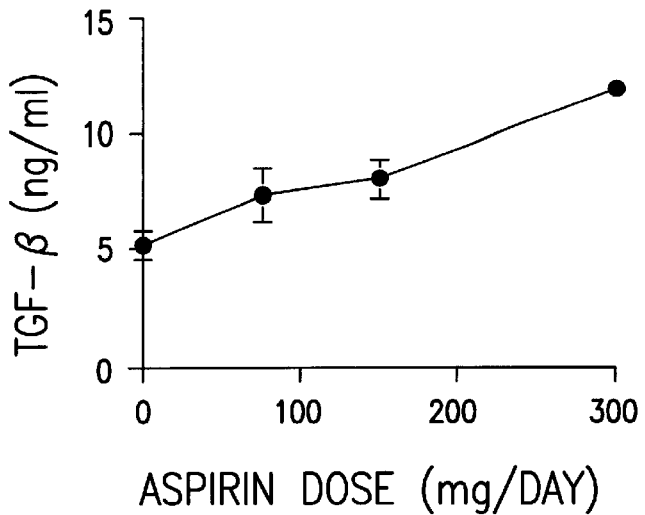
FIG. 6 depicts the relationship between TGF-beta concentration found in the sera of normal individuals (A), individuals with triple vessel disease (B) and both populations (C), who were undergoing aspirin therapy.
Figure 6B:
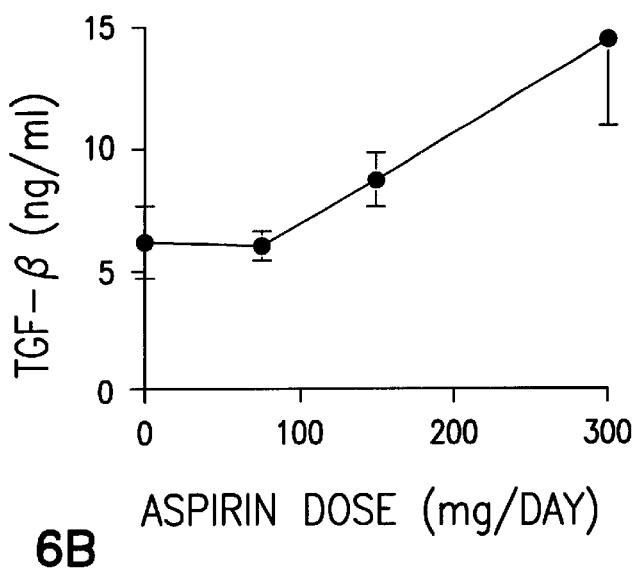
Figure 6C:
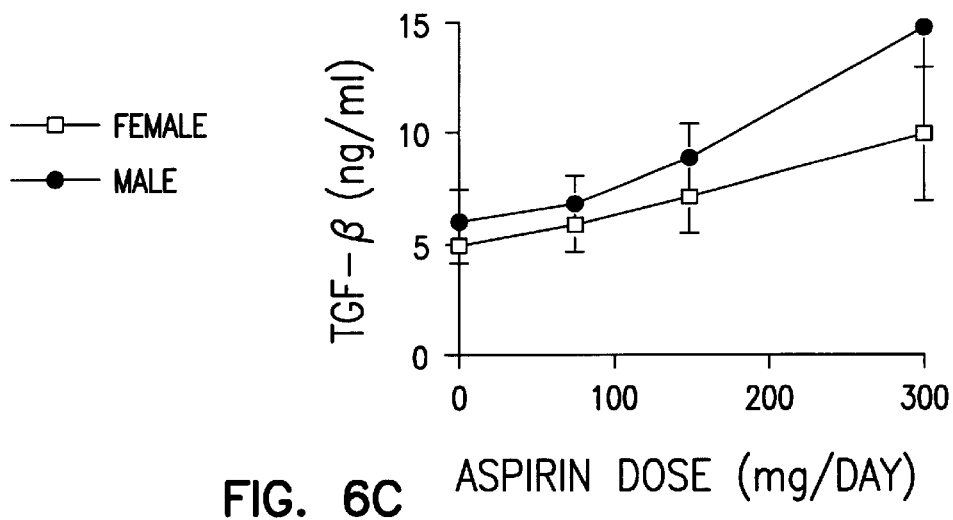
Figure 7:
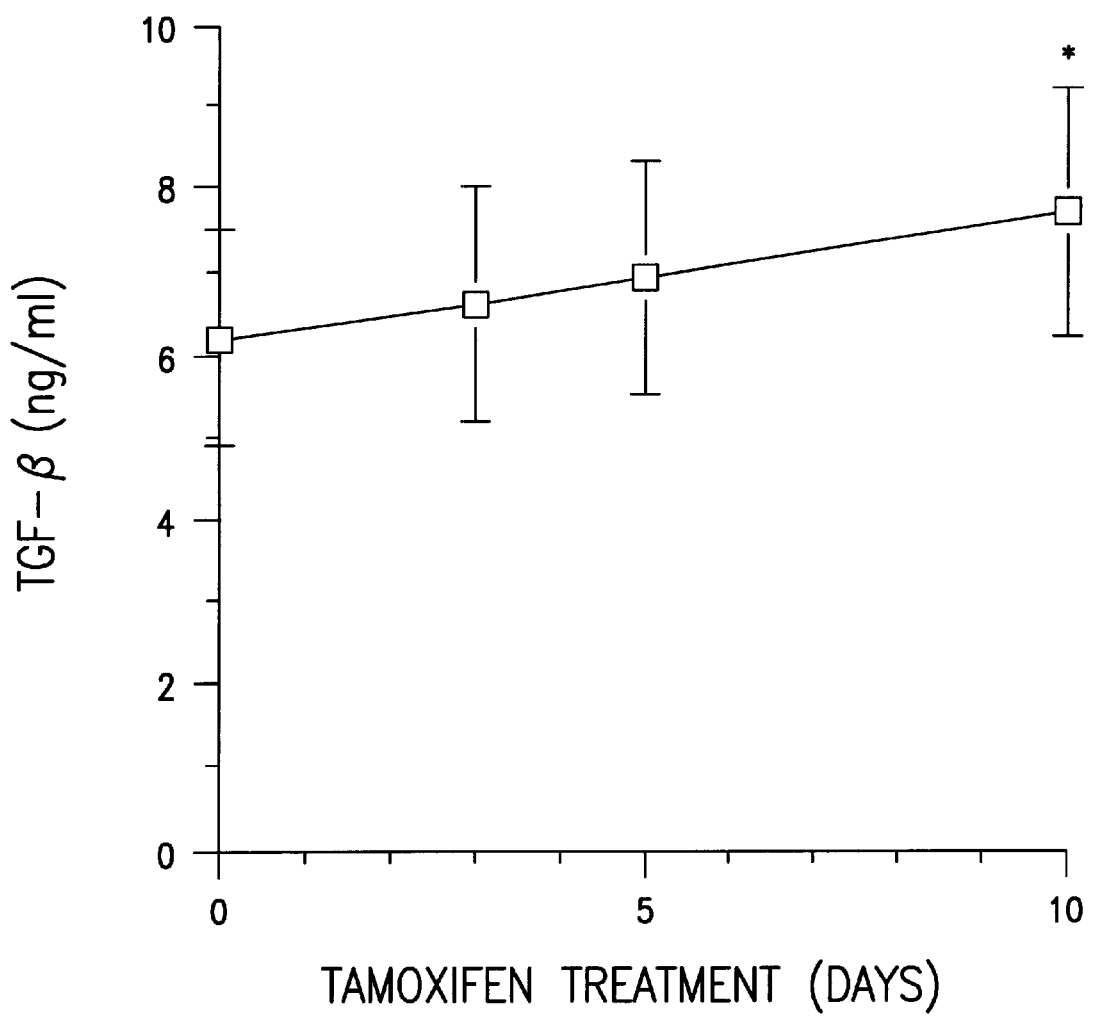
FIG. 7 depicts the effect of tamoxifen (TMX) treatment on plasma TGF-beta over time. Active TGF-beta (□) and (a+1) TGF-beta (●) were assayed by ELISA in platelet poor plasma drawn at various times after beginning treatment with 40 mg/day TMX.

The individuals in the NCA group had (a+1) TGF-beta and active TGF-beta levels typical of healthy individuals reported previously. These patients had either taken no aspirin (n=19), or 75 mg (n=14), 150 mg (n=8) or 300 mg (n=1) of aspirin per day for an average of 17 months. There was a significant correlation between aspirin dose and (a+1) TGF-beta levels (p<0.05; one way analysis of variation) suggesting that aspirin stimulates TGF-beta production in a dose-dependent manner (FIGS. 6A and 6B). The mean (a+1) TGF-beta level was significantly higher in patients taking 75 mg/day of aspirin (+41%; p<0.05), and in patients taking 150 mg/day of aspirin (55%; p<0.05). This is consistent with a previous study, where (a+1) TGF-beta levels were elevated by 66% in patients taking 150 mg aspirin per day. TGF-beta activity was also elevated in NCA individuals taking 150 mg aspirin per day (FIG. 6A), and hence the proportion of TGF-beta in the active form was not significantly changed. TGF-beta production was similarly higher in both men and women taking aspirin (+47% in men compared to 44% in women at 150 mg per day; FIG. 6C).

EXAMPLE IV

Copper Aspirinate is a TGF-beta Stimulating Agent

One disadvantage of aspirin as a TGF-beta stimulator is that aspirin is not very potent in human cell culture or in vivo. Therefore, the identification of other TGF-beta production stimulators which are more potent than aspirin is needed.

Consumption of red wine has been proposed to mediate cardiovascular protection, although the data supporting this proposal are still debated. To determine whether red wine, as opposed to white wine, can stimulate TGF-beta production in vitro or in vivo, red wine (Chateaux 1993 from the Bordeaux region) or white wine (German Reisling) was lyophilized and reconstituted in one tenth volume of 5% ethanol in water to produce a 10 fold wine concentrate. Red and white grape juice (Sainsbury's) were treated similarly as controls as they are expected to lack the active components produced during fermentation of the grape skins. Rat vascular smooth muscle cells (rVSMCs) were subcultured into DMEM+10% fetal calf serum, grown for 24 hours then treated with various concentrations of the wines or grape juices. The medium was replaced after 48 hours and after 96 hours, the cells released with trypsin and counted by haemocytometer. Final concentrations of the wine and grape juice on the cells were expressed as a percentage of the concentration of the original wine or grape juice.

Red wine, but not white wine or either grape juice, inhibited VSMC proliferation with an $ED_{50}$ of 25–33% concentration. At the highest concentration tested (200%) the increase in cell number after 96 hours was inhibited by 46±6% (n=3).

To determine whether this inhibition of VSMC proliferation by the red wine concentrate was due to induction of TGF-beta, cells were incubated with 25% and 100% concentration of red wine in the presence and absence of 10 µg/ml of a neutralizing antiserum to TGF-beta, which has previously been shown to completely abolish the growth inhibitory effects of 10 ng/ml TGF-beta in VSMC culture. The presence of neutralizing antibody to TGF-beta completely reversed (>95%) the growth inhibitory effects of the red wine. Thus, red wine induces TGF-beta production by VSMCs in vitro and this effect is not due to the alcohol component.

To investigate whether red wine might also elevate TGF-beta levels in vivo, blood samples were drawn from 120 randomly selected individuals in Toulouse, France and serum prepared. Additionally, these subjects completed a questionnaire which included details of their wine consumption. Active plus latent (a+1) TGF-beta and active TGF-beta levels in these samples were assayed by ELISA as described hereinabove. The mean (a+1) TGF-beta and active TGF-beta levels were not significantly different from those reported from other random populations.

A weaker correlation was observed between red wine consumption and active TGF-beta levels. Thus, (a+1) TGF-beta was almost two fold higher in the group of individuals drinking more than 1 standard deviation above the mean red wine consumption than those more than 1 standard deviation below the mean. Although there was also a significant correlation between total alcohol consumption and (a+1) TGF-beta levels, this may result from the large fraction of total alcohol consumed which is taken as red wine in this population. There was no correlation between white wine, beer or spirit consumption and either (a+1) TGF-beta or active TGF-beta levels. Thus, it is very likely that increased wine consumption is associated with elevated TGF-beta levels in the circulation.

When the red wine consumed was divided by the region of origin, four regions were significantly represented. However of these, only individuals drinking wine originally from Bordeaux showed a statistically significant correlation with (a+1) TGF-beta levels. This may be a consequence of the reduced numbers of individuals in each group, or alternatively suggests that only wines of Bordeaux origin stimulate TGF-beta production or increase TGF-beta levels more potently than wines of other origins.

Red wines, but not white wines, have been shown to contain various salicylate components which are produced during fermentation of the grape skins. To determine whether a salicylate component of red wine was correlated to TGF-beta activity, cultured (rat or human) VSMCs were exposed to red wine in the presence of various concentrations of a neutralizing antibody raised against sodium salicylate coupled to keyhole limpit hemocyanin as a carrier protein. The anti-salicylate antibody reversed the growth inhibitory activity of Bordeaux red wine with an $ED_{50}$ of 15 µg/ml. At concentrations of 33 µg/ml and above, maximal reversal of the growth inhibition was achieved, i.e., approximately 70% of the growth inhibitory activity was reversed. The majority of the TGF-beta stimulating activity in Bordeaux red wine is therefore due to the presence of salicylate-like compounds.

Given the likely concentration of salicylate in this red wine, based on previous studies, and the $ED_{50}$ for aspirin inducing TGF-beta in VSMC culture, the presence of salicylate alone cannot explain the observed effects. One possible resolution of this paradox would be the presence of salicylate-like compounds in red wine which stimulate TGF-beta more potently than acetyl salicylate. One such derivative, reported to have more potent effects than aspirin is the transition metal complex copper II (acetyl salicylate)$_2$. The ED$_{50}$ for TGF-beta production of the complex (Cu Aspirinate) was determined in cultured rat and human VSMCs. Cu aspirinate was almost two orders of magnitude more potent than aspirin at stimulating TGF-beta (ED$_{50}$ on human cells 200 nM for Cu aspirinate versus 10 μM for aspirin). It is likely that there is sufficient Cu aspirinate in red wine, and particularly in red wines of Bordeaux origin which are especially rich in copper, to account for most if not all of the TGF-beta stimulating activity associated with red wine.

Thus, copper aspirinate complex is believed to be the active TGF-beta stimulating agent in red wine and is a potent TGF-beta production stimulating agent in vitro and in vivo.

EXAMPLE V

TGF-beta Levels in Tamoxifen Treated Patients

To investigate whether TGF-beta levels are elevated after TMX administration, fifteen patients with stable angina and angiographically defined triple vessel disease took TMX daily for ten days at a dose similar to that generally used for breast cancer therapy. Patients with triple vessel disease (TVD) were defined as individuals having at least 50% stenosis of all three coronary arteries by angiography, which was confirmed by two independent observers. All had stable angina, with no myocardial infarction in the previous three months. Patients with unstable angina, poor left ventricular function, ventricular hypertrophy or diabetes were excluded.

Blood samples were taken and plasma prepared before and during the treatment period, and these samples were analyzed for TGF-beta, Lp(a), PAI-1 and lipoprotein profiles. Patients were asked to fast overnight prior to samples of blood being drawn between 9 am. and 10 a.m. the following morning. Blood samples were drawn by venepuncture of the antecubital vein with no tourniquet applied using a 21 gauge butterfly needle. Half the blood was allowed to clot for 2 hours at room temperature in polypropylene tubes. The clot was spun down (1,500×g; 15 minutes) and aliquots of the serum was stored at −100° C. The remaining blood was dispensed into Diatube H tubes (Diagnostica Stago) and cooled on ice for 15 minutes. Blood cells and platelets were spun down (6,000×g; 30 minutes) and the middle third of the supernatant was taken, carefully avoiding disturbing the pellet. This platelet-poor plasma was stored in aliquots at −100° C. until assayed. For all samples, assay for PF4 demonstrated that less than 0.02% of the platelets had degranulated during plasma preparation.

Active plus acid-activatable latent (a+1) TGF-beta levels were assayed in platelet-poor plasma using seven different assay methods. There has been debate in the literature regarding the most appropriate way to measure (a+1) TGF-beta, so to avoid difficulties specific to any particular measurement method all the available methods which have been described in the literature were used. The seven methods are:
(A) A sandwich ELISA using BDA19 and BDA5 (R&D Systems) antibodies with no activation step required.
(B) The Quantikine TGF-beta1 ELISA kit (R&D Systems) using acid/urea as the activation buffer in accordance with the manufacturer's instructions
(C) The Quantikine TGF-beta1 ELISA kit (R&D Systems) using acid alone as the activation buffer
(D) The BioTrak TGF-beta1 ELISA kit (Amersham International) using acid/urea as the activation buffer
(E) The BioTrak TGF-beta1 ELISA kit (Amersham International) using acid alone as the activation buffer in accordance with the manufacturers instructions
(F) The TGF-beta1 ELISA kit (Genzyme Diagnostics) using acid/urea as the activation buffer in accordance with the manufacturer's instructions
(G) The TGF-beta1 ELISA kit Promega Corporation) using acid alone as the activation buffer in accordance with the manufacturer's instructions Replicate aliquots of plasma taken from the same individuals at the same time were assayed by all seven methods.

The partitioning of TGF-beta between the lipoproteins and plasma proteins was analyzed by separating the lipoprotein fraction (d<1.215 g/cm$^2$) from the plasma proteins by density ultracentrifugation as described hereinabove. TGF-beta levels were assayed in both fractions using the Quantikine ELISA kit, following release and activation of TGF-beta with acetic acid and urea in accordance with the manufacturer's instructions. None of the three TGF-beta ELISAs used here detected TGF-beta in the lipoprotein fraction without prior extraction/activation with acetic acid/urea.

Total plasma triglyceride, total plasma cholesterol, HDL-cholesterol, LDL-cholesterol and VLDL-cholesterol were routinely assayed in all patients. Liver function tests (aspartate transaminase and lactate dehydrogenase) were also performed on samples prior to dosing with TMX and at the end of the study by a clinical biochemistry laboratory. Plasma PAI-1 was assayed using an ELISA (American Diagnostica) which recognizes active endothelial PAI-1 as well as inactive PA/PAI-1 complexes. Lipoprotein(a) was assayed by an ELISA for apolipoprotein(a) (Immuno) which showed no detectable cross reactivity with related proteins such as plasminogen. Platelet factor-4 (PF4) and β-thromboglobulin (βTG) were assayed using specific ELISAs (Diagnostica Stago).

Many of the parameters studied would not be expected to show a normal distribution in the population of TVD patients. Consequently, all comparisons are made with the baseline (day 0) values using the paired Wilcoxon signed-rank test. A p value of 0.05 or less was taken to indicate statistical significance.

TMX [Nolvadex™(tamoxifen citrate), Zeneca Ltd., Macclesfield, UK] at a dose of 40 mg was taken each morning, before breakfast, for 10 days. Before TMX treatment the mean (a+1) TGF-beta in plasma was 6.2±1.3 ng/ml.

During treatment with TMX, there was a trend of increasing concentration of (a+1) TGF-beta irrespective of the assay method used (Table 3). Each of the assay methods were standardized against different TGF-beta standard curves and gave significantly different median levels of (a+1) TGF-beta in the population at baseline. However, by day 10 there was a median increase of 59% in (a+1) TGF-beta. This increase was statistically significant for all the assay methodologies used, except for (G). This kit did not perform well, detecting much lower levels of (a+1) TGF-beta at both baseline and after treatment than all the other methods (A) to (F).

Therefore, during treatment of men with TMX there is a statistically significant increase in the amount of (a+1) TGF-beta in plasma, by 10 days after treatment is com menced. This increase is detected irrespective of the methodology used to measure (a+1) TGF-beta.

TABLE 3

|  | Day 0 | Day 10 | |
|---|---|---|---|
| Age (yrs) | 62.2 ± 1.5 | | |
| Total plasma cholesterol (mM) | 6.31 ± 0.28 | 5.95 ± 0.29* | |
| VLDL-cholesterol (mM) | 1.03 ± 0.14 | 0.84 ± 0.11* | |
| LDL-cholesterol (mM) | 4.48 ± 0.27 | 4.16 ± 0.25 | |
| HDL-cholesterol (mM) | 0.78 ± 0.03 | 0.77 ± 0.04 | |
| Total plasma triglycerides (mM) | 2.79 ± 0.44 | 2.28 ± 0.35 | |
| Plasma (a + 1) TGF-β (ng/ml) | | | |
| Method (A) | 6.2 ± 1.3 | 7.7 ± 1.5* | (+24%) |
| Method (B) | 0.7 ± 0.1 | 1.2 ± 0.2* | (+71%) |
| Method (C) | 0.25 ± 0.07 | 0.62 ± 0.07** | (+148%) |
| Method (D) | 2.0 ± 0.1* | 2.4 ± 0.1* | (+20%) |
| Method (E) | 1.7 ± 0.1 | 2.3 ± 0.1** | (+29%) |
| Method (F) | 3.9 ± 0.1 | 5.2 ± 0.3** | (+59%) |
| Method (G) | 0.1 ± 0.1 | 0.2 ± 0.1 | (+100%) |
| Lipoprotein(a) (mg/dl) | 61.3 ± 13.8 | 42.4 ± 9.5** | |
| Plasma PAI-I antigen (ng/ml) | 29.3 ± 6.4 | 35.9 ± 5.4* | |

All values are mean±standard error for 15 patients. Comparisons between baseline (day 0) and values after TMX treatment (day 10) were made using the paired Wilcoxon signed-ranks test. *, p<0.05; **, p<0.01.

Figure 8A:
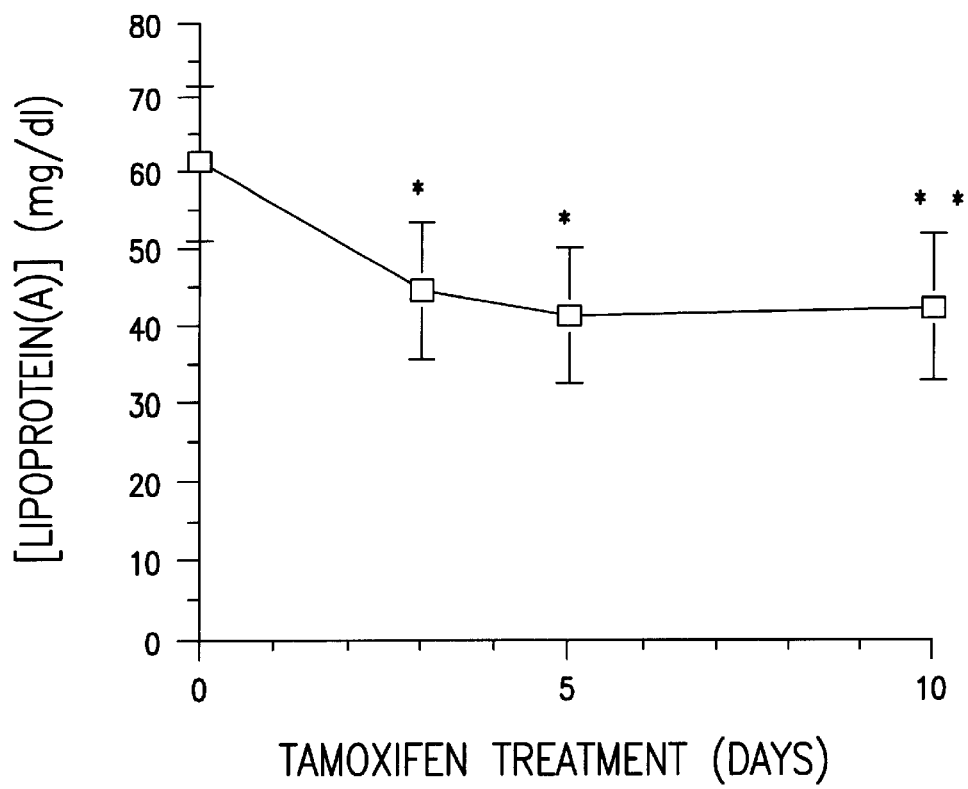
FIG. 8 depicts the effect of tamoxifen (TMX) on various cardiovascular risk factors. A) Lipoprotein(a) amounts. B) Proportion of TGF-beta associated with the lipoprotein fraction.
Figure 8B:
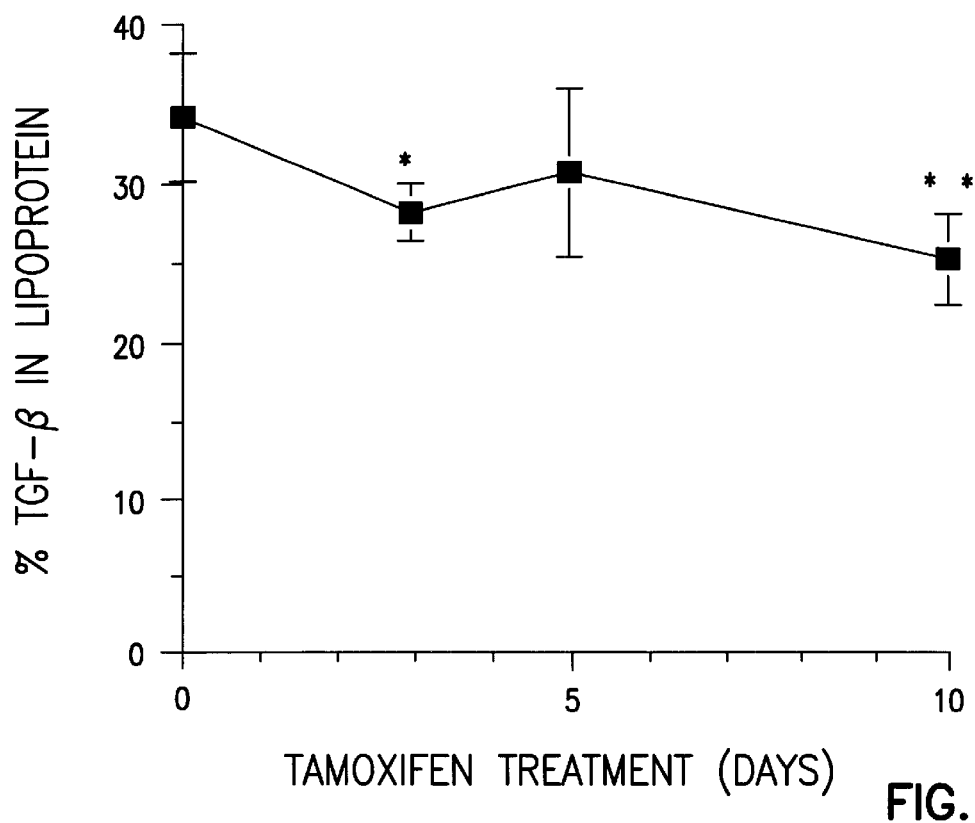

These patients had a high average level of Lp(a) (mean 61±10 mg/dl at baseline), consistent with their coronary artery status. The plasma concentration of Lp(a) was decreased by 27% (p<0.05 compared to baseline) by day 3 of TMX therapy. By day 10, the Lp(a) concentration was reduced by 31% compared to baseline (p=0.02; FIG. 8A).

Another cardiovascular risk factor which has been shown to influence TGF-beta activity is the lipoprotein profile, since TGF-beta can be sequestered into lipoprotein particles where it is biologically inactive. TMX has been reported to decrease plasma cholesterol and to increase the fraction of cholesterol in HDL particles. Consistent with these reports, total plasma cholesterol was decreased by 6% below baseline (p=0.04) after 10 days of TMX therapy. In addition, cholesterol in the VLDL fraction was reduced (18% below baseline; p=0.04) but the concentration of LDL-cholesterol and HDL-cholesterol were both unchanged (Table 3). Total plasma triglyceride concentration was 18% lower after 10 days of TMX treatment, but the change was not statistically significant (p=0.22).

Since TMX had significantly altered the lipoprotein profile of the patients, the proportion of the plasma TGF-beta associated with lipoprotein was measured. The lipoproteins were separated from the plasma proteins by density gradient ultracentrifugation. In order to detect the TGF-beta1 in the lipoprotein fraction, the Quantikine ELISA was used following release and activation of any TGF-beta in both the lipoprotein fraction and the plasma protein fraction. At baseline 34±4% of the TGF-beta was lipoprotein-associated and hence biologically inactive, but this was reduced to 25±3% (p<0.01) after 10 days of TMX therapy (FIG. 8C).

Figure 9:
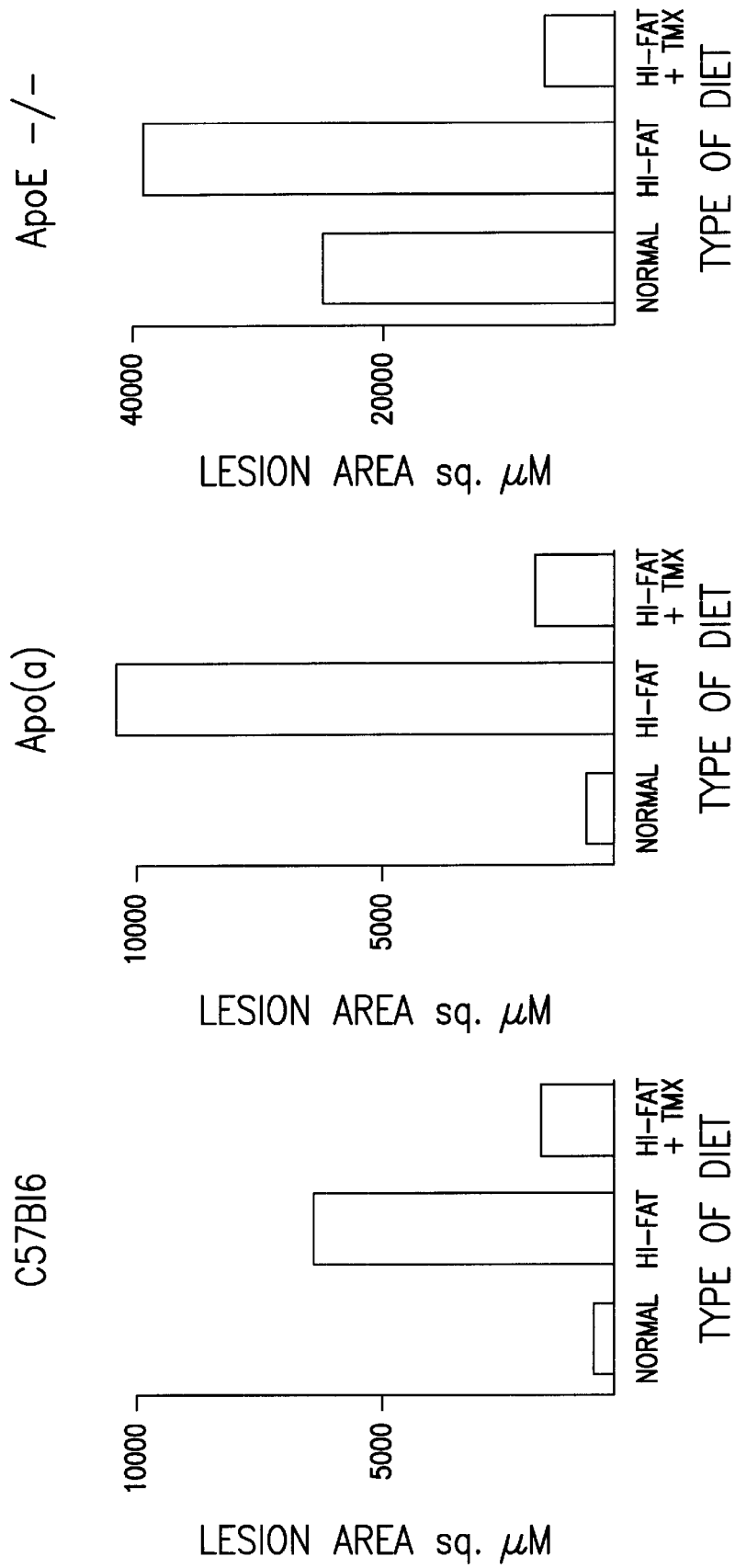
FIG. 9 depicts the lesion area in C57B16, apo(a) or apo(E)−/− mice fed a normal diet, high fat diet or high fat diet supplemented with TMX.

The data show that TMX (40 mg per day) elevates the plasma concentration of TGF-beta in men with severe coronary atherosclerosis. This increase was seen irrespective of which of the seven different methodologies were employed to measure (a+1) TGF-beta. Consistent with studies in cell culture and in mice, TMX elevates the amount of (a+1) TGF-beta, suggesting that the elevation may have resulted from increased synthesis of latent precursor complexes. In rat and human smooth muscle cell culture, TMX increases TGF-beta production by increasing the amount of TGF-beta1 mRNA. In other cell types TMX increases the translational efficiency of TGF-beta mRNA and hence increases production of the latent precursor protein. Irrespective of the mechanism, we observe increased levels of TGF-beta in men with atherosclerosis, corresponding to the increases seen in animal models of atherosclerosis when TMX significantly reduces lipid lesion formation, irrespective of the genetic predisposition to lesion formation (FIG. 9).

EXAMPLE VI

Combination Therapies to Elevate the Level of TGF-beta

Another disadvantage of aspirin as a cardiovascular agent, besides the fact that it is not a very potent TGF-beta elevating agent, is that it appears to be a pure stimulator of the latent form of TGF-beta. As a result, under conditions where TGF-beta activation or release is not occurring, or is occurring to a reduced extent, e.g., when PAI-1 inhibits activation or lipoproteins sequester TGF-beta, the supply of latent TGF-beta precursors may not be limiting for the generation of the active forms. This disadvantage can be overcome by combination therapy. Thus, the identification of agents that increase the level of mature and/or active TGF-beta, can be useful in combination therapies with aspirin or with other agents that are more potent stimulators of the latent form of TGF-beta, such as copper aspirinate.

To determine the efficacy of combination therapy, and to provide evidence for synergism between aspirin and fish oil, 8-week-old female apoE knockout mice were fed aspirin or fish oil, or both, to assess the cardioprotective effects of modulating different components of the TGF-beta pathway.

Group A mice (n=10) were sacrificed at day 0. Group B mice (n=10) were fed normal chow. Group C mice (n=10) were fed normal chow and about 3 mg/kg/day aspirin dissolved in water (15 μg/ml aspirin). Group D mice (n=10) were fed chow containing 33 mg/kg/day fish oil (200 μg Pulse cod liver oil/g food, Seven Seas Ltd., which contains 0.9 g eicosapentaenoic acid (EPA), and 0.3 g docosahexaenoic acid (DHA)) and 3 mg/kg/day aspirin dissolved in water. Group E mice (n=10) were fed chow containing 33 mg/kg/day fish oil. Group F mice (n=10) were fed chow containing Zocor (simvastatin; Zocor tablets, Merck, Sharpe & Dohme) at 400 μg/kg/day (2 μg/g food). Simvastatin is an inhibitor of the enzyme HMG-CoA reductase, the committed step in cholesterol biosynthesis. As a result, it has been shown to reduce the total plasma cholesterol concentration in man and in particular the concentration of cholesterol in the more triglyceride-rich particles (VLDL and LDL). If alterations in the lipid profile are responsible for the suppression of lesion formation previously observed with TMX, then simvastatin should reduce lesion formation.

Groups B–F were fed these regimens for 87 days. All mice were weighed daily for the first week and weekly thereafter. Food and water consumption over a 24 hour period were measured daily for the first 7 days and weekly thereafter. There was no significant difference in weight, food intake or water consumption in any of the groups throughout the study.

After 87 days, mice in groups B-F were fasted overnight and then sacrificed. Serum, heart, lungs and aorta samples were collected at the time of sacrifice. The heart, lungs and aorta were removed from each mouse and rinsed in PBS, dabbed dry on tissue and embedded in Cryo-M-bed embedding medium (Bright Instruments, Huntington, U.K.) before snap freezing in liquid nitrogen. Frozen sections (4 µm thickness) of the aortic sinus region were prepared from the heart/lung/aorta blocks according to the sectioning strategy of Paigen et al. (*Arteriosclerosis*, 10, 316 (1990)). Sections on 5% gelatin-coated slides were stained for neutral lipid by the Oil Red O technique and counter-stained with fast green (Grainger et al., *Nature Med.*, 1, 1067 (1995)).

The development of lipid-filled vascular lesions was determined by the quantitation of oil red O staining for neutral lipid deposited in the aortic sinus region. The area of lipid accumulation was measured using a calibrated microscope eye-piece, such that lipid droplets<50 $\mu m^2$ were ignored and contiguous regions of lipid staining>500 µm in area were classified as lesions. The area staining for neutral lipid increased from 10,765±978 to 27,175±1040 $\mu m^2$/mouse over the three months of the experiment for mice fed a normal mouse chow diet, as seen in previous studies of spontaneous lesion development in apoE knockout mice. Treatment with aspirin alone did not affect lesion development over the same 3 month period (Table 4). Treatment with fish oil alone reduced lesion development slightly, although the variation in the area of lesions between animals within a group was too large for the effect to be statistically significant (−8%; p=0.11; Mann-Whitney U test).

In contrast, treatment with aspirin plus fish oil resulted in a significant reduction in lesion formation (−22%; p=0.01; Mann-Whitney U test), suggesting that aspirin and fish oil act synergistically to reduce lipid lesion formation. Treatment with simvastatin, however, did not significantly reduce lipid lesion formation in apoE knockout mice. The area staining for neutral lipid deposition was lower than in untreated mice (−7%; p=0.33; Mann-Whitney U test), but as with mice treated with fish oil alone, this decrease was not statistically significant.

Treatment with aspirin and fish oil, alone or in combination, also resulted in a marked change in lesion morphology. The area of cellular intima that formed was reduced, most markedly in the group which received the combination of aspirin and fish oil, and the lipid staining was confined to a region close to the internal elastic lamina. As a result, the lesions coalesced and the number of separate lesions decreased even where the total area staining for lipid accumulation was unchanged.

TABLE 4

| Group | Treatment | Lesion Area ($\mu m^2$ staining) | Number of Lesions |
|---|---|---|---|
| A | control, day 0 | 10,765 ± 978 | 3.4 ± 0.2 |
| B | control, day 88 | 27,175 ± 1040 | 10.5 ± 0.7 |
| C | aspirin | 27,512 ± 974 | 6.6 ± 0.2** |
| D | aspirin + fish oil | 23,587 ± 898** | 5.5 ± 0.4** |
| E | fish oil | 25,871 ± 1356 | 6.9 ± 0.3** |
| F | Zocor | 25,777 ± 1368 | 8.1 ± 0.4* |

*p < 0.01, **p < 0.05 Mann-Whitney U test

The amount of active plus latent and active TGF-beta in the vessel wall, and the amount of active TGF-beta (ng/ml) in the plasma of these mice was also determined (Table 5), by methodologies described in Examples 4 and 7 of copending U.S. application Ser. No. 08/478,936, filed Jun. 7, 1995, which is incorporated by reference herein.

The neighboring sections to those stained for neutral lipid with Oil Red O described above were taken onto slides coated with poly-L-lysine (0.1%; Sigma) and fixed in ice-cold acetone for 90 seconds, air-dried and stored at −20° C. until assayed. Active plus acid-activatable latent (a+1) TGF-beta was measured by quantitative immunofluorescence microscopy using specific primary antibodies (BDA 19, AB-100-NA; R&D Systems), see Mosedale et al., *Histochem. Cytochem.*, 44, 1043 (1996), the disclosure of which is incorporated by reference herein. Active TGF-beta was measured by quantitative immunofluorescence microscopy using the recombinant extracellular domain of the type II TGF-beta receptor (R2X) labeled with fluorescein.

The data in Table 5 show that active plus latent TGF-beta levels were significantly elevated in the vessel wall of mice having diets supplemented with aspirin (+36%; p<0.01; n=10, Mann-Whitney U test) relative to control mice. The amount of active TGF-beta was not significantly affected by aspirin therapy (−6%; p=NS), suggesting that the additional latent complexes were not efficiently activated in the vessel wall of apoE knockout mice. In contrast, fish oil treatment for three months did not affect (a+1) TGF-beta (+5%; p=NS) but elevated active TGF-beta to a small extent (+17%; p=0.05; n=10; Mann-Whitney U test). These results suggest that aspirin stimulates production of latent TGF-beta complexes, while fish oil increases the proportion of TGF-beta available in the active form, i.e., for receptor binding.

TABLE 5

| Group | Active + Latent TGF-beta in Vessel Wall | Active TGF-beta in Vessel Wall |
|---|---|---|
| A | 54 ± 4 | 36 ± 2 |
| B | 42 ± 4 | 18 ± 2 |
| C | 57 ± 3** | 17 ± 2 |
| D | 63 ± 6** | 24 ± 3** |
| E | 44 ± 4 | 21 ± 3* |
| F | 44 ± 5 | 20 ± 3 |

*p < 0.01, **p < 0.05 Mann-Whitney U test

Group D mice, which were treated with both aspirin and fish oil had significantly elevated levels of both (a+1) TGF-beta (+50%) and active TGF-beta (+33%) in the vessel wall compared with the control mice. The synergism of the effects of these drugs on the amount of active TGF-beta in the vessel wall is consistent with the proposed different mechanisms of action for the two drugs. Taken with the results shown in Table 4, an increase in level of active TGF-beta in apo(E)−/− mice correlates with a decrease in lesion number and area.

Simvastatin treated mice (Group F) showed no difference in the amounts of (a+1) TGF-beta and active TGF-beta in the vessel wall. Thus, in the apoE knockout mouse, any beneficial effects of simvastatin are unlikely to be attributed to elevation of TGF-beta activity. Similarly, any beneficial effects of the aspirin plus fish oil therapy on the lipoprotein profile are unlikely to have contributed to the therapeutic reduction in lesion area by this therapy.

In summary, agents that elevate TGF-beta activity in the vessel wall reduce or inhibit lipid lesion development in mouse aorta, while agents which do not affect TGF-beta activity are ineffective (Table 6). Furthermore, the statistical correlation between the magnitude of TGF-beta activity elevation and lesion area inhibition is very marked, suggesting that the greater increase in vessel wall TGF-beta activity which is achieved, the greater the inhibition of lesion development. This correlation provides powerful evidence supporting the role of TGF-beta activity in mediating the cardioprotective activity of both tamoxifen, and aspirin and fish oil.

TABLE 6

| Treatment | % Lesion Suppression | Fold increase in Active TGF-beta |
|---|---|---|
| None | 0 | 1.00 |
| Aspirin | −2 | 0.95 |
| Fish Oil | 8 | 1.1 |
| Aspirin and Fish Oil | 17* | 1.3* |
| TMX | 99* | 1.9* |

*Statistically significant, p < 0.001, Pearson's R correlation, r = 0.73

The effects of these treatments on the cellular changes associated with lesion formation, marked by the accumulation of osteopontin and loss of smooth muscle α-actin (SM-α-actin) in the vessel wall, which has been shown to be characteristic of lesion formation in man and animal models of atherosclerosis, was also examined. SM-α-actin and osteopontin were measured by quantitative immunofluorescence microscopy using specific primary antibodies A-6125 (Sigma) and MBP111Bio (NIH Developmental Studies Hybridoma Bank), respectively.

As lipid lesions developed over 3 months on a normal mouse chow diet, staining for SM-α-actin decreased (−36%; p<0.01; n=10; Mann-Whitney U test), while staining for osteopontin increased (+150%; p<0.01; n=10; Mann-Whitney U test). Of the treatments used in this study, only the combination of fish oil and aspirin abolished the loss of SM-α-actin and the accumulation of osteopontin (Table 7), consistent with the observation that this was the only treatment regimen which significantly reduced lipid accumulation into the vessel wall. The increase in SMα actin in mice treated with fish oil or fish oil plus aspirin is consistent with the observed increase in SMα actin in apo(E)−/− mice treated with TMX.

TABLE 7

| Group | SMα Actin | Osteopontin |
|---|---|---|
| A | 157 ± 22 | 32 ± 7 |
| B | 101 ± 12 | 80 ± 9 |
| C | 87 ± 9* | 84 ± 7 |
| D | 194 ± 18** | 55 ± 8** |
| E | 122 ± 17 | 67 ± 10* |
| F | 114 ± 19 | 73 ± 8 |

*p < 0.01, **p < 0.05 Mann-Whitney U test

TABLE 8

| | Active & Latent TGF-beta | Active TGF-beta | SMα Actin | Oil Red O |
|---|---|---|---|---|
| Active & latent TGF-beta | | r = 0.58** | r = 0.67*** | r = −0.065 |
| Active TGF-beta | | | r = 0.76*** | r = −0.32* |
| SMα actin | | | | r = −0.13 |
| Oil Red O | | | | |

*p < 0.01
**p < 0.001
***p < 0.0001

As shown by the correlations of data from Groups A–F summarized in Table 8, an increase in the level of active TGF-beta correlates with an increase in SMα actin expression. This result is consistent with the hypothesis that active TGF-beta regulates smooth muscle cell differentiation in vivo. Moreover, active TGF-beta, but not active plus latent TGF-beta, negatively correlates with lesion area, suggesting that active TGF-beta protects against lesion development.

The effect of each treatment on the lipid profile of each group of mice was determined by measuring the cholesterol and triglyceride. Blood from a terminal bleed was collected in a polypropylene tube, allowed to clot at room temperature for 2 hours and then spun (1,000×g; 5 minutes). The serum supernatant was aliquoted and stored at −20° C. until assayed. Total cholesterol and total triglycerides were determined for each mouse using the cholesterol oxidase and glycerol kinase UV end-point enzymatic methods respectively (Sigma Diagnostics). For determination of the lipoprotein profile, 100 μl of serum from every mouse in each group was pooled (a total of 1 ml serum for each group) and the lipoprotein fraction was separated by density gradient ultracentrifugation. The lipoprotein fraction was then further separated by gel filtration FPLC chromatography on a Sepharose 6B column, and the elution positions of the lipoprotein particles were detected by measuring cholesterol (by the cholesterol oxidase enzymatic method) in each fraction. VLDL particles eluted in fractions 1–10, LDL in fractions 11–20 and HDL in fractions after 20.

Treatment of the mice with aspirin for three months had no effect on total plasma cholesterol or on the lipoprotein profile (Table 8). Mice treated with diets containing fish oil (with or without aspirin) had similar total plasma cholesterol and triglyceride concentrations to control mice, although there was a small reduction in the concentration of both VLDL-cholesterol (−16%/) and LDL-cholesterol (−12%/) and an increase in HDL-cholesterol (+10%/). Consistent with the effects of dietary supplementation with fish oil in man, a decrease in cholesterol, primarily in the VLDL fraction, in apoE knockout mice treated with fish oil was observed.

There was a significant reduction in total plasma cholesterol in apoE knockout mice treated with simvastatin (−27%; p<0.01; n=10; Students unpaired t-test). Much of this reduction occurred in the VLDL fraction (−14%) and LDL fraction (−41%), with an increase in HDL-cholesterol. In contrast, TMX lowered VLDL by seven fold and is a much more powerful lipid-lowering agent in the apo(E)−/− mouse than simvastatin. Simvastatin also caused a significant reduction in total plasma triglyceride concentration (−12%). Consequently, for all lipoprotein parameters measured, simvastatin had a significantly more beneficial effect than aspirin and fish oil either alone or in combination.

TABLE 9

|  | Group A | Group B | Group C | Group D | Group E | Group F |
| --- | --- | --- | --- | --- | --- | --- |
| Total cholesterol (mg/dl) | n.d. | 306 ± 31 | 282 ± 28 | 273 ± 19 | 266 ± 25 | 224 ± 29** |
| Total triglyceride (mg/dl) | n.d. | 302 ± 28 | 320 ± 19 | 308 ± 25 | 296 ± 33 | 266 ± 14** |
| VLDL-cholesterol (mg/dl) | n.d. | 184 | 179 | 157 | 151 | 158 |
| LDL-cholesterol (mg/dl) | n.d. | 92 | 89 | 91 | 88 | 54 |
| HDL-cholesterol (mg/dl) | n.d. | 30 | 26 | 32 | 33 | 35 |

**$p < 0.001$; Mann-Whitney U test
n.d. = not determined.
A single measurement of the lipoprotein profile was made on blood pooled from all the mice in the Group.

Moreover, the percentage of TGF-beta sequestered in VLDL in Groups B–F and C57B16 mice, which were fed a high fat diet, showed that lipid sequestration of active TGF-beta was not a major mechanism of the inhibition of TGF-beta activity in apo(E)–/– mice.

In summary, aspirin and fish oil act synergistically to reduce aortic lipid lesion development in a mouse model of severe atherosclerosis. While aspirin or fish oil alone reduced the development of vascular lipid lesions in apoE knockout mice over a three month treatment period, a combination of aspirin plus fish oil therapy resulted in a greater reduction (22%) in lesion formation. If low dose aspirin therapy and dietary supplementation with fish oil differ in their mechanism of action, then their cardioprotective effects would be expected to be additive. However, the results described hereinabove provide evidence that the combination of aspirin and fish oil exerts a markedly synergistic effect. Thus, a combination of low dose aspirin and fish oil therapy can be very useful in cardiovascular disease prevention. Moreover, because fish oil is not a very effective VLDL lowering agent, more powerful VLDL lowering agents, such as TMX, can be employed in combination therapies with aspirin, aspirinate salts to result in more beneficial cardiovascular effects.

Consistent with data in humans, aspirin increases the level of latent TGF-beta, but not the amount of active TGF-beta, in the vessel wall of apo(E)–/– mice. Also consistent with data in humans, fish oil lowers VLDL, which results in lower levels of PAI-1 and an increase in the levels of active TGF-beta which are available for TGF-beta receptor binding.

Previously, tamoxifen treatment has been demonstrated to elevate TGF-beta activity and suppress lipid lesion formation in several transgenic mouse models of atherosclerosis (Grainger et al.). However, tamoxifen has a variety of other effects, including reducing total plasma cholesterol and inducing some weight loss, which may have contributed to the observed reduction in lesion development. As a result, it could not be concluded that elevating TGF-beta activity reduced lesion formation. In contrast, the study described hereinabove employed agents which elevate TGF-beta activity and which do not affect body weight and have much smaller effects on lipoprotein metabolism. Furthermore, simvastatin, which has a larger beneficial effect on the lipoprotein profile than the other treatments, does not significantly reduce lipid lesion formation. Since there is a significant correlation between increase in TGF-beta activity and decrease in lipid lesion formation for all the therapies ($r=0.909$; $p<0.001$), it can be concluded that elevation in TGF-beta activity is likely to be involved in the mechanism by which these agents reduce lesion formation in mammals.

EXAMPLE VII

Use of Therapeutic Agents of the Invention to Prevent Autoimmune Disorders

The therapeutic agents of the invention are also useful to prevent or treat other indications associated with TGF-beta, e.g., pathologies which result from a pathological inflammation reaction caused by the recognition of self-antigens ("autoimmune disorders"). Indications associated with pathological inflammation reactions include, but are not limited to, rheumatoid arthritis, multiple sclerosis and late-onset diabetes. The recruitment and activation of both autoreactive T cells and other inflammatory cells to the developing lesion contributes to both the chronic tissue damage and the acute symptoms of autoimmune disorders. Agents which reduce or prevent immune cell recruitment and/or activation may ameliorate both the painful symptoms associated with the disorder and the progressive destruction of the target tissue.

Figure 12:
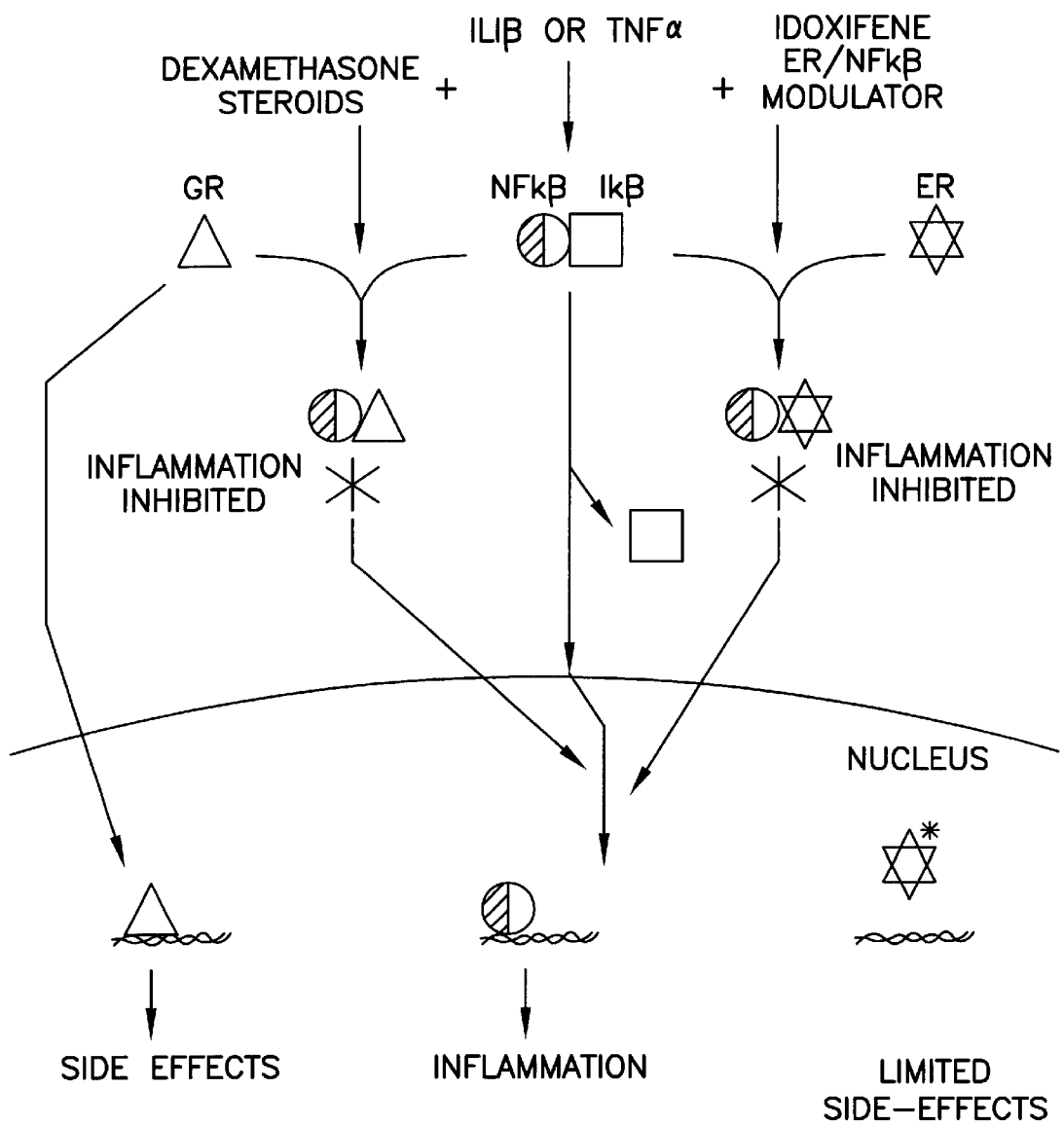
FIG. 12 depicts the pathways by which steroid and steroid-mimetic drugs act to produce anti-inflammatory effects and also undesirable side effects. The therapeutic action of ER/NFkB modulators is also depicted.
Figure 13:
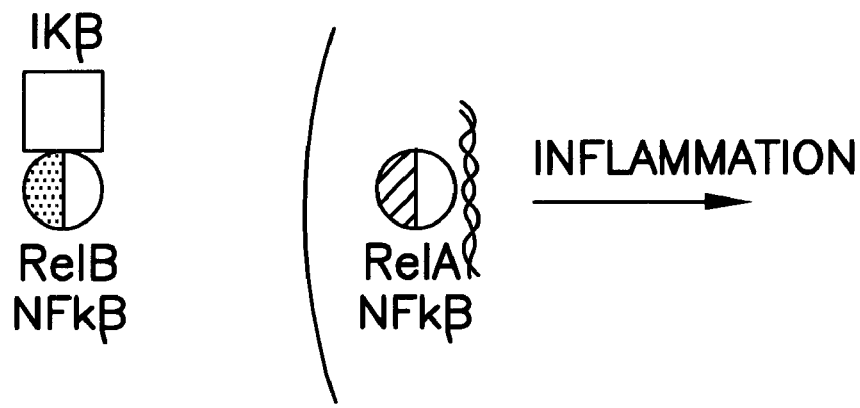
FIG. 13 depicts the pathway by which ER/NFkB modulators upregulate cellular mRNA encoding for TGF-beta.
Figure 13:
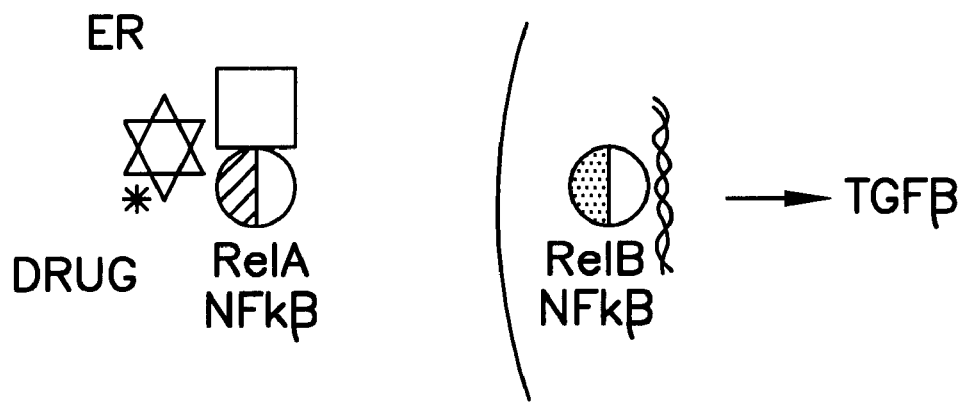

Current treatments for autoimmune disorders include the administration of anti-inflammatory steroids and steroid-mimetic drugs, such as dexamethasone, to reduce recruitment and activation of the immune cells in the developing lesions. These drugs act by binding to the glucocorticoid receptor (GR) which leads to the association of the GR with elements of the NFkB transcription factor complex. When the GR interacts with the NFkB complex, pro-inflammatory cytokines are inhibited. The binding of the steroids to the GR also results in the activation of GR. Activated GR is a nuclear transcription factor. Thus, a set of genes are activated in response to the binding of a steroid or steroid-mimetic drug to GR. This pathway is illustrated in FIG. 12. However, steroids and steroid-mimetic drugs cannot be used chronically to slow the progression of autoimmune diseases because they have an undesirable profile of side effects. Many or all of these side effects result from the direct activation of the GR as a transcription factor.

Thus, agents which modulate the interaction of the estrogen receptor (ER) with the NFkB transcriptional complex ("ER/NFkB modulators") without activating GR are useful to prevent or treat conditions characterized by the recruitment of autoreactive immune cells into tissue and the subsequent damage or destruction of that tissue by chronic inflammation. Preferred ER/NFkB modulators include idoxifene, raloxifene, droloxifene, toremifene, and tamoxifen, as well as functional equivalents, analogs or derivatives thereof. These agents also inhibit or reduce TNF-alpha mediated NFkB activation. Moreover, as ER/NFkB modulators are not characterized by the undesirable side effect profile of GR/NFkB modulators at the dose used to treat autoimmune disorders, they are therefore amenable to chronic use in the prevention or treatment of autoimmune disorders.

When cells which have NFkB activity, such as human smooth muscle cells (SMCs), were cultured in the presence of 20% fetal calf serum (FCS) in Dulbecco's modification of Eagles' Medium (DMEM), more than 95% of NFkB was present in the cytoplasm, as determined by immunostaining for p65. When the cells were incubated with a pro-inflammatory cytokine (recombinant human TNF-alpha at 20 ng/ml) for 6 hours at 37° C., >80% of the NFkB was translocated to the nucleus. In cells which had been transfected with a reporter construct which has three consensus kB DNA elements fused to the luciferase gene, the amount of light which was produced when the cell lysate was exposed to luciferin and ATP was proportional to NFkB activity. Treatment of human SMCs for 6 hours with 20 ng/ml TGF-alpha resulted in a 19-fold increase in NFkB activity, consistent with the translocation of the NFkB complex to the nucleus.

In contrast, when human SMCs were treated with tamoxifen, NFkB remained in the cytoplasm and there was no detectable change in NFkB activity. When the human SMCs were incubated simultaneously with TNF-alpha (20 ng/ml) and tamoxifen (5 $\mu$M), less than 10% of the NFkB was translocated to the nucleus and NFkB activity was stimulated by less than 3 fold. At this concentration, tamoxifen (TMX) inhibits TNF-alpha-induced NFkB activity by 86±12%.

Binding of tritium-labeled tamoxifen ($^3$H-TMX) was used to determine the affinity and number of binding sites for TMX in total cell lysates prepared from human VSMCs. Scatchard analysis of the binding of $^3$H-TMX revealed the presence of at least 3 distinct binding sites present at >1000 binding sites per cell. Site A had an affinity of 19 nM and was present at 4000 binding sites per cell. Site B had an affinity of 40 nM and was present at 9000 binding sites per cell and site C had an affinity of 3 $\mu$M and was present at 100,000 binding sites per cell. These results are consistent with Site B being the free human ER protein. It is likely that the higher affinity site A also contained the ER as it was efficiently immunoprecipitated by monoclonal antibodies directed against the human ER protein.

To identify other targets of TMX, an analog of 4-iodotamoxifen was covalently coupled to agarose and used to affinity purify antiestrogen binding proteins from total cell lysates prepared from human SMCs. Bound tamoxifen-binding proteins were eluted with the water-soluble quaternary tamoxifen salt N-methyl tamoxifen iodide. The eluting salt was removed by dialysis against Amberlite resin in phosphate buffer which irreversibly binds N-methyl tamoxifen. The affinity purified proteins were separated further by MonoQ ion exchange chromatography and fractions were assayed for $^3$H-TMX binding. Three peaks of protein associated with TMX-binding activity were identified. Peak I had an affinity of about 1 $\mu$M and may correspond to site C. Further purification of this protein by gel filtration chromatography and gel electrophoresis allowed a molecular identification of the protein by N-terminal sequence analysis as human serum albumin. The amount of protein in the other two pea of activity was less than the amount necessary to allow molecular characterization of these proteins.

Human SMC lysates were treated with a large excess of antibody directed against the human ER protein. After rotating overnight at 4° C., the antibody:antigen complex was precipitated by addition of 20 $\mu$l/ml protein A/G agarose and centrifuged for 5 minutes at 4° C. The supernatant was treated similarly, until no further ER protein could be detected in the precipitated faction. At concentrations of $^3$H-TMX below 50 nM (when the contribution by the low affinity site C should be negligible), all of the $^3$H-TMX binding sites were removed by treatment with the antibody directed against the human ER. Thus, both sites A and B (the high affinity sites) contain either the human ER or a protein which contains an epitope conserved with the human ER. It is very likely that both TMX binding complexes contain the ER.

To determine whether any ER protein in human VSMCs was complexed with other proteins, human SMCs cultured in DMEM+20% FCS were grown overnight in methionine-free DMEM+20% dialyzed FCS, then incubated with 50 $\mu$Ci/ml $^{35}$S-labeled methionine in methionine-free DMEM+ 20%/) dialyzed FCS for 6 hours. Total cell lysates were prepared from the labeled cells and immunoprecipitated with antibodies to ER The immunoprecipitated proteins were then analyzed by SDS gel electrophoresis and autoradiography. As expected, a band at 88 kDa corresponding to the ER protein was detected. Additionally, a band at 92 kDa was detected. Subsequent. Western blotting determined that the 92 kDa band was the heat shock protein hsp90, which has been shown to be associated with ER in the cytoplasm. A third protein was also efficiently immunoprecipitated with the ER. This third protein migrated at 37–40 kDa. Since it has been shown that the GR steroid receptor interacts with NFkB transcription factor complexes, the 37–40 kDa protein was analyzed by Western blotting with antibodies directed against IkB-alpha. Human IkB-alpha has been reported to migrate as a 37 kDa protein. These experiments confirmed that human IkB-alpha forms complexes with human ER either as a ternary complex with hsp90 or with human ER alone.

Whole cell lysates from human SMCs were treated with antibody to IkB-alpha until no further IkB-alpha was found in the precipitated fraction. The supernatant had about 50% of the binding sites for $^3$H-TMX present in the original lysate, while immunoprecipitation with non-immune antiserum did not reduce the number of TMX binding sites by more than 5%. Therefore, the three TMX binding sites in human SMC cell lysates are human serum albumin, a complex containing ER and IkB-alpha, and a complex containing ER but not IkB-alpha.

Because ER. interacts with NFkB transcription factor complexes in a similar manner to that for GR, agents which modulate ER/NFkB interaction should modulate the inflammatory response without activating GR. To test this hypothesis, SMCs in DMEM+10% FCS were transfected with a vector comprising the MMTV LTR promoter coupled to the chloramphenicol acetyl transferase (CAT) gene and the neomycin resistance gene (neo). A stably transfected line was selected using geneticin. When these cells were treated with dexamethasone, expression of the CAT gene was elevated 3.7±0.7 fold. Treatment of these cells with concentrations of TNF-alpha (up to 100 ng/ml), tamoxifen (up to 10 $\mu$M) or both agents together, did not stimulate expression of the CAT gene by more than 10%. Thus, ER/NFkB modulators would be expected to circumvent the undesirable side-effect profile associated with direct transcriptional activation by GR.

Tamoxifen may also upregulate expression of TGF-beta through its interaction with the NFkB transcription factor complex, as suggested by the following observations. (1) The p68 RelB knockout mouse has a phenotype similar to the TGF-beta knockout mouse, suggesting that RelB may be important in the upregulation of TGF-beta that normally turns off acute inflammation, and (2) the kB-like element in the rat TGF-beta-1 promoter is implicated in the tamoxifen-induced stimulation of TGF-beta expression. Thus, it is likely that a second consequence of ER/NFkB modulation by these agents is upregulation of TGF-beta expression. It is well known that TGF-beta has anti-inflammatory and immune-suppressive functions. Thus, the induction of TGF-beta by ER/NFkB modulating agents may act to synergistically reduce inflammation.

For ER/NFkB modulators, such as idoxifene, several exemplary dosing regimens are contemplated depending upon the particular autoimmune disease being treated and the stage to which the condition has progressed. For the treatment of incipient or early stage rheumatoid arthritis, when inflammation is evident but tissue damage is minimal, a low chronic oral dose of about 0.05 to about 10, preferably about 0.1 mg/kg/day, is employed. For local delivery, it is preferred that about 0.01 to about 1000 microgram per ml is administered, followed by chronic low dose oral delivery. When the disease progression is more severe, it is contemplated that a large loading dose, e.g., in the range of about 10 to about 100 mg/kg, is used to rapidly establish a therapeutic level of the ER/NFkB modulator in the circulation, followed by low chronic oral doses.

For the treatment of multiple sclerosis, an exemplary dose regimen is a single pre-loading dose, e.g., between about 10 to about 100 mg/kg, to establish a therapeutically effective amount of ER/NFkB modulator in the circulation, followed by a dose of about 0.1 to about 20, preferably about 0.5 to about 5, mg/kg/day.

ER/NFkB modulators that act to reduce or inhibit pathological inflammation associated with autoimmune disorders can be identified by the methods described hereinabove. Specifically, the agents may be identified by their ability to bind to NFkB/ER complexes, to inhibit NFkB activation induced by TNF-alpha and/or other pro-inflammatory cytokines, and to prevent activation of autoreactive T lymphocytes.

EXAMPLE VIII

Effects of the Therapeutic Agents on Cholesterol Levels

Twenty six patients with high cholesterol were administered simnvastatin for 16 weeks. Blood was collected at six times points during the 16 weeks and analyzed for TGF-beta levels. While serum cholesterol levels were reduced in these patients, there was no effect on TGF-beta levels in any of the patients. In contrast, some of the patients participating in a trial in which tamoxifen, a tamoxifen analog, or placebo, was administered, showed significant decreases in cholesterol levels. Therefore, a combination of one of the therapeutic agents of the invention and an agent which lowers serum cholesterol levels may exert a synergistic effect and thus, may be useful in the practice in the methods of the invention. Moreover, therapeutic agents of the invention alone may be useful to lower serum cholesterol levels.

EXAMPLE IX

Assay for Measuring Free Anti-sRII antibody in Human Serum

Recombinant sRII was coated onto the bottom of high protein binding ELISA plates for two hours in 50 mM carbonate buffer (pH 9), then washed, and non-specific binding blocked using 5% Tween-20 in 5% sucrose in water, containing 0.02% sodium azide (TSA block). Various serum and plasma samples were then incubated with the coated wells for 2 hours at room temperature with shaking. Unbound serum components were washed off using TBS plus 0.05% Tween-20 with four washing cycles ensuring complete aspiration of the well between each cycle. Any bound human immunoglobulin was then detected by adding anti-human-IgG antibodies coupled to horseradish peroxidase in wash buffer for one hour. Bound peroxidase was visualized using TMB substrate. All normal sera tested contained detectable levels of IgG antibodies binding to sRII. This signal was eliminated by omitting any one of: sRII antigen, serum or anti-human-IgG peroxidase. This confirms the presence of high affinity autoantibodies directed against the extracellular domain of the human type II TGF-β receptor.

It was also determined that human sera from normal healthy individuals does not contain autoantibodies against a wide variety of other human proteins, including, but not limited to, fibrinogen, factor II, compliment C4, apolipoprotein (a), collagen type I, III and IV or the extracellular domain of the human IL-10 receptor (a receptor expressed on endothelial cells). This data suggests that in normal humans there is a relatively specific autoimmune response to the TGFβ type II receptor extracellular domain.

Antibodies of the IgD class against sRII are also present in normal human serum. Although there may be antibodies of the IgM class, interference from rheumatoid factor (IgM directed against IgG) cannot be excluded at this time. Analysis of the anti-sRII IgG using IgG sub-class specific detection antisera has demonstrated that the majority of IgG reacting with sRII in normal human serum is of the IgG2 sub-class. Thus, to measure antibodies against sRII, ELISA plate wells are coated with recombinant or purified human sRII or an immunogenic portion thereof. Wells are blocked against non-specific binding using a blocking agent for the particular sample type, e.g. for serum analysis, a TCA block. Serum is added to the well, preferably undiluted and untreated. Plasma or other bodily fluids may also be used. The wells are washed to remove unbound components and the bound anti-sRII Ig is detected using an appropriate anti-human Ig antiserum, labeled for detection.

Because the assay does not determine absolute levels of antibody, the signal is referenced to a large pool of normal serum (PNS). A standard curve is constructed for each assay using sequential dilutions of PNS. PNS is arbitrarily designated to have 100 units of anti-sRII Ig, e.g., IgG.

| Results: | | |
|---|---|---|
| | Healthy normals | Median 100 units 95% of individuals in the range 50 to 200 units |
| | NCAs | Median 120 units 95% of individuals in the range 50 to 250 units |
| | TVDs | Median 15 units 95% of individuals in the range <10 to 50 units |

A result of <50 units on the detection of human pan IgG indicates the presence of atherosclerosis, with high sensitivity (>95%) and probably similar specificity. However, it is envisioned that the detection of other classes or subclasses, IgG2, may be useful to detect diseases characterized by endothelial cell activation, or a specific disease.

Body fluids that contain detectable levels of immunoglobulin may be used, e.g., plasma or serum. Samples can be fresh or frozen. The anti-sRII Ig are stable over time for a given individual (intraperson variation on a 3-month time scale is <10% of the interperson variation). Accurate diagnosis can therefore be achieved on single sample from a given individual. Moreover, the Ig are stable to multiple cycles of freeze thawing and to long storage times at −20° C. However, the assay is still subject to capture interference by subclass or classes of immunoglobulin not otherwise detected. For example, when using anti-human-IgG perioxidase as the detection antiserum, the assay may detect little or no IgG against sRII because of the presence of large amounts of IgD against sRII occupying all the available antigen sites.

The levels of anti-sRII-IgG in serum and plasma samples derived from individuals with severe coronary atherosclerosis, defined by coronary angiography and individuals with normal coronary angiograms, were measured. Patients with atherosclerosis (TVD patients) had approximately a five fold lower median concentration of anti-sRII-IgG compared with individuals with normal coronary arteries (NCA individuals). The absolute amount of sRII IgG could not readily be determined, but the relative amounts compared with pooled normal serum could be determined by running various dilutions of pooled normal serum as a standard curve with each assay. In all cases a standard pooled serum was used and this serum was arbitrarily designated to have 100 units of anti-sRII IgG.

Based on this standardization, the median concentration of anti sRII IgG among 100 individuals with coronary atherosclerosis was 14.6 units, compared with 84.9 units among the individuals with normal coronary arteries. This difference was highly statistically significant ($p<0.001$; Mann-Whitney U-test). The detection limit for the ELISA as performed under these conditions was approximately 10 units of anti-sRII-IgG. As a consequence, fully 40% of the patients with atherosclerosis had levels at or below the detection limit of the assay, whereas all of the individuals with normal coronary arteries had detectable levels. The sensitivity and specificity of this test are estimated to be greater than 90%. As a result measurement of anti-sRII IgG using this assay has far greater diagnostic potential than any existing plasma or serum biochemical marker for coronary heart disease.

This method can conveniently be used to diagnosis the presence of the disease (e.g. atherosclerosis), determine the extent of disease, evaluate prognosis (i.e, determine future risk prior to onset of symptoms), or to monitor the effectiveness of a treatment.

The suppressed levels of anti-sRII IgG in plasma and serum from individuals with atherosclerosis may be due to (a) lower levels of anti-sRII IgG, which assumes that lower detection of anti-sRII IgG results from the presence of lower levels of the IgG; (b) increased levels of anti-sRII IgD, or other non IgG classes, as the assays are subject to inhibition by non-IgG class anti-sRII antibodies; or (c) increased levels of sRII antigen. The sRII antigen which is normally expressed on endothelial cells may be shed during phenotypic changes in endothelial cell gene expression pattern, e.g., during activation, a process thought to occur in atherogenesis. sRII in plasma would then form complexes with the anti-sRII antibodies and make them more difficult to detect. As a result, lower levels of anti-sRII IgG would be detectable in individuals with increased endothelial cell activation.

MacCaffrey and colleagues have reported a switch from expression of TGF-β type II receptor to TGF-β type I receptor during the development of atherosclerosis in man, and one mechanism which might contribute to this switch would be shedding of sRII from endothelial cells as they become activated (MacCaffrey et al. *J. Clin. Invest.* 1996, 2667–2675). Thus, plasma concentrations of sRII may be a direct measure of the state of endothelial cell activation (related, for example, to functional tests of endothelial cells function, e.g., brachial reactivity). Since the presence of sRII is expected to reduce detection of any anti-sRII-IgG present in the plasma (by forming complexes with it), the level of anti-sRII-IgG would be a proxy measure for levels sRII antigen (i.e., low levels of anti-sRII-IgG result from high levels of sRII antigen, resulting, in turn, from endothelial cell activation). Thus, this assay represents the first useful plasma measure of endothelial cell function, and thus, is a measure of an individual at risk of or having a disease characterized by endothelial cell activation. Moreover, the assay offers many advantages over the low throughput endothelial cell function assays such as brachial reactivity currently being used.

In addition to the assay described above, the methodology described herein can also be utilized to carry out the following assays:

| | | |
|---|---|---|
| (a) | Detection of free sRII antigen | High levels diagnostic for very severe atherosclerosis |
| (b) | Detection of sRII:anti-sRII complexes | High level diagnostic of moderate to very severe atherosclerosis |
| (c) | Detection of total sRII antigen | Diagnostic of extent of endothelial cell activation and hence of atherosclerotic disease progression. |

The methodology described herein can also be used to determine the level (e.g. the relative presence or absence) of TGF-β type II receptors (e.g. the extracellular domain of the TGF-β type II receptor) in mammalian cells or tissue. Endothelial cells are believed to shed the extracellular domain of the TGF-β type II receptor during activation, and there is believed to be a correlation between endothelial cell activation and atherogenesis, as well as other diseases. Accordingly, the invention also provides a method comprising detecting TGF-β type II receptors in mammalian cells or tissue, by combining the cells or tissue with a capture moiety that binds TGF-β type II receptors or a portion thereof, forming a capture complex, and detecting or determining the amount of the capture complex.

All publications and patents are incorporated by reference herein, as though individually incorporated by reference, as long as they are not inconsistent with the present disclosure. The invention is not limited to the exact details shown and described, for it should be understood that many variations and modifications may be made while remaining within the spirit and scope of the invention defined by the claims.

What is claimed is:

1. A therapeutic method for preventing or treating a condition or symptom associated with Marfan's syndrome, fibrosis, or senile dementia, comprising administering to a mammal in need of such therapy, an effective amount of a compound of formula VI:

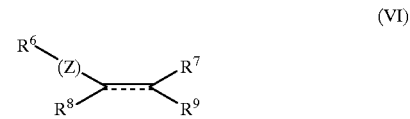

(VI)

wherein $R^6$ is ($C_1$–$C_6$)alkyl, or aryl, optionally substituted by 1, 2, or 3 V;

$R^7$ is phenyl, optionally substituted by 1, 2, or 3 V; or $R^7$ is ($C_1$–$C_{12}$)alkyl, halo($C_1$–$C_{12}$)alkyl, ($C_3$–$C_6$) cycloalkyl, ($C_1$–$C_6$)alkylcyclo($C_1$–$C_6$)alkyl, ($C_3$–$C_6$) cycloalkenyl, or ($C_1$–$C_6$)alkyl($C_3$–$C_6$)cycloalkenyl;

$R^8$ is hydrogen or phenyl, optionally substituted by 1, 2, or 3 V;

$R^9$ is heteroaryl, heteroaryl($C_1$–$C_3$)alkyl, ($C_1$–$C_4$) alkoxycarbonyl($C_1$–$C_6$)alkyl, ($C_1$–$C_{12}$)alkyl, ($C_3$–$C_6$) cycloalkyl, ($C_1$–$C_6$)alkylcyclo, ($C_1$–$C_6$)alkyl, ($C_3$–$C_6$) cycloalkenyl, or ($C_1$–$C_6$)alkyl($C_3$–$C_6$)cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof.

2. A therapeutic method for preventing or treating a condition or symptom associated with Parkinson's disease comprising administering to a mammal in need of such therapy, an effective amount of a compound of formula VI:

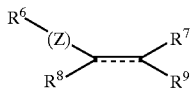

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1, 2, or 3 V;

$R^9$ is heteroaryl, heteroaryl$(C_1-C_3)$alkyl, $(C_1-C_4)$alkoxycarbonyl$(C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof.

3. A therapeutic method for preventing or treating a condition or symptom associated with Alzheimer's disease comprising administering to a mammal in need of such therapy, an effective amount of a compound of formula VI:

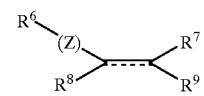

(VI)

wherein $R^6$ is $(C_1-C_6)$alkyl or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1, 2, or 3 V;

$R^9$ is heteroaryl, heteroaryl$(C_1-C_3)$alkyl, $(C_1-C_4)$alkoxycarbonyl $C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof.

4. A therapeutic method for preventing or treating a condition or symptom associated with an autoimmune disease comprising administering to a mammal in need of such therapy, an effective amount of a compound of formula VI:

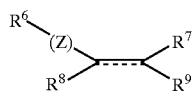

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1 2, or 3 V;

$R^9$ is heteroaryl, heteroaryl$(C_1-C_3)$alkyl, $(C_1-C_4)$alkoxycarbonyl$(C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2 or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —$C(=O)O$—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof.

5. The method of claim 4 wherein the autoimmune disease is lupus erythematosus.

6. The method of claim 4 wherein the autoimmune disease is rheumatoid arthritis.

7. The method of claim 4 wherein the autoimmune disease is multiple sclerosis.

8. A therapeutic method for lowering serum cholesterol comprising administering to a mammal in need of such therapy, an effective amount of a compound of formula VI:

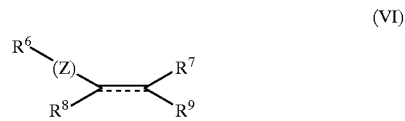

(VI)

wherein $R^6$ is $(C_1-C_6)$alkyl, or aryl, optionally substituted by 1, 2, or 3 V, $R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1, 2, or 3 V;

$R^9$ is heteroaryl, heteroaryl$(C_1-C_4)$alkyl, $(C_1-C_4)$alkoxycarbonyl$(C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —$C(=O)O$—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl or $(C_1-C_6)$alkanoyl;

the compound is MER25;

or a pharmaceutically acceptable salt thereof.

9. A therapeutic method for enhancing or promoting wound healing, comprising administering to a mammal in need of such therapy, an effective amount of a compound of formula VI:

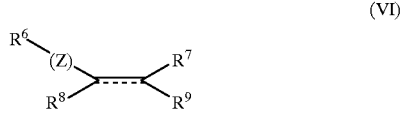

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1, 2, or 3 V;

$R^9$ is heteroaryl, heteroaryl$(C_1-C_3)$alkyl, $(C_1-C_4)$alkoxycarbonyl$(C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(C_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof.

10. The method of any one of claims 1, 2, 3, 4, 8 and 9 wherein Z is —$(CH_2)_{1-3}$—, —O—, -$OCH_2$—, —$CH_2O$—, —C(=O)O—, —$N(R_q)$—, or a covalent bond.

11. The method of any one of claims 1, 2, 3, 4, 8 and 9 wherein Z is —O—, —$OCH_2$—, —$CH_2O$—, —C(=O)O—, or —$N(R_q)$—.

12. The method of any one of claims 1, 2, 3, 4, 8 and 9 wherein $R^6$ is not phenyl or phenyl substituted by 1 or 2 V.

13. The method of any one of claims 1, 2, 3, 4, 8 and 9 wherein $R^7$ is not phenyl or phenyl substituted by 1 or 2 V.

14. The method of any one of claims 1, 2, 3, 4, 8 and 9 wherein $R^8$ is not phenyl, or phenyl substituted by 1 or 2 V.

15. A therapeutic method for preventing or treating a condition or symptom associated with osteoporosis comprising administer to a mammal in need of such therapy, an effective amount of a compound of formula VI:

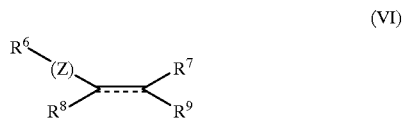

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl option substituted by 1, 2, or 3 V;

$R^9$ is heteroaryl, heteroaryl$(C_1-C_3)$alkyl, $(C_1-C_4)$alkoxycarbonyl$(C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoroethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ to together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof;

and provided that Z is not —$CH_2$— when $R^6$ is phenyl, substituted only at the 4-position with —$O(CH_2)_{1-3}R_k$; wherein $R_k$ is pyrrolidino, piperidino, 4-morpholino, dimethylamino, diethylamino, or hexamethyleneimino.

16. A therapeutic method for preventing or treating a condition or symptom associated with osteoporosis comprising administering to a mammal in need of such therapy, an effective amount of a compound of formula VI:

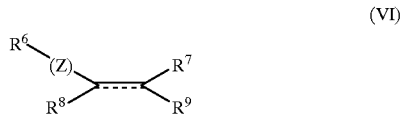

(VI)

wherein $R^6$ is $(C_1-C_6)$alkyl, or aryl, optionally substituted by 1, 2, or 3 V;

$R^7$ is phenyl optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1, 2, or 3 V;

$R^9$ is heteroaryl, heteroaryl$(C_1-C_3)$alkyl, $(C_1-C_4)$alkoxycarbonyl$(C_1-C_6)$alkyl, $(C_314\ C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_6)$alkylthio, halo, trifluoromethyl, pentafluoroethyl nitro, $N(R_n)(R_o)$, cyano, trifluoromethoxy, pentafluoroethoxy, benzoyl, hydroxy, $-(CH_2)_{0-4}C(=O)(C_1-C_6)$alkyl, $-UC(=O)(C_1-C_6)$alkyl, benzyl, $-OSO_2(CH_2)_{0-4}CH_3$, $-U(CH_2)_{1-4}COOR_p$, $-(CH_2)_{0-4}COOR_p$, $-U(CH_2)_{2-4}OR_p$, $-(CH_2)_{0-4}OR_p$, $-U(CH_2)_{1-4}C(=O)R_k$, $-(CH_2)_{0-4}C(=O)R_k$, $-U(CH_2)_{1-4}R_k$, $-(CH_2)_{0-4}R_k$, or $-U(CH_2)_{2-4}OC(=O)R_p$; wherein U is O, N($R_m$), or S;

Z is $-(CH_2)_{1-3}-$, $-O-$, $-OCH_2-$, $-CH_2O-$, $-C(=O)O-$, $-N(R_q)-$, $C=O$, or a covalent bond;

$R_k$ is amino, optionally substituted with one or two $(C_1-C_6)$alkyl; or an N-heterocyclic ring optionally containing 1 or 2 additional N($R_1$), S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl or $(C_1-C_6)$alkanoyl;

the compound is MER25;

or a pharmaceutically acceptable salt thereof;

and provided that Z is not $-CH_2-$ when $R^6$ is phenyl, substituted only at the 4-position with $-O(CH_2)_{1-3}\ R_k$; wherein $R_k$ is pyrrolidino, piperidino, morpholino, dimethylamino, diethylamino, or hexamethyleneimino.

17. A therapeutic method for preventing or treating a condition or symptom associated with osteoporosis comprising administering to a mammal in need of such therapy, an effective amount of a compound of formula VI:

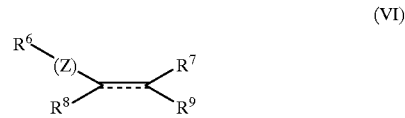

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_6)$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_1-C_6)$cycloalkenyl;

$R^8$ is hydrogen or phenyl optionally substituted by 1, 2, or 3 V;

$R^9$ is heteroaryl, heteroaryl$(C_1-C_3)$alkyl, $(C_1-C_4)$alkoxycarbonyl$(C_1-C_6)$alkyl$(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, $-(CH_2)_{0-4}C(=O)(C_1-C_6)$alkyl, $-UC(=O)(C_1-C_6)$alkyl, benzyl, $-OSO_2(CH_2)_{0-4}CH_3$, $-U(CH_2)_{1-4}COOR_p$, $-(CH_2)0-4COOR_p$, $-U(CH_2)_{2-4}OR_p$, $-(CH_2)_{0-4}OR_p$, $-U(CH_2)_{1-4}C(=O)R_k$, $-(CH_2)_{0-4}C(=O)R_k$, $-U(CH_2)_{1-4}R_k$, $-(CH_2)R_k$, or $-U(CH_2)_{2-4}OC(=O)R_p$; wherein U is O, N($R_m$) or S;

Z is $-O-$, $-OCH_2-$, $-CH_2O-$, $-C(=O)O-$, or $-N(R_q)-$;

$R_k$ is amino, optionally substituted with one or two $(C_1-C_6)$alkyl; or an N-heterocyclic ring optionally containing 1 or 2 additional N($R_1$), S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof.

18. A therapeutic method for preventing or treating a condition or symptom associated with osteoporosis comprising administering to a mammal in need of such therapy, an effective amount of a compound of formula VI:

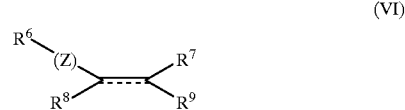

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkoxy,$(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is hydrogen or phenyl optionally substituted by 1, 2, or 3 V;

$R^9$ is heteroalkyl, heteroaryl$(C_1-C_3)$alkyl, $(C_1-C_4)$alkoxycarbonyl$(C_1-C_6)$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl, wherein any aryl or heteroaryl may optionally be substituted by 1, 2, or 3, V;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_n)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

the compound is MER25;

or a pharmaceutically acceptable salt thereof;

provided $R^6$ is not phenyl or phenyl substituted by 1 or 2 V.

19. A therapeutic method for preventing or treating a condition or symptom associated with Marfan's syndrome, fibrosis, or senile dementia, comprising administering to a mammal in need of such therapy, an effective amount of a compound of formula VI:

(VI)

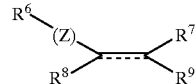

wherein $R^6$ is $(C_1-C_6)$alkyl, or aryl, optionally substituted by 1, 2, or 3 V;

$R^7$ is phenyl optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is phenyl substituted at the 2-position with Rj, and optionally substituted by 1, 2, or 3 V;

$R_9$ and $R_j$ together are —$CH_2CH_2$—, —S—, —O—, —N(H)—, —N{$(C_1-C_6)$alkyl}—, —$OCH_2$—, —OC{$(C_1-C_6)$alkyl}$_2$—, or —CH=CH—;

— — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(C_2)_{1-3}$—, —O—, —$OCH_2$—, —$CH_2O$—, —C(=O)O—, —$N(R_q)$—, C=O or a covalent bond;

$R_k$ is amino, optionally substituted with one or two $(C_1-C_6)$alkyl; or an N-heterocyclic ring optionally containing 1 or 2 additional $N(R_j)$, S, or nonperoxide O, wherein $R_l$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which the are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

or a pharmaceutically acceptable salt thereof.

20. A therapeutic method for preventing or treating a condition or symptom associated with Parkinson's disease comprising administering to a mammal in need of such therapy, an effective amount of a compound of formula VI:

(VI)

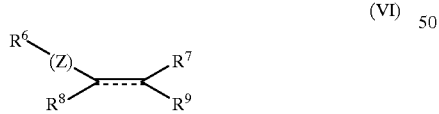

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R_8$ is phenyl substituted at the 2-position with Rj, and optionally substituted by 1, 2, or 3 V;

$R_9$ and $R_j$ together are —$CH_2CH_2$—, —S—, —O—, —N(H)—, —N{$(C_1-C_6)$alkyl}—, —$OCH_2$—, —OC{$(C_1-C_6)$alkyl}$_2$—, or —CH=CH—;

— — — — — is a single bond or is —C(B)(D)—, wherein B and D are each independently hydrogen, $(C_1-C_6)$alkyl, or halo;

V iS $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —$(CH_2)_{0-4}C(=O)(C_1-C_6)$alkyl, —$UC(=O)(C_1-C_6)$alkyl, benzyl, —$OSO_2(CH_2)_{0-4}CH_3$, —$U(CH_2)_{1-4}COOR_p$, —$(CH_2)_{0-4}COOR_p$, —$U(CH_2)_{2-4}OR_p$, —$(CH_2)_{0-4}OR_p$, —$U(CH_2)_{1-4}C(=O)R_k$, —$(CH_2)_{0-4}C(=O)R_k$, —$U(CH_2)_{1-4}R_k$, —$(CH_2)_{0-4}R_k$, or —$U(CH_2)_{2-4}OC(=O)R_p$; wherein U is O, $N(R_m)$, or S;

Z is —$(CH_2)_{1-3}$—, —O—, —$OCH_2$—, —$CH_2O$—, —C(=O)O—, —$N(R_q)$—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

or a pharmaceutically acceptable salt thereof;

provided that $R^9$ and $R_j$ together are not —S— when Z is C=O; $R^6$ is a phenyl radical substituted only at the 4-position with a group $O(CH_2)_2R_k$; $R_k$ is pyrrolidino, piperidino, or hexamethyleneimino; $R^7$ is phenyl substituted only at the 4-position with hydroxy, $(C_1-C_2)$alkoxy, —C(=O)$(C_1-C_6)$alkyl, or benzoyl; $R^8$ is phenyl substituted only at the 4-position with hydroxy, $(C_1-C_2)$alkoxy, —C(=O)$(C_1-C_6)$alkyl, or benzoyl and at the 2-position with $R_j$; and — — — — — is a single bond.

21. A therapeutic method for preventing or treating a condition or symptom associated with Alzheimer's disease comprising administering to a mammal in need of such therapy, an effective amount of a compound of formula VI:

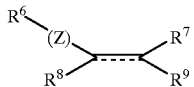

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is phenyl substituted at the 2-position with Rj, and optionally substituted by 1, 2, or 3 V;

$R^9$ and $R_j$ together are —CH$_2$CH$_2$—, —S—, —O— —N(H)—, —N{$(C_1-C_6)$alkyl}—, —OCH$_2$—, —OC{$(C_1-C_6)$alkyl}$_2$—, or —CH=CH—;

— — — — — is a single bond or is —C(B)(D)—, wherein B and D are each independently hydrogen, $(C_1-C_6)$alkyl, or halo;

V is OPO$_3$H$_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$ cyano, trifluoromethoxy, pentafluoroethoxy, benzoyl, hydroxy, —(CH$_2$)$_{0-4}$C(=O)$(C_1-C_6)$alkyl, —UC(=O)$(C_1-C_6)$alkyl, benzyl —OSO$_2$(CH$_2$)$_{0-4}$CH$_3$, —U(CH$_2$)$_{1-4}$COOR$_p$, —(CH$_2$)$_{0-4}$COOR$_p$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C(=O)R$_k$, —U(CH$_2$)$_{1-4}$R$_k$, —(CH$_2$)$_{0-4}$R$_k$, or —U(CH$_2$)$_{2-4}$OC(=O)R$_p$; wherein U is O, $N(R_m)$, or S;

Z is —(CH$_2$)$_{1-3}$—, —O—, —OCH$_2$—, —CH$_2$O—, —C(=O)O—, —N(R$_q$)—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

or a pharmaceutically acceptable salt thereof;

and provided that $R^9$ and $R_j$ together are not —CH$_2$CH$_2$—, —S—, —O— or —CH=CH— when Z is C=O; $R^6$ is a phenyl radical substituted only at the 4-position with a group —O(CH$_2$)$_{1-4}$R$_k$, $R_k$ is piperazino, heptamethyleneiminyl, imidazolinyl, pyrrolidino, piperidino, morpholinyl or hexamethyleneimino; $R^7$ is phenyl substituted only at the 4-position with hydroxy, halo, $(C_1-C_6)$alkoxy, or —OC(=O)$(C_1-C_6)$alkyl; $R_8$ is phenyl, substituted only at the 4-position with hydroxy, halo, $(C_1-C_6)$alkoxy, or —OC(=O)$(C_1-C_6)$alkyl and at the 2-position with $R_j$; and — — — — — is a single bond.

22. A therapeutic method for preventing or treating a condition or symptom associated with an autoimmune disease comprising administering to a mammal in need of such therapy, an effective amount of a compound of formula VI:

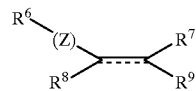

(VI)

wherein $R^6$ is $(C_1-C_6)$alkyl or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;

$R^8$ is phenyl substituted at the 2-position with $R_j$, and optionally substituted by 1, 2, or 3 V;

$R_9$ and $R_j$ together are —CH$_2$CH$_2$—, —S—, —O— —N(H)—, —N{$(C_1-C_6)$alkyl}—, —OCH$_2$—, —OC{$(C_1-C_6)$alkyl}$_2$—, or —CH=CH—;

— — — — — is a single bond or —C(B)(D)—, wherein B and D are each independently hydrogen, $(C_1-C_6)$alkyl, or halo;

V is OPO$_3$H$_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, —(CH$_2$)$_{0-4}$C(=O)$(C_1-C_6)$alkyl, —UC(=O)$(C_1-C_6)$alkyl, benzyl, —OSO$_2$(CH$_2$)$_{0-4}$CH$_3$, —U(CH$_2$)$_{1-4}$COOR$_p$, —(CH$_2$)$_{0-4}$COOR$_p$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C(=O)R$_k$, —U(CH$_2$)$_{1-4}$R$_k$, —(CH$_2$)$_{0-4}$R$_k$, or —U(CH$_2$)$_{2-4}$OC(=O)R$_p$; wherein U is O, $N(R_m)$, or S;

Z is —(CH$_2$)$_{1-3}$—, —O—, —OCH$_2$—, —CH$_2$O—, —C(=O)O—, —N(R$_q$)—, C=O, or a covalent bond;

$R_k$ is amino, optionally substituted with one or two $(C_1-C_6)$alkyl; or an N-heterocyclic ring optionally containing 1 or 2 additional $N(R_1)$, S, or nonperoxide O, wherein $R_1$ is H $(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5 or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

or a pharmaceutically acceptable salt thereof;

and provided that $R^9$ and $R_j$ together are not —S— when Z is C=O; $R^6$ is a phenyl radical substituted only at the 4-position with a group —O(CH$_2$)$_2$R$_k$; R$_k$ is pyrrolidino, piperidino, or hexamethyleneimino; $R^7$ is phenyl substituted only at the 4-position with hydroxy, $(C_1-C_2)$alkoxy, —C(=O)(C$_1$-C$_6$)alkyl, or benzoyl; $R^8$ is phenyl substituted only at the 4-position with hydroxy, $(C_1-C_2)$alkoxy, —C(=O)(C$_1$-C$_6$)alkyl, or benzoyl and at the 2-position with R$_j$; and — — — — — is a single bond.

23. The method of claim 22 wherein the autoimmune disease is lupus erythematosus.

24. The method of claim 22 wherein the autoimmune disease is rheumatoid arthritis.

25. The method of claim 22 wherein the autoimmune disease is multiple sclerosis.

26. A therapeutic method for lowering serum cholesterol comprising administering to a mammal in need of such therapy, an effective amount of a compound of formula VI:

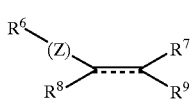

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$ cycloalkyl, $(C_1-C_6)$alkylcyclo$(C_1-C_6)$alkyl, $(C_3-C_6)$ cycloalkenyl, or $(C_1-C_6)$alkyl$(C_3-C_6)$cycloalkenyl;

$R^8$ is phenyl substituted at the 2-position with Rj, and optionally substituted by 1, 2, or 3 V;

$R^9$ and $R_j$ together are —CH$_2$CH$_2$—, —S—, —O— —N(H)—, —N{(C$_1$-C$_6$)alkyl}—, or —CH=CH—;

— — — — — is a single bond or is —C(B)(D)—, wherein B and D are each independently hydrogen, $(C_1-C_6)$alkyl, or halo;

V is OPO$_3$H$_2$, $(C_1-C_6)$alkyl, $(C_1-C_6)$alkoxy, mercapto, $(C_1-C_4)$alkylthio, halo, trifluoromethyl, pentafluoroethyl, nitro, N(R$_n$)(R$_o$), cyano, trifluoromethoxy, pentafluoroethoxy, benzoyl, hydroxy, —(CH$_2$)$_{0-4}$C(=O)(C$_1$-C$_6$)alkyl, —UC(=O)(C$_1$-C$_6$) alkyl, benzyl, —OSO$_2$(CH$_2$)$_{0-4}$CH$_3$, —U(CH$_2$)$_{1-4}$COOR$_p$, —(CH$_2$)$_{0-4}$COOR$_p$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C(=O)R$_k$, —U(CH$_2$)$_{1-4}$R$_k$, —(CH$_2$)$_{0-4}$R$_k$, or —U(CH$_2$)$_{2-4}$OC(=O)R$_p$; wherein U is O, N(R$_m$), or S;

Z is —(CH$_2$)$_{1-3}$—, —O—, —OCH$_2$—, —CH$_2$O—, —C(=O)O—, —N(R$_q$)—, C=O, or a covalent bond;

R$_k$ is amino, optionally substituted with one or two $(C_1-C_6)$alkyl; or an N-heterocyclic ring optionally containing 1 or 2 additional N(R$_l$), S, or nonperoxide O, wherein R$_l$ is H $(C_1-C_6)$alkyl, phenyl, or benzyl;

R$_n$ and R$_o$ are independently hydrogen, $(C_1-C_6)$alkyl, phenyl, benzyl, or $(C_1-C_6)$alkanoyl; or R$_n$ and R$_o$ together with the nitrogen to which they are attached are a 3, 4, 5, or 6 membered heterocyclic ring;

R$_p$ is H or $(C_1-C_6)$alkyl; and

R$_m$ and R$_q$ are independently hydrogen, $(C_1-C_6)$alkyl, phenyl, benzyl, or $(C_1-C_6)$alkanoyl;

or a pharmaceutically acceptable salt thereof;

provided the compound of formula VI is not raloxifene.

27. A therapeutic method for enhancing or promoting wound healing, comprising administering to a mammal in need of such therapy, an effective amount of a compound of formula VI:

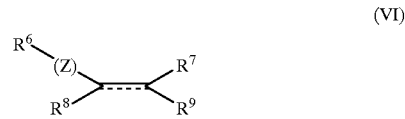

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$ cycloalkyl, $(C_1-C_6)$alkylcyclo$(C_1-C_6)$alkyl, $(C_3-C_6)$ cycloalkenyl, or $(C_1-C_6)$alkyl$(C_3-C_6)$cycloalkenyl;

$R^8$ is phenyl substituted at the 2-position with Rj, and optionally substituted by 1, 2, or 3 V;

$R^9$ and $R_j$ together are —CH$_2$CH$_2$—, —S—, —O— —N(H)—, —N{(C$_1$-C$_6$)alkyl}—, —OCH$_2$—, —OC{ (C$_1$-C$_6$)alkyl}$_2$—, or —CH=CH—;

— — — — — is a single bond or is —C(B)(D)—, wherein B and D are each independently hydrogen, $(C_1-C_6)$alkyl, or halo;

V is OPO$_3$H$_2$, $(C_1-C_6)$alkyl, $(C_1-C_6)$alkoxy, mercapto, $(C_1-C_4)$alkylthio, halo, trifluoromethyl, pentafluoroethyl, nitro, N(R$_n$)(R$_o$), cyano, trifluoromethoxy, pentafluoroethoxy, benzoyl, hydroxy, —(CH$_2$)$_{0-4}$C(=O)(C$_1$-C$_6$)alkyl, —UC(=O)(C$_1$-C$_6$) alkyl, benzyl, —OSO$_2$(CH$_2$)$_{0-4}$CH$_3$, —U(CH$_2$)$_{1-4}$COOR$_p$, —(CH$_2$)$_{0-4}$COOR$_p$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C(=O)R$_k$, —U(CH$_2$)$_{1-4}$R$_k$, —(CH$_2$)$_{0-4}$R$_k$, or —U(CH$_2$)$_{2-4}$OC(=O)R$_p$; wherein U is O, N(R$_m$), or S;

Z is —(CH$_2$)$_{1-3}$—, —O—, —OCH$_2$—, —CH$_2$O—, —C(=O)O—, —N(R$_q$)—, C=O, or a covalent bond;

R$_k$ is amino, optionally substituted with one or two $(C_1-C_6)$alkyl; or an N-heterocyclic ring optionally containing 1 or 2 additional N(R$_l$), S, or nonperoxide O, wherein R$_l$ is H$(C_1-C_6)$alkyl, phenyl, or benzyl;

R$_n$ and R$_o$ are independently hydrogen, $(C_1-C_6)$alkyl, phenyl, benzyl, or $(C_1-C_6)$alkanoyl; or R$_n$ and R$_o$ together with the nitrogen to which they are attached are a 3, 4, 5, or 6 membered heterocyclic ring;

R$_p$ is H or $(C_1-C_6)$alkyl; and

R$_m$ and R$_q$ are independently hydrogen, $(C_1-C_6)$alkyl, phenyl, benzyl, or $(C_1-C_6)$alkanoyl;

or a pharmaceutically acceptable salt thereof.

28. The method of any one of claims 19, 20, 21, 22, 23, and 24 wherein Z is —(CH$_2$)$_{1-3}$—, —O—, —OCH$_2$—, —CH$_2$O—, —C(=O)O—, —N(R$_q$)—, or a covalent bond.

29. The method of any one of claims 19, 20, 21, 22, 23, and 24 wherein Z is —O—, —OCH$_2$—, —CH$_2$O—, —C(=O)O—, or —N(R$_q$)—.

30. The method of claims 19, 20, 21, 22, 23, and 24 wherein $R^6$ is not phenyl or phenyl substituted by 1 or 2 V.

31. The method of any one of claims 19, 20, 21, 22, 23, and 24 wherein $R^7$ is not phenyl or phenyl substituted by 1 or 2 V.

32. A therapeutic method for preventing or treating a condition or symptom associated with osteoporosis comprising administering to a mammal in need of such therapy, an effective amount of a compound of formula VI:

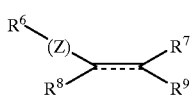

(VI)

wherein
  $R^6$ is $(C_1-C_6)$alkyl, or aryl, optionally substituted by 1, 2, or 3 V;
  $R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;
  $R^8$ is phenyl substituted at the 2-position with Rj, and optionally substituted by 1, 2, or 3 V;
  $R^9$ and $R_j$ together are —CH$_2$CH$_2$—, —S—, —O—, —N(H)—, —N{$(C_1-C_6)$alkyl}-, or —CH=C—;
  — — — — — is a single bond or is —C(B)(D)—, wherein B and D are each independently hydrogen, $(C_1-C_6)$alkyl, or halo;
  V is OPO$_3$H$_2$, $(C_1-C_6)$alkyl, $(C_1-C_6)$alkoxy, mercapto, $(C_1-C_6)$alkylthio, halo, trifluoromethyl, pentafluoroethyl, nitro, N(R$_n$)(R$_o$), cyano, trifluoromethoxy, pentafluoroethoxy, benzoyl, hydroxy, —(CH$_2$)$_{0-4}$C(=O)(C$_1$–C$_6$)alkyl, —UC(=O)(C$_1$–C$_6$)alkyl, benzyl, —OSO$_2$(CH$_2$)$_{0-4}$CH$_3$, —U(CH$_2$)$_{1-4}$COOR$_p$, —(CH$_2$)$_{0-4}$COOR$_p$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C(=O)R$_k$, —U(CH$_2$)$_{1-4}$R$_k$, —(CH$_2$)$_{0-4}$R$_k$, or —U(CH$_2$)$_{2-4}$OC(=O)R$_p$; wherein U is O, N(R$_m$), or S;
  Z is —(CH$_2$)$_{1-3}$—, —O—, —OCH$_2$—, —CH$_2$O—, —C(=O)O—, —N(R$_q$)—, or a covalent bond;
  R$_k$ is amino, optionally substituted with one or two $(C_1-C_6)$alkyl; or an N-heterocyclic ring optionally containing 1 or 2 additional N(R$_l$), S, or nonperoxide O, wherein R$_l$ is H $(C_1-C_6)$alkyl, phenyl, or benzyl;
  R$_n$ and R$_o$ are independently hydrogen, $(C_1-C_6)$alkyl, phenyl, benzyl, or $(C_1-C_6)$alkanoyl; or R$_n$ and R$_o$ together with the nitrogen to which they are attached are a 3, 4, 5, or 6 membered heterocyclic ring;
  R$_p$ is H or $(C_1-C_6)$alkyl; and
  R$_m$ and R$_q$ are independently hydrogen, $(C_1-C_6)$alkyl, phenyl, benzyl, or $(C_1-C_6)$alkanoyl;
  or a pharmaceutically acceptable salt thereof;
  and provided that Z is not —CH$_2$— when $R^6$ is phenyl, substituted only at the 4-position with —O(CH$_2$)$_{1-3}$R$_k$; wherein R$_k$ is pyrrolidino, piperidino, 4-morpholino, dimethylamino, diethylamino, or hexamethyleneimino.

33. A therapeutic method for preventing or treating a condition or symptom associated with osteoporosis comprising administering to a mammal in need of such therapy, an effective amount of a compound of formula VI:

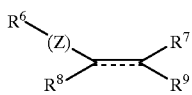

(VI)

wherein
  $R^6$ is $(C_1-C_6)$alkyl, or aryl, optionally substituted by 1, 2, or 3 V;
  $R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;
  $R^8$ is phenyl substituted at the 2-position with Rj, and optionally substituted by 1, 2, or 3 V;
  $R^9$ and $R_j$ together are $R^9$ and $R_j$ together are —CH$_2$CH$_2$—, —O—, —N(H)—, —N{$(C_1-C_6)$alkyl}-, or —CH=CH—,
  — — — — — 13 is a single bond or is —C(B)(D)—, wherein B and D are each independently hydrogen, $(C_1-C_6)$alkyl, or halo;
  V is OPO$_3$H$_2$, $(C_1-C_6)$alkyl, $(C_1-C_6)$alkoxy, mercapto, $(C_1-C_4)$alkylthio, halo, trifluoromethyl, pentafluoroethyl, nitro, N(R$_n$)(R$_o$), cyano, trifluoromethoxy, pentafluoroethoxy, benzoyl, hydroxy, —(CH$_2$)$_{0-4}$C(=O)(C$_1$–C$_6$)alkyl, —UC(=O)(C$_1$–C$_6$)alkyl, benzyl, —OSO$_2$(CH$_2$)$_{0-4}$CH$_3$, —U(CH$_2$)$_{1-4}$COOR$_p$, —(CH$_2$)$_{0-4}$COOR$_l$, —U(CH$_2$)$_{2-4}$OR$_p$, —(CH$_2$)$_{0-4}$OR$_p$, —U(CH$_2$)$_{1-4}$C(=O)R$_k$, —(CH$_2$)$_{0-4}$C(=O)R$_k$, —U(CH$_2$)$_{1-4}$R$_k$, —(CH$_2$)$_{0-4}$R$_k$, or —U(CH$_2$)$_{2-4}$OC(=O)R$_p$; wherein U is O, N(R$_m$), or S;
  Z is —(CH$_2$)$_{1-3}$—, —O—, —OCH$_2$—, —CH$_2$O—, —C(=O)O—, —N(R$_q$)—, C=O, or a covalent bond;
  R$_k$ is amino, optionally substituted with one or two $(C_1-C_6)$alkyl; or an N-heterocyclic ring optionally containing 1 or 2 additional N(R$_l$), S, or nonperoxide O, wherein R$_l$ is H$(C_1-C_6)$alkyl, phenyl, or benzyl;
  R$_n$ and R$_o$ are independently hydrogen, $(C_1-C_6)$alkyl, phenyl, benzyl or $(C_1-C_6)$alkanoyl; or R$_n$ and R$_o$ together with the nitrogen to which they are attached are a 3, 4, 5, or 6 membered heterocyclic ring;
  R$_p$ is H or $(C_1-C_6)$alkyl; and
  R$_m$ and R$_q$ are independently hydrogen, $(C_1-C_6)$alkyl, phenyl, benzyl, or $(C_1-C_6)$alkanoyl;
  or a pharmaceutically acceptable salt thereof;
  and provided that Z is not —CH$_2$— when $R^6$ is phenyl, substituted only at the 4-position with —O(CH$_2$)$_{1-3}$R$_k$; wherein R$_k$ is pyrrolidino, piperidino, 4-morpholino, dimethylamino, diethylamino, or hexamethyleneimino.

34. A therapeutic method for preventing or treating a condition or symptom associated with osteoporosis comprising administering to a mammal in need of such therapy, an effective amount of a compound of formula VI:

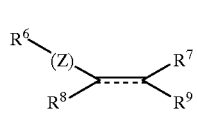

(VI)

wherein
  $R^6$ is $(C_1-C_6)$alkyl, or aryl, optionally substituted by 1, 2, or 3 V;
  $R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl, or $(C_1-C_6)$alkyl$(C_3-C_6)$cycloalkenyl;
  $R^8$ is phenyl substituted at the 2-position with Rj, and optionally substituted by 1, 2, or 3 V;
  $R^9$ and $R_j$ together are —CH$_2$CH$_2$—, —O—, —N(H)—, —N{$(C_1-C_6)$alkyl}-, —OCH$_2$—, —OC{$(C_1-C_6)$alkyl}$_2$—, or —CH=CH—;
  — — — — — is a single bond or is —C(B)(D)—, wherein B and D are each independently hydrogen, $(C_1-C_6)$alkyl, or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, $-(CH_2)_{0-4}C(=O)(C_1-C_6)$alkyl, $-UC(=O)(C_1-C_6)$alkyl, benzyl, $-OSO_2(CH_2)_{0-4}CH_3$, $-U(CH_2)_{1-4}COOR_p$, $-(CH_2)_{0-4}COOR_p$, $-U(CH_2)_{2-4}OR_p$, $-(CH_2)_{0-4}OR_p$, $-U(CH_2)_{1-4}C(=O)R_k$, $-(CH_2)_{0-4}C(=O)R_k$, $-U(CH_2)_{1-4}R_k$, $-(CH_2)_{0-4}R_k$, or $-U(CH_2)_{2-4}OC(=O)R_p$; wherein U is O, $N(R_m)$, or S;

Z is $-O-$, $-OCH_2-$, $-CH_2O-$, $-C(=O)O-$, or $-N(R_q)-$;

$R_k$ is amino optionally substituted with one or two $(C_1-C_6)$alkyl; or an N-heterocyclic ring optionally containing 1 or 2 additional $N(R_l)$, S, or nonperoxide O, wherein $R_l$ is $H(C_1-C_6)$alkyl, phenyl, or benzyl;

$R_n$ and $R_o$ are independently hydrogen, $(C_1-C_6)$alkyl, phenyl, benzyl or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_q$ are independently hydrogen, $(C_1-C_6)$alkyl, phenyl, benzyl, or $(C_1-C_6)$alkanoyl;

or a pharmaceutically acceptable salt thereof.

35. A therapeutic method for preventing or treating a condition or symptom associated with osteoporosis comprising administering to a mammal in need of such therapy, an effective amount of a compound of formula VI:

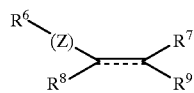

(VI)

wherein $R^6$ is $(C_1-C_6)$alkyl, or aryl, optionally substituted by 1, 2, or 3 V;

$R^7$ is phenyl, optionally substituted by 1, 2, or 3 V; or $R^7$ is $(C_1-C_{12})$alkyl, halo$(C_1-C_{12})$alkyl, $(C_3-C_6)$cycloalkyl, $(C_1-C_6)$alkylcyclo$(C_1-C_6)$alkyl, $(C_3-C_6)$cycloalkenyl or $(C_1-C_6)$alkyl$(C_3-C_6)$cycloalkenyl;

$R^8$ is phenyl substituted at the 2-position with Rj, and optionally substituted by 1, 2, or 3 V;

$R^9$ and $R_j$ together are $-CH_2CH_2-$, $-S-$, $-O-$, $-N(H)-$, $-N\{(C_1-C_6)alkyl\}-$, $-OCH_2-$, $-OC\{(C_1-C_6)alkyl\}_2-$, or $-CH=CH-$;

— — — — — is a single bond or is $-C(B)(D)-$, wherein B and D are each independently hydrogen, $(C_1-C_6)$alkyl or halo;

V is $OPO_3H_2$, $(C_1-C_6)$alkyl, $(C_1-C_6)$alkoxy, mercapto, $(C_1-C_4)$alkylthio, halo, trifluoromethyl, pentafluoroethyl, nitro, $N(R_n)(R_o)$, cyano, trifluoromethoxy, pentafluoroethoxy, benzoyl, hydroxy, $-(CH_2)_{0-4}C(=O)(C_1-C_6)$alkyl, $-UC(=O)(C_1-C_6)$alkyl, benzyl, $-OSO_2(CH_2)_{0-4}CH_3$, $-U(CH_2)_{1-4}COOR_p$, $-(CH_2)_{0-4}COOR_p$, $-U(CH_2)_{2-4}OR_p$, $-(CH_2)_{0-4}OR_p$, $-U(CH_2)_{1-4}C(=O)R_k$, $-(CH_2)_{0-4}C(=O)R_k$, $-U(CH_2)_{1-4}R_k$, $-(CH)_{0-4}R_k$, or $-U(CH_2)_{2-4}OC(=O)R_p$; wherein U is O, $N(R_m)$, or S;

Z is $-(CH_2)_{1-3}-$, $-O-$, $-OCH_2-$, $-CH_2O-$, $-C(=O)O-$, $-N(R_q)-$, $C=O$, or a covalent bond;

$R_k$ is amino, optionally substituted with one or two $(C_1-C_6)$alkyl; or an N-heterocyclic ring optionally containing 1 or 2 additional $N(R_l)$, S, or nonperoxide O, wherein $R_l$ is $H(C_1-C_6)$alkyl, phenyl, or benzyl;

$R_n$ and $R_o$ are independently hydrogen, $(C_1-C_6)$alkyl, phenyl, benzyl, or $(C_1-C_6)$alkanoyl; or $R_n$ and $R_o$ together with the nitrogen to which they are attached are a 3, 4, 5, or 6 membered heterocyclic ring;

$R_p$ is H or $(C_1-C_6)$alkyl; and $R_m$ and $R_l$ are independently hydrogen, $(C_1-C_6)$alkyl, phenyl, benzyl, or $(C_1-C_6)$alkanoyl;

or a pharmaceutically acceptable salt thereof;

provided $R^6$ is not phenyl or phenyl substituted by 1 or 2 V.

* * * * *

UNITED STATES PATENT AND TRADEMARK OFFICE
CERTIFICATE OF CORRECTION

PATENT NO. : 6,410,587 B1
DATED : June 25, 2002
INVENTOR(S) : Grainger et al.

It is certified that error appears in the above-identified patent and that said Letters Patent is hereby corrected as shown below:

Title page,
Item [56], References Cited, U.S. PATENT DOCUMENTS,
"4696949 A", delete "9/1987" and insert -- 8/1987 --, therefor.
"5484808 A" delete "et al" after "Grinnell".
"5716981 A" delete "514/2" and insert -- 514/449 --, therefor.
"Grainger, D.J., et al.," delete "TFG-Beta" and insert -- TGF-Beta --, therefor.
Second "Grainger, D.J., et al.," deete ")" after "Factor-beta".
"Jones, R.H., et al." insert -- beta -- after "Lens".
First "McCagne, et al.", insert -- ) -- after "-butene".

Column 4,
Line 27, delete "–O—N(H)-" and insert -- –O- -N(H)- --, therefor.
Line 41, delete "–$U(CH2)_{1-4}R_k$" and insert -- –$U(CH2)_{1-4}R_k$ --, therefor.

Column 8,
Line 18, delete "(□)" and insert -- (○) --, therefor.
Line 19, delete "(○)" and insert -- (□) --, therefor.
Line 46, delete "a" before "indication" and insert -- an --, therefor.

Column 9,
Line 23, delete "," after "the".

Column 12,
Line 37, delete "3,5 dibromoacetylsalicylic" and insert -- 3,5-dibromoacetylsalicylic --, therefor.

Column 13,
Line 38, delete "NMS" and insert -- NFkB --, therefor.

Column 15,
Line 30, delete "cells" before "types" and insert -- cell --, therefor.

Column 17,
Line 35, delete ":" after "naphthylpropyl" and insert -- ; --, therefor.

Column 18,
Line 21, delete "$(C_1-C_6)$alkanoyloxy" and insert -- $(C_2-C_6)$alkanoyloxy --, therefor.
Line 67, delete "(II)" after "formula" and insert -- (III) --, therefor.

Column 20,
Line 28, delete "$CO_2(_1-C_4)$alkyl" and insert -- $CO_2(C_1-C_4)$alkyl --, therefor.
Line 29, insert -- ; -- after "alkyl]".
Line 51, delete "is.$(C_1-C_6)$alkyl" and insert -- is $(C_1-C_6)$alkyl --, therefor.
Line 64, delete "$R^1$is" and insert -- $R^1$ is --, therefor.

UNITED STATES PATENT AND TRADEMARK OFFICE
CERTIFICATE OF CORRECTION

PATENT NO. : 6,410,587 B1
DATED : June 25, 2002
INVENTOR(S) : Grainger et al.

It is certified that error appears in the above-identified patent and that said Letters Patent is hereby corrected as shown below:

Column 22,
Line 18, delete "formulas" and insert -- formula --, therefor.

Column 23,
Line 11, delete "nanhydrous" and insert -- anhydrous --, therefor.
Line 63, delete "ethy,2-cyanoethyl" and insert -- ethy, 2-cyanoethyl --, therefor.

Column 24,
Line 19, insert -- ( -- before "102b".
Line 65, insert -- . -- after "thereof".

Column 25,
Line 32, insert -- ( -- before "102b".
Line 48, delete "$R^{11}$" and insert -- $R^{17}$ --, therefor.

Column 26,
Line 34, delete "5" after "*Carcinogenesis*" and insert -- 15 --, therefor.
Line 48, insert -- 51, -- before "5851".

Column 30,
Line 66, delete "urged" after "commonly" and insert -- used --, therefor.

Column 31,
Line 38, delete "224" and insert -- 294 --, therefor.
Line 48, delete "(I)" before "explant" and insert -- (i) --, therefor.

Column 32,
Line 13, delete "calorimetrically" and insert -- colorimetrically --, therefor.

Column 36,
Line 67, delete "crosslinking" and insert -- cross-linking --, therefor.

Column 37,
Line 65, insert -- . -- after "area".

Column 42,
Lines 3 and 4, delete "PF4" and insert -- PF-4 --, therefor.
Line 9, delete "(235,000xg)" and insert -- (235,000 x g) --, therefor.
Line 25, delete "," after "instructions" and insert -- . --, therefor.

Column 44,
Line 36, delete "subtraction" and insert -- subfraction --, therefor.

UNITED STATES PATENT AND TRADEMARK OFFICE
CERTIFICATE OF CORRECTION

PATENT NO. : 6,410,587 B1
DATED : June 25, 2002
INVENTOR(S) : Grainger et al.

It is certified that error appears in the above-identified patent and that said Letters Patent is hereby corrected as shown below:

Column 46,
Line 10, delete "(NH)" and insert -- (MI) --, therefor.

Column 49,
Line 41, delete "9 am" and insert -- 9 a.m. --, therefor.
Line 54, delete "PF4" and insert -- PF-4 --, therefor.

Column 50,
Line 11, insert -- ( -- before "Promega".

Column 53,
Line 13, delete "droplets<50" and insert -- droplets < 50 --, therefor.
Line 14, delete "staining>500 $\mu$m" and insert -- staining > 500 $\mu$m$^2$ --, therefor.

Column 54,
Line 6, delete "wag" and insert -- was --, therefor.

Column 56,
Line 49, delete "(-16%/)" and insert -- (-16%) --, therefor.
Line 49, delete "(-12%/)" and insert -- (-12%) --, therefor.
Line 50, delete "(+10%/)" and insert -- (+10%) --, therefor.

Column 58,
Line 57, delete "dose" and insert -- doses --, therefor.

Column 60,
Line 8, insert -- . -- after "ER".
Line 34, delete "." after "ER".

Column 64,
Line 64, delete "," after "(C$_1$-C$_6$)alkylcyclo", therefor.

Column 67,
Line 27, insert -- , -- after "1".
Line 45, delete "-U(CH$_2$)$_{1-4}$C(=)R$_k$" and insert -- -U(CH$_2$)$_{1-4}$C(=O)R$_k$ --, therefor.

Column 68,
Line 60, insert "," after "benzyl".

Column 69,
Line 54, delete "-OCH$_2$—" and insert --  —OCH$_2$— --, therefor.
Line 67, delete "administer" and insert -- administering --, therefor.

UNITED STATES PATENT AND TRADEMARK OFFICE
CERTIFICATE OF CORRECTION

PATENT NO. : 6,410,587 B1
DATED : June 25, 2002
INVENTOR(S) : Grainger et al.

It is certified that error appears in the above-identified patent and that said Letters Patent is hereby corrected as shown below:

Column 70,
Line 26, delete "," after "3".

Column 71,
Line 21, delete "($C_3$14 $C_6$)cycloalkyl" and insert -- ($C_3$-$C_6$)cycloalkyl --, therefor.
Line 25, delete "," after "3".
Line 31, delete "($C_1$-$C_6$)alkylthio" and insert -- ($C_1$-$C_4$)alkylthio --, therefor.

Column 72,
Line 12, delete "($C_1$-$C_6$)alkyl" and insert -- ($C_1$-$C_4$)alkyl --, therefor.
Line 14, delete "$C_1$-$C_6$)alkyl($C_1$-$C_6$)cycloalkenyl" and insert -- $C_1$-$C_6$)alkyl($C_3$-$C_6$) cycloalkenyl --, therefor.
Line 33, delete "—($CH_2$)0-4COOR$_p$" and insert -- —($CH_2$)$_{0-4}$COOR$_p$ --, therefor.
Line 35, delete "—($CH_2$)R$_k$" and insert -- —($CH_2$)$_{0-4}$R$_k$ --, therefor.

Column 73,
Line 2, delete "($C_3$-$C_6$)cycloalkoxy" and insert -- ($C_3$-$C_6$)cycloalkyl --, therefor.
Line 7, delete "heteroalkyl" and insert -- heteroaryl --, therefor.
Line 18, delete "N($R_n$)($R_n$)" and insert -- N($R_n$)($R_o$) --, therefor.
Line 21, insert -- , -- after "benzyl".

Column 75,
Line 15, delete "O($CH_2$)$_2$ R$_k$" and insert -- —O($CH_2$)$_2$ R$_k$ --, therefor.

Column 76,
Line 20, delete "diseaSe" and insert -- disease --, therefor.
Line 43, insert -- is -- before "—C(B)(D)—".

Column 77,
Line 39, insert -- , -- after "—O—".

Column 78,
Lines 55, 58 and 61, delete "23, and 24" and insert -- 26, and 27 --, therefor.
Line 61, insert -- any one of -- before "claims".

Column 79,
Line 21, delete "—CH=C—" and insert -- —CH=CH— --, therefor.

Column 80,
Line 7, delete second instance of "$R^9$ and $R_j$ together are".
Line 10, delete "13" after "— — — —".
Line 19, delete "—($CH_2$)$_{0-4}$COOR$_i$" and insert -- —($CH_2$)$_{0-4}$COOR$_p$ --, therefor.

Page 4 of 5

UNITED STATES PATENT AND TRADEMARK OFFICE
CERTIFICATE OF CORRECTION

PATENT NO. : 6,410,587 B1
DATED : June 25, 2002
INVENTOR(S) : Grainger et al.

It is certified that error appears in the above-identified patent and that said Letters Patent is hereby corrected as shown below:

Column 81,
Line 18, insert -- , -- after "benzyl".
Line 41, insert -- , -- after "$(C_3-C_6)$cycloalkenyl".

Column 82,
Line 9, insert -- , -- after "$(C_1-C_6)$alkyl".
Line 19, delete "—$(CH)_{0-4}R_k$" and insert -- —$(CH_2)_{0-4}R_k$ --, therefor.
Line 35, delete "$R_1$" and insert -- $R_q$ --, therefor.

Signed and Sealed this

Second Day of September, 2003

JAMES E. ROGAN
*Director of the United States Patent and Trademark Office*